United States Patent [19]
Luo et al.

[11] Patent Number: 6,051,437
[45] Date of Patent: Apr. 18, 2000

[54] OPTICAL CHEMICAL SENSOR BASED ON MULTILAYER SELF-ASSEMBLED THIN FILM SENSORS FOR AQUACULTURE PROCESS CONTROL

[75] Inventors: Shufang Luo; K. Peter Lo, both of Blacksburg, Va.; Howard P. Groger, Gainesville, Fla.; Russell J. Churchill, Radford, Va.

[73] Assignee: American Research Corporation of Virginia, Radford, Va.

[21] Appl. No.: 09/071,775

[22] Filed: May 4, 1998

[51] Int. Cl.[7] ................................................... G01N 21/64
[52] U.S. Cl. ..................... 436/172; 422/82.05; 422/82.08
[58] Field of Search ............................... 422/82.05, 82.08, 422/82.09, 82.11; 436/164, 172

[56] References Cited

U.S. PATENT DOCUMENTS

| | | |
|---|---|---|
| 4,050,895 | 9/1977 | Hardy et al. . |
| 4,548,907 | 10/1985 | Seitz et al. . |
| 4,582,809 | 4/1986 | Block et al. . |
| 4,654,532 | 3/1987 | Hirschfeld . |
| 4,803,049 | 2/1989 | Hirschfeld et al. . |
| 4,815,843 | 3/1989 | Tiefenthaler et al. . |
| 4,844,613 | 7/1989 | Batchelder et al. . |
| 4,877,747 | 10/1989 | Stewart . |
| 4,929,561 | 5/1990 | Hirschfeld . |
| 5,019,350 | 5/1991 | Rhum et al. . |
| 5,045,282 | 9/1991 | Kritzman et al. . |
| 5,093,266 | 3/1992 | Leader et al. . |
| 5,096,671 | 3/1992 | Kane et al. . |
| 5,114,676 | 5/1992 | Leiner et al. . |
| 5,194,393 | 3/1993 | Hugl et al. . |
| 5,344,784 | 9/1994 | Attridge . |
| 5,521,702 | 5/1996 | Salamon et al. ..................... 422/82.05 |
| 5,629,213 | 5/1997 | Kornguth et al. ..................... 422/82.05 |

OTHER PUBLICATIONS

Ayyagar, M. et al "Molecular self assembly on optical fiber–based fluorescence sensor" SPIE vol. 2068, pp. 168–178 (1994).

Yang, X. et al "Polyelectrolyte and molecular host ion self–assembly to multilayer thin films: An approach to thin film chemical sensors" Sensors and Actuators B, vol 45, pp. 87–92 (1997).

Blyler, L.L., Jr., et al., "Optical Fiber Chemical Sensors Utilizing Dye–doped Silicone Polymer Claddings," Polymer Engineering and Science, vol. 29 (17), 1989, pp. 1215–1218.

Caglar, P. and Narayanaswamy, R., "Ammonia–sensitive Fiber Optic Probe Utilizing an Immobilized Spectrophotometric Indicator," Analyst, vol. 112, 1987, pp. 1285–1288.

Carraway, E.R., et al., "Photophysics and Photochemistry of Oxygen Sensors Based on Luminescent Transition–metal Complexes," Analytical Chemistry, vol. 63, 1991, pp. 337–342.

Easter, C., "Water Chemistry Characterization and Component Performance of a Recirculating Aquaculture System Producing Hybrid Stripped Bass," Master Thesis, Virginia Polytechnic Institute and State University, Blacksburg, Virginia, 1992, pp. 14–18, 47–51, 55, 70–71, 77–84, 134–143.

Fox, J.B., "The Determination of Nitrite: A Critical Review," CRC Critical Reviews in Analytical Chemistry, vol. 15, 1985, pp. 283–313.

Giuliani, J.F., Wohltjen, H. and Jarvis, N.L., "Reversible Optical Waveguide Sensor for Ammonia Vapors," Optics Letters, vol. 8, 1983, pp. 54–56.

(List continued on next page.)

*Primary Examiner*—Jeffrey Snay
*Attorney, Agent, or Firm*—James Creighton Wray; Meera P. Narasimhan

[57] ABSTRACT

Optical chemical probes have layers of anionic and cationic polyelectrolytes and one or more dyes incorporated into these layers. The probes are placed into the medium and the dye or dyes react in the presence of the corresponding chemical. Color changes may be observed manually or by a photo detector. A light source may be employed to increase the optical signal received from the probe. Further, a waveguide may be used to trap multiple optical signals. The invention is used for chemical analysis.

24 Claims, 45 Drawing Sheets

OTHER PUBLICATIONS

Groger, H.P., et al., "Thin Film Sensors to Evaluate Chemical and Biological Threats to Army Structures," SBIR Phase II Report, 1995, Contract No. DAAL01–913–C–4049.

Hirayama, K., Mizuma, H. and Mizue, Y., "The Accumulation of Dissolved Organic Substances in Closed Recirculation Culture Systems," Aquacultural Engineering, vol. 7, 1988, pp. 73–87.

Shahariari, M.R., Zhou, Q. and Sigel G.H. Jr., "Porous Optical Fibers for High–sensitivity Ammonia–Vapor Sensors," Optics Letters, 1988, vol.13, pp. 407–409.

Wolfbeis, O.S. and Posch, H.E., "Fiber–optic Fluorescing Sensor for Ammonia," Analytica Chimica Acta, vol. 185, 1986, pp. 321–327.

Zhou, Q., et al. "Porous Plastic Optical Fiber Sensor for Ammonia Measurement," Applied Optics, vol. 28, 1989, pp. 2022–2025.

R. Churchill et al., "Self–assembled Thin Film Sensors for Aquaculture Process Control," SBIR Phase II Final Report, Dec. 30, 1995.

Y. Haruvy et al., "Sol–Gel Preparation of Optically Clear Supported Thin Film Glasses Embodying Laser Dyes," Supramolecular Architecture, Chapter 28, pp. 405–424, American Chemical Society, 1992.

D. Levy, "Sol–gel glasses for optics and electro–optics," Journal of Non–Crystalline Solids 147 & 148 (1992) pp. 508–517, North–Holland.

R. Reisfeld and C. Jørgensen, "Optical Properties of Colorants or Luminescent Species in Sol–Gel Glasses," Structure and Bonding 77, ©Springer–Verlag, Berlin, Heidelberg, pp. 240–247, 1992.

R. Zusman et al., "Doped Sol–Gell Glasses as Chemical Sensors," Journal of Non–Crystalline Solids 122 (1990) pp. 107–109, North Holland.

J. Jahns and B. Acklin, "Integrated planer optical imaging System with high interconnection density," Optics Letters, vol. 18, No. 19, pp. 1594–1596, Oct. 1, 1993.

A. Tanguay, Jr., "Integrated Optical Information Processing," Final Research Report, pp. 63–71, Research Period Sep. 1, 1985—Aug. 31, 1987.

A. Brett et al., "Digital parallel acquisition in frequency domain fluorimetry," Rev. Sci. Instrum. 60 (9), pp. 2929–2936, Sep. 1989.

Y. Haruvy et al., "Supported sol–gel thin film glasses embodying laser dyes II: Three layered wave guide assemblies," SPIE vol. 1590 Submolecular Glass Chemistry and Physics, pp. 59–70, 1991.

R. Chen et al., "1–to–12 surface normal three–dimensional optical interconnects," Appl. Phys. Lett., vol. 63, No. 14, pp. 1883–1885, Oct. 1993.

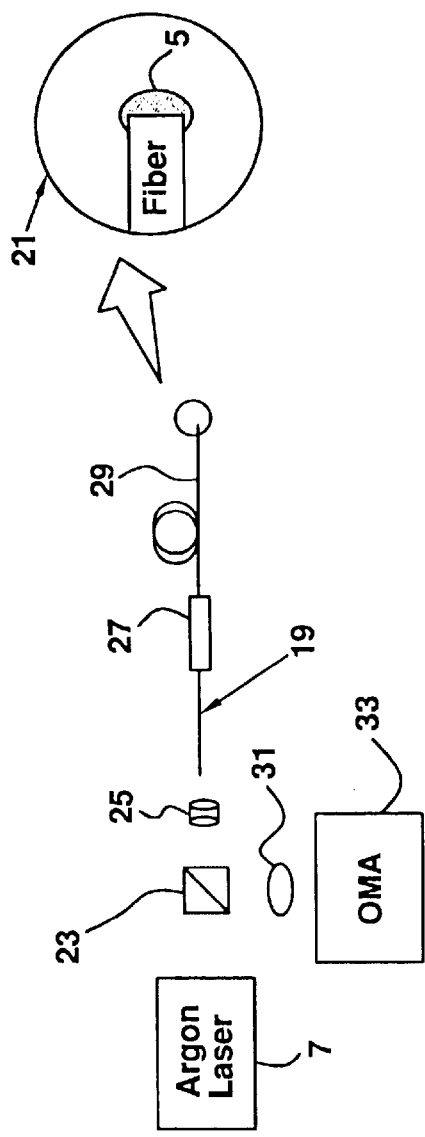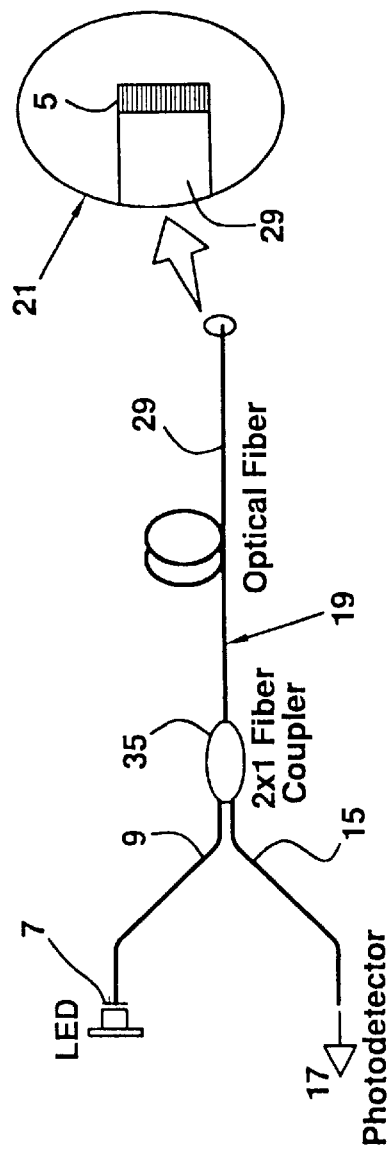

Without Signal Averaging

With 8 Times Signal Averaging

OPTICAL CHEMICAL SENSOR BASED ON MULTILAYER SELF-ASSEMBLED THIN FILM SENSORS FOR AQUACULTURE PROCESS CONTROL

This invention was made with Government support under Grant Number 93-33610-9096 awarded by the Department of Agriculture. The Government has certain rights in this invention.

BACKGROUND OF THE INVENTION

Needs exist for sensitive low-cost optical instruments which can detect trace levels of gases or volatiles in solution or in air.

The rapid increase in world seafood production has placed a competitive burden on the U.S. fishing and fish-farming industries, and has accelerated the development of high-density closed-cycle aquaculture (HDCCA) unit operations to provide seafood products at a competitive unit cost. Quality control in HDCCA requires rapid analysis of critical chemical concentrations of dissolved-oxygen and dissolved-ammonia in recycled water streams; however, no single sensor or group of sensors is currently available to provide timely information on water quality throughout HDCCA facility.

The use of aquaculture for production of seafood products has increased dramatically from one million metric tons annually in 1966 to eleven million metric tons in 1987. Among aquacultural systems, closed cycle facilities are attracting great interest as a result of the increased productivity and decreased environmental damage associated with water reuse.

The effective operation of closed cycle aquaculture facilities requires the development of in-process monitors to alert service personnel to a reduction in dissolved-oxygen or increased ammonia or nitrite that may result in decreased product quality, reduced yield or fish kills.

It has been shown that the buildup of organic carbon and inorganic substances including ammonia, nitrates and phosphates may be implicated in reduced fish quality. The benefits of continuous monitoring of those organic and inorganic materials are found in increased process density afforded by rapid response to anoxic conditions, reduced product loss from toxic material buildup or disease and improved competitiveness related to product quality. Although several techniques have been considered to provide those important measurements, no single technique has demonstrated sufficient versatility to address each of those sensor requirements.

HDCCA operations have become increasingly important due to increased demand for seafood products, because of health consciousness and decreasing availability due to aggressive harvesting practices. Aquaculture systems based on recirculating water have become popular due mainly to reduced water supply demand as well as wastewater discharge. Such systems can also solve many of the seasonal and site-limiting problems of pond systems by being placed inside buildings, where the entire fish culture environment can be controlled and managed.

In-process monitoring of certain chemicals in HDCCA systems becomes important because such information can be used in automatic control systems and by human operators. Continuous monitoring of environmental conditions is important because of effects on fish health, feed utilization, growth rates, stocking densities, carrying capacities and waste management. The environmental variables in aquaculture processes include temperature, dissolved-oxygen, pH, ammonia, nitrite, nitrate, suspended solids, turbidity, salinity and water flow rates. Needs exist for sensors for monitoring dissolved-oxygen, dissolved ammonia and nitrate/nitrite in HDCCA waters.

Dissolved-oxygen concentration is perhaps one of the most critical factors for healthy fish growth. Fish rely on the oxygen dissolved in water to support their metabolism. A decrease in dissolved-oxygen level below a certain critical value will result in fish kill in a matter of several minutes. Therefore, it is critically important to be able to monitor dissolved-oxygen in HDCCA facilities. The ability of water to carry oxygen depends on temperature, pressure and dissolved salts.

Various species of fish can tolerate different levels of dissolved-oxygen concentration. For example, salmonid need a minimum level of 5.0–5.5 mg/L of dissolved-oxygen for healthy growth, while carp, catfish and tilapia can withstand dissolved-oxygen levels of below 2 mg/L for short periods of time.

Current oxygen sensors are oxygen-selective membrane electrodes of the polarographic or galvanic type, which consist of two metal electrodes in contact with electrolyte and separated from the test solution by a gas permeable membrane. To measure dissolved-oxygen concentration, the oxygen permeates a plastic membrane (polyethylene or fluorocarbon), reacts with the reactive electrolyte and is measured using the metal electrodes. With that type of sensor, three problems arise when used in an aquaculture process.

Firstly, the sensor consumes a portion of the oxygen surrounding the sensor head, thereby requiring water to be recirculated to the surface of the sensor head. Secondly, bacteria grow on the gas-permeable membrane, accumulate and prevent oxygen penetration. As a result, cleaning of the membrane is needed at least once a day. Thirdly, the signal from that type of sensor drifts with time. In addition, the sensor head is bulky and prohibitively expensive.

Silicone polymer is the most commonly used solid support for optical oxygen indicators, because of its oxygen permeability and also because it does not quench the fluorescence of most of the oxygen indicators. Most work on optical sensors for dissolved-oxygen concentration has been based on the water soluble indicator ruthenium(II) tris (bipyridyl) $(Ru(bpy)_3^{2+})$ dichloride in silicone. For example, complexes of ruthenium ions with bipyridine or phenanthroline ligands may be used to develop an oxygen sensor based on fluorescence quenching. Sensors based on ruthenium with phenanthroline ligands have been found to be less sensitive to changes in the embedding media than those based on the bipyridyl ligand.

Rapid evaluation of HDCCA water quality also requires data on the concentration of ammonia-nitrogen. One of the most toxic chemicals to fish is the un-ionized form of ammonia-nitrogen in the main excretory products of fish, and is most likely to accumulate over time in HDCCA systems. In water, the ammonia molecule exists in equilibrium with its ionized form as follows:

(1)

The ammonium ion $(NH_4^+)$ is fairly innocuous to fish, whereas free ammonia $(NH_3)$ is highly toxic, and a level of 0.02 mg/L is generally regarded as the maximum acceptable limit for healthy fish.

Currently, there is no in-process ammonia sensor for use in aquaculture processes although several electrochemical instruments are available for laboratory analysis. Total ammonia-nitrogen concentration is determined by a wet chemistry process, such as the Nessler method, which has a sensitivity of 20 µg/L using a spectrophotometer. The ammonia-selective electrode has drawbacks of not having sufficient sensitivity and being subject to biofouling and interference from dissolved ions, such as mercury and silver.

Optical absorption-based sensors have been widely used for ammonia detection. For example, bromothymol blue, oxazine 750 perchlorate, and bromocresol purple have been used as absorbing indicators for ammonia detection. Also a fluorescent dye, acridine orange, has been used as an indicator for ammonia. Although the instrumentation of those optical techniques to detect ammonia is different, the basic principle remains the same.

The principle underlying those detection schemes is based on the change of optical signal as ammonia gas traverses a permeable membrane and reacts with a pH sensitive indicator. The pH indicator changes the absorption spectrum, thereby indicating the concentration of ammonia. This scheme is feasible because ammonia is an alkaline gas and only several other gases, such as dimethylamine, trimethylamine and hydrazine hydrate (rarely found to have enough concentration to interfere with detection), are more basic than ammonia. The reaction of ammonia, $NH_3$, with a pH-sensitive dye molecule, such as bromocresol purple (BCP) and bromothymol blue (BTB), in the aqueous media is summarized as follows:

(2)

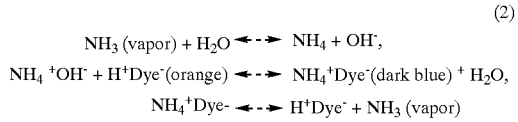

Toxicity of nitrite to fish is also of concern in aquaculture systems, although fish are much less sensitive to nitrite than to dissolved-oxygen and un-ionized ammonia. Nitrite is known to cause conversion of hemoglobin to methhemoglobin, which is incapable of binding and transporting oxygen. The level of nitrite sensitivity varies widely across various fish species. For example, toxication is observed for rainbow trout at 22 mg/L, but at 453 mg/L for large mouth bass. Current methods of measuring nitrite concentration in aquaculture processes involve the use of diazotization, a method involving the formation of reddish purple azodye produced at a pH of 2.0 to 2.5 by coupling diazotized sulfanilic acid with N-(1-naphthyl)-ethylenediamine dihydrochloride. With the use of a spectrophotometer, that method determines nitrite concentrations as low as 1 mg/L.

Optical methods for detection of nitrite have been evaluated. Most of those methods are based on the four-step Griess reaction resulting in the formation of a diazo dye. Nitrite ions react with sulfanilamide to form diazonium cations in acidic solution. That is coupled to N-(1-naphthyl) ethylenediamine (NED) to form the dye. The dye has absorption maxima at wavelengths of 350 nm and 540 nm and is suitable for use with green emitting helium-neon laser excitation. However, that analytical method is not compatible with optical sensors for continuous monitoring because of the number of steps involved and the requirement for an acidic environment to form the diazonium cations.

Development of dissolved-oxygen and dissolved-ammonia sensors is required, because dissolved-oxygen in HDCCA systems can fluctuate rapidly, and lack of oxygen for several minutes can result in fish kill and because extremely low concentrations of dissolved-ammonia can be deleterious to fish survival and taste.

SUMMARY OF THE INVENTION

The present sensor allows ammonia to be detected at 20 parts-per-billion using a small instrument system. Carbon dioxide can be detected at trace concentrations using a range of pH sensitive dyes. An instrument employing differing dyes immobilized in differing polymer matrices may provide a means of detecting and identifying any chemical. The present invention can surpass the capabilities of the Figeroa sensor, providing part-per-billion sensitivities.

The present invention relates to thin-film optical sensors that provide continuous monitoring of oxygen, ammonia and nitrate/nitrite in HDCCA systems. The dissolved-ammonia sensor was able to distinguish $10^{-7}$ M ammonium hydroxide in water from $10^{-8}$ M solutions. The sensor is reversible in that removal of the ammonium hydroxide resulted in a reversion to the original absorption state.

The present invention is a rugged optical sensor based on the interaction between fluorescence or absorption dyes doped thin films and the chemical species of interest. Modular optical sensors for dissolved or gaseous oxygen, ammonia and nitrate/nitrite are provided by the present invention. A fluorescence-based multiplexed sensor network is created through continuous monitoring of dissolved-oxygen levels in a high closed-cycle aquaculture facility.

Several optical fiber sensors for measurement of dissolved-oxygen are possible using fluorescence from ruthenium-based probes. Sensors were fabricated using ruthenium tris(bipyridyl) dichloride hydrate ($Ru(bpy)_3Cl_2$) or ruthenium (II) tris(4,7-diphenyl-1,10-phenanthroline) dichloride ($Ru(Ph_2phen)_3^{2+}$) as fluorescent probe material.

An absorption and fluorescence based sensor for dissolved-ammonia is fabricated using multiple-layer self-assembled thin films formed by alternately depositing thin layers of poly styrene sulfonic acid (PSSA) and poly (allylamine) hydrochloride (PAA) containing bromocresol purple and coating the resulting structure with Teflon.

To address the problems of existing sensors, optical fiber sensors have been developed for detection of dissolved-oxygen. Several fluorescent indicators are available to detect dissolved-oxygen using optical methods. Those indicators include polycyclic aromatic hydrocarbons (PAHs) such as pyrene, fluoranthene, decacyclene, diphenylanthracene and benzo(ghi)perylene, whose fluorescence signals are efficiently quenched in the presence of oxygen and are soluble in silicone polymer. Another group of indicators is the transition metal complexes of ruthenium, osmium, iridium and platinum which are more photostable and have relatively long fluorescence decay time (up to 5 µs).

The present optical sensors provide data on the quality of recycled water in high-density closed-cycle agricultural systems throughout the plant facility. Optical sources based on gallium nitride light-emitting diodes (LEDs) are available. This allows the fabrication of optical sensors for dissolved oxygen without the synthesis of near-infrared excitable dyes.

Sensors for dissolved-ammonia based on optical absorption were developed with self-assembled or solution-deposited polymer-immobilized dyes. The use of biodegradable polymer coatings on dissolved-oxygen and dissolved-ammonia sensors reduced fouling in aquacultural facilities. This improved the operational lifetime of optical fiber sensors under conditions where a buildup of organic matter at the probe surface may reduce probe sensitivity. The development of a facility-wide sensor network was approached through the design and development of networked optical oxygen sensors based on optical fiber excitation of an oxygen-sensitive fluorophore and optical fiber detection of the fluorescence.

Highly sensitive, rugged and reliable sensors employ fiber optic probes for continuous monitoring of oxygen, ammonia and nitrite in high-density closed-cycle aquaculture (HDCCA) systems.

The present invention relates to fluorophores sensitive to oxygen concentration and their immobilization into different matrices. Ruthenium (II) tris(bipyridyl) ($Ru(bpy)_3^{2+}$) dichloride was immobilized in a sol-gel material to provide one probe for dissolved-oxygen, and ruthenium (II) tris (4,7-diphenyl-1,10-phenanthroline) ($Ru(Ph_2phen)_3^{2+}$) dichloride was immobilized in silicone and used as a second dissolved-oxygen probe.

To fabricate $Ru(bpy)_2Cl_2$-doped sol-gel films, 360 $\mu l$ of $10^{-2}$M $Ru(bpy)_3Cl_2$ were added to a glass vial containing 2 ml of 0.01M HCl and 10 ml of methyltrimethoxysilane. The vial was heated at 75–76° C. in an oil bath for 7 minutes. During this period of time, bubbles were formed and the liquid became more viscous. Immediately after the sol-gel solution was removed from the oil bath, it was spin-coated on a precleaned glass slide. Several spin rates were applied to make films of various thicknesses. Later, the coated slides were heated in an oven at 60° C. for at least 2 hours. Thus, a clear, deep orange color and hard silica film were formed.

Ruthenium (II) tris(4,7-diphenyl-1,10-phenanthroline) ($Ru(Ph_2phen)_3^{2+}$) dichloride was synthesized by mixing 208 mg of $RuCl_3$, 1.33 g of 4,7-diphenyl-1,10phenanthroline, 25 ml of ethanol and a solution of hydroxylamine hydrochloride (140 mg) in 10 ml of water. A deep red color appeared during a refluxing period of 48 hours, which indicated the formation of this complex. The reaction mixture was evaporated to near dryness and the residue was dissolved in isoamyl alcohol and filtered. The filtrate was washed with an aqueous solution of sodium chloride and later removed by evaporation. A small amount of acetonitrile was added to the resulting residue to crystallize the free ligand. An eight-hour period was required for complete crystallization. After the free ligand was filtered, the filtrate was evaporated and the residue was dissolved in a hot 50% water-ethanol solution. After sodium chloride was added, the complex was precipitated, collected and washed with water. Later it was recrystallized from an equal-volume mixture of water, acetonitrile and ethanol.

Silicone rubber RTV-118 (General Electric) was used to immobilize $Ru(Ph_2phen)_3Cl_2$ for use in the dissolved-oxygen sensor. The uncured RTV-118 polymer was formed to a thick film by clamping between Teflon sheets. Complete curing in air took about a month since exposure was limited to the edges. The cured polymer was peeled from the Teflon sheet and washed with distilled water. Silicon rubber film was doped with $Ru(Ph_2phen)_3Cl_2$ by soaking the film in a methylene chloride ($CH_2Cl_2$) solution of $Ru(Ph_2phen)_3Cl_2$ ($10^{-3}$M) for 10 minutes. The film swelled in $CH_2Cl_2$ and took up the ruthenium complex. The concentration of the ruthenium complex in the film was controlled by adjusting the concentration of $Ru(Ph_2phen)_3Cl_2$ in $CH_2Cl_2$. The film was removed and rinsed quickly with $CH_2Cl_2$ to remove $Ru(Ph_2phen)_3Cl_2$ from the surface. Then the film was transferred to a glass jar and loosely covered. The $CH_2Cl_2$ was evaporated slowly and the film gradually returned to its original shape. Tests on dye leaching were performed by soaking the ruthenium complex-doped film in distilled water for one week.

The present invention relates to immobilized dye molecules in porous matrices for detecting dissolved-ammonia. Two techniques have been utilized for preparing thin-film ammonia sensors. One involved the use of solution casting to deposit a dye-doped polymer matrix and the other used a self-assembled polymer multilayer to immobilize the dye.

The present invention relates to optical absorption sensors based on bromocresol purple (BCP) immobilized in cellulose acetate. To accomplish this goal, 0.5 g of cellulose acetate polymer was first dissolved in 20 ml of acetone. To this solution 20 mg of BCP dye was added. A clean glass slide was then immersed in the solution and withdrawn from the solution at a speed of 0.2 cm/s. This dip-coating procedure was repeated to increase the probe thickness. The coating on one side of the film was then removed to reduce the background signal. The thin film-coated glass substrate was air-dried and later mounted in a flow cell for the subsequent tests. The same procedure was also applied to a nile blue/PEM system.

The present invention relates to probes based on 1,1',3, 3,3',3' hexamethylindodicarbocyanine iodide ($DiIC_1(5)$) codeposited with Nafion polymer. 1 ml of $10-3$ M $DiIC_1(5)$ in ethyl alcohol was mixed with 1 ml of 5 wt % Nafion solution. To this mixture 8 ml of ethyl alcohol were added and the resultant solution was stirred. Then about 150 $\mu l$ to 200 $\mu l$ of this solution was spread on a clean glass substrate and either air-dried at room temperature or oven-dried at 120° C. This procedure was also used to prepare oxazine 170 in Nafion and Zn(II)-tetra(4-carboxyphenyl)porphyrin (Zn (II)-TCPP) or Zn(II)-tetra(4-amino-phenyl)porphyrin (Zn (II)-TAPP) in Nafion as the polymer matrix. Bromothymol blue (BTB) was also immobilized in polymers, such as poly(4-vinylphenol) (PVPOH), poly(carbonate bisphenol A) (PCBA), poly(ethylene maleic anhydride) (PEM) and poly (vinylpyridine) (PVP).

Some of pH-sensitive absorbing and fluorescence dyes, such as bromocresol purple (BCP), chlorophenol red (CPR) and nitrazine yellow (NY), have been tested for their sensitivity to a small amount of ammonia. A typical thin film fabrication process involves the preparation of a polymeric coating solution and a suitable way of placing the film on the glass substrates. The coating solution consists of a polymer and a dye that are dissolved in a suitable low-boiling-point organic solvent. Dip- or spread-coating methods are employed to coat glass substrates with the polymer solution.

The second approach in preparing ammonia sensitive thin-films involved molecular self assembly of polymeric multilayers. This technique is based on the alternate adsorption of a polyelectrolyte to a substrate surface that carries the charge opposite to the deposition solution, and there is no covalent bond formed during the process. The technique requires two polyelectrolytes with opposite charges. Ammonia sensitive dyes can be incorporated through codeposition with a polymer.

The two ionic polymers employed are: poly(styrene sulfonic acid) sodium salt (PSSA), and poly(allylamine hydrochloride) (PAA). 200 mg of PSSA were dissolved in 100 ml of 0.01M HCl to make an anionic polymer solution, and 125 mg of PAA were dissolved in 100 ml of 0.01M HCl to make a cationic polymer solution. To the cationic polymer solution, about 55 mg of dye were added.

The dye used in developing ammonia sensors was bromocresol purple (BCP). The surface of the glass substrate must be cleaned well in order to achieve high uniformity. Detergent-cleaned glass substrates were further consecutively cleaned with chloroform, acetone and ethanol in an ultrasonic bath for 3 minutes each time. Then the glass substrates were placed in a hot "piranha" solution for several minutes and rinsed extensively with de-ionized water. They were later transferred to a 5% aqueous solution of 3-aminopropyltrimethoxysilane (pH=2.65, adjusted with concentrated HCl) and kept for 15 minutes to build a monolayer of amino group. The surface-modified glass slide was then rinsed with de-ionized water, and allowed to dry in air before being used for multilayer film deposition. The fresh surface-modified glass substrate was immersed in PSSA and PAA solutions alternatively to build up self-assembled multiple layers.

About three to four bilayers were required to achieve reasonable sensitivities. The glass substrate was later mounted in a flow cell and the ammonia gas generated from a permeation tube in an oven at a particular temperature was delivered to the cell with the flow of nitrogen. Liquid ammonium hydroxide was passed through the cell with the assistance of a pump. Uv/vis spectroscopy was used to characterize the dye incorporated in the multilayer assembly and its response to ammonia.

An anion-selective membrane was used to determine the concentration of nitrate ion in solution. Work was performed to incorporate ion-selective ionophores into poly(vinyl chloride) (PVC) membranes. Methyltridodecylammonium chloride (MTDACl) was used as an ionophore in the experiment and fluorescent octadecyl ester (FODE) or 5-(N-Octadecanoyl) aminofluorescein (N-ODAF) was used as pH indicator. The principle is based on the fact that when an $NO_{3-}$ ion is extracted from the solution into a PVC membrane, a proton is also co-extracted. Since a pH-sensitive fluorophore is incorporated into the membrane, the change in fluorescent intensity due to the change of membrane acidity can be detected and can be indirectly related to the concentration of nitrate ions.

The process can be illustrated by the following reaction schemes:

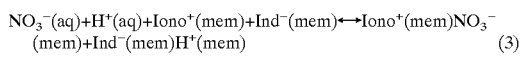

$$NO_3^-(aq)+H^+(aq)+Iono^+(mem)+Ind^-(mem) \leftrightarrow Iono^+(mem)NO_3^-(mem)+Ind^-(mem)H^+(mem) \quad (3)$$

The PVC membrane solution was prepared by dissolving 6.4 mg of FODE or 9.4 mg of N-ODAF, 11.2 mg of MTDACl and 158 mg of PVC in 10 ml of tetrahydrofuran, then 396 μl of diethylhexylsebacate were added to the above solution. Precleaned glass slides were dip-coated in the solution and the film on one side was later removed. The film was conditioned in buffers for more than 2 days before fluorescence measurements were made.

The present invention relates to a long-wavelength single-reaction optical fiber probe for nitrite involving the use of a nitrite-selective ion carrier bromo(pyridine)(5,10,15,20)-tetraphenyl-porphyrinato cobalt(III) (CoTPPP(py)Br) exhibited changes in optical absorptivity upon forming a complex with nitrite ions. The CoTPP(py)Br complex is known to exhibit a color change when nitrite displaced the bromide ion in the complex. Others make use of helium-neon lasers at wavelengths of 544 and 633 nm to determine the presence of the analyte in a membrane structure. The ratio of optical absorptivities can provide a sensitive measure of the presence of the nitrite ion.

The present invention relates to biodegradable polymer coatings to reduce the biofouling effect of the sensors in the HDCCA environment. Only hydrolyzable types of biodegradable polymers are used in HDCCA systems and the degradation products must be natural metabolites or biocompatible species that are not harmful to fish. It is well known that poly(x-hydroxy acids), such as L-lactic acid, D,L-lactic acid, and glycolic acid with ester bonds in the main chain, undergo both enzymatic and non-enzymatic hydrolysis. These biodegradable polymers have applications in medical fields, such as surgical sutures and asteroplastic materials, and are also useful in the area of drug delivery. An attempt to synthesize crosslinked biodegradable polymers of fine internal pore size was made. Initially, poly(lactic acid) of high and low molecular weights was synthesized by two methods: direct polycondensation and ring opening of the cyclic monomer. Finally, crosslinking poly(lactic acid) with tartaric acid was carried out to form crosslinked network with fine pore size. Biodegradability experiments were carried out in the presence of 0.1M phosphate buffer, pH 7.44 at 25° C.

Direct polycondensation of L-lactic acid was performed in a dry ampule by bubbling nitrogen into the mixture and heating for a total of 20 to 30 hours at 200° C. Upon cooling the viscous mixture turned glassy. The material was recovered by breaking the ampule followed by gas-phase chromatography (GPC) analysis or by dissolving the polymer in the chloroform and precipitating into methanol. The isolated polymer was dried prior to GPC analysis.

Direct polycondensation can also be performed in the presence of a catalyst, such as antimony oxide. The monomer was charged in an oven dried ampule and one drop of triphenyl phosphate, a color stabilizer, was added in addition to the catalyst. The mixture was heated to 180° C. for 4 hours and then under vacuum at 220° C. for a total of 15 to 30 hours. The viscous material was precipitated into methanol from chloroform solution. The isolated polymer was dried prior to GPC analysis.

The cyclic monomer was recrystallized from ethyl acetate. The anhydrous lactide was mixed with 0.03 wt % antimony triflouride. The mixture was heated to 140° C. under nitrogen for a total of 48 hours. The viscous dark brown mixture was cooled to room temperature, dissolved in chloroform and poured into a large volume of methanol to give a solid polymer. The isolated polymer was dried prior to GPC analysis.

The cyclic monomer D,L-lactide was charged into an oven dried ampule. The catalyst, stannous octanoate (0.02 wt %), was weighed in a fine capillary tube and the tube was inserted into the ampule. The tube was evacuated under reduced pressure for 2 hours and sealed. The sealed tube was placed into a preheated oil bath at 145° C. After 30 hours, the tube was brought to room temperature and was quenched to −78° C. before breaking the seal. The glassy polymer was soluble in chloroform to give a viscous solution, indicative of the formation of high molecular weight polymer. The polymer was purified by precipitation from chloroform into methanol. The isolated polymer was dried prior to GPC analysis.

L-lactic acid and L-tartaric acid were charged into a glass ampule (25×75 mm) with thin neck (8×35 mm). The tube was then immersed in a preheated oil bath maintained at 210° C. and stirred magnetically for 4 hours until gelation occurred. Nitrogen gas was bubbled through the reaction mixture at all times. Further curling was done for 5 hours at 195° C. After 5 hours the tube was cooled and the ampule was broken to recover the polyester. The recovered crosslinked polyester was subjected to continuous Soxhlet extraction with anhydrous THF to remove any soluble material. The insoluble portion was recovered and dried in the oven near a temperature of 65° C., and the amount of the crosslinker incorporated was analyzed via solid state NMR.

The large scale reactions were carried out to synthesize the crosslinked polyesters containing 15 and 25 mol % of crosslinker (tartaric acid). After subjection to Soxhlet extraction followed by vacuum drying, the polymers (2.0 g) were placed into a 40 ml solution of 0.1M phosphate buffer at 25° C. for a period of 2 to 10 days. The solid polymer was filtered and washed with 25 ml of 0.1M phosphate buffer and 10 ml of water. These polymers were then dried in a vacuum oven at 65° C. for 24 hours until a constant weight was obtained.

The present invention is optimization of sensor geometries to excite and collect fluorescent signals from indicator materials deposited on the thin-film sensor probes. Three dye-excitation methods were evaluated. These methods include transverse excitation and collection of fluorescence, excitation of dye deposited at the distal end of the fiber, and evanescent wave excitation and transverse collection of fluorescence. This produces optical sensor probes that are easily maintained or replaced.

The present invention is a multi-sensor system for monitoring chemical concentrations throughout an HDCCA facility. Work was involved in comparing two multiplexing techniques including wavelength-division multiplexing and frequency-division multiplexing to achieve multiple sensors having the minimum number of light sources, detection units and fiber transmission lines. Furthermore, the cost of the system was considered to achieve a salable sensor system.

The present invention relates to the acquisition of families of test data in a selected aquacultural setting. The sensor lifetime was estimated by monitoring the fluorescence signal of the oxygen sensitive Ru(Ph$_2$phen)$_3^{2+}$ films over a long period of time under continuous excitation. The films were excited using a blue LED (Nichia Model NLPB 300) emitting at center wavelength of 450 nm and at approximately 100 mW optical power. The accuracy of the sensor to determine gaseous and dissolved-oxygen was obtained by comparing with known values of premix oxygen concentrations or by comparing with a commercial Clark-type electrode sensor (Yellow Spring Model 50B). The sensor response time was estimated by measurement of the time required for the sensor to change from 90% of the final value for a change of oxygen level from 0 to 100%.

The present invention relates to optimization by taking into account sensor and coating chemistries, optical fiber sensor geometries and sensor multiplexing techniques to provide a robust, sensitive, reliable method of monitoring critical water parameters in HDCCA facilities. Work involving optimization of sensor chemistries was approached by identifying suitable fluorescence dyes for sensing dissolved-oxygen levels. Work was performed to determine whether osmium complexes could be used in place of Ru(Ph$_2$phen)$_3$Cl$_2$ to provide improved photostability under continuous excitation and increased sensitivity towards dissolved-oxygen levels.

Criteria used in selection of absorbent and fluorescent indicator materials in optical chemical sensors are:

High Quantum Efficiency
 The fluorophores must have high quantum efficiency and relatively long fluorescent decay time so that a phase fluorimeter can be designed.

High Photostability
 The fluorophores must be stable from photobleaching over a period of months under continuous excitation.

Low Solubility in Water
 Since the sensors are to be used underwater, the fluorophores must be insoluble in water; otherwise a protective barrier must to be deposited on the sensor surface to prevent the fluorophores from leaching into the water.

Availability of modulatable Light Sources
 To be acceptable to the HDCCA community, low-cost light sources, such as LEDs or laser diodes, must be developed. The emission spectra of the light sources must overlap with the absorption spectra of selected fluorophores.

Large Stoke's Shift for the Fluorescent Signal
 It is desirable that the fluorophores have a large Stoke's shift in their fluorescent spectra so that long-pass filter can be implemented to isolate fluorescence signals from excitation signals.

High Sensitivity and Selectivity
 It is desirable that the fluorophores have high sensitivity and selectivity to the analytes so that sensitivity of the optical probes can be enhanced.

Similarly, criteria for the selection of matrix materials to immobilize the fluorophores were developed as follows:

High Affinity and Permeability to Analytes
 This will improve the interaction of fluorophores with analytes and subsequently improve the sensitivity of the sensors.

Good Optical Characteristics
 The thin-film matrices should be smooth, non-scattering and able to transmit fluorescence signals.

Insolubility in Water
 Since the sensors are to be used underwater, insoluble films are required as protective overcoats to soluble matrices.

Surface Modifiable
 This will assure that fluorophores can be covalently bonded in the matrices.

Based on the above criteria, the fluorophore-polymer and absorber-polymer combinations for the oxygen, ammonia and nitrate/nitrite sensors were selected.

Based on data available in the technical literature, it was decided to design optical sensors using Ru(bpy)$_3$Cl$_2$ immobilized in a sol-gel-deposited silica matrix or Ru(Ph$_2$phen)$_3$Cl$_2$ in a silicone polymer matrix. Experiments on oxygen quenching of Ru(bpy)$_3$Cl$_2$-doped sol-gel thin films were performed using an argon-ion laser as the excitation source, and the fluorescence intensity was collected through evanescent waves. Nitrogen and oxygen gases were directed onto the dye-doped sol-gel film.

The basic principle underlying the detection of dissolved-ammonia based on absorbing or fluorescent pH indicators is as follows: as ammonia gas traverses a permeable membrane or thin film, it reacts with water in the membrane and dissociates into ammonium and hydroxide ions, thereby causing the pH of the membrane to increase and to alter the relative concentration ratio of the two forms of the pH indicator. If the pH indicator is an absorbing dye, its absorption spectrum will change in response to the ammonia concentration. If the pH indicator is fluorescent, its fluorescence spectrum will change accordingly to indicate the concentration of ammonia.

An evaluation of dye-polymer combinations for ammonia detection was conducted at American Research Corporation of Virginia. Several of the dyes evaluated have shown changes in spectroscopic properties upon interaction with ammonia. Certain metal porphyrins and metal phthalocyanines were chosen as transition metal complexes that were expected to form chelation compounds with ammonia. Several of the dyes tested have been commonly employed in the fabrication of ammonia optical sensors. The change in the absorption spectra of the dye results from the change in the pH of the medium, and is correlated to the change in ammonia concentration. In addition, several solvatochromic dyes were tested since these dyes respond to changes in the environment.

The polymers employed here are hydrophobic, gas permeable and can be dissolved in common low-boiling point solvents so that they easily can form a thin transparent film on the glass substrate. Table III lists the evaluation results of most of the dye-polymer combinations tested. The abbreviations can be found Ain the experimental section.

Several absorbing dyes immobilized in different polymer matrices (except Nafion) give reversible responses to ammonia. Dyes doped in Nafion usually show irreversible responses to ammonia, but with very low detection limits that can be used to develop very sensitive and disposable ammonia sensors. Transition metal compounds immobilized in polymer probably lose their ability to form chelation complexes with ammonia. This is possible since the association constant for the chelation complex is smaller than that for the polymer matrix.

Several methods to synthesize poly(lactic acid) were considered. The direct polycondensation in the absence of catalyst, involves heating the monomer L-lactic acid at 200° C. by bubbling nitrogen into the monomer solution. According to Table IV (entry 1 and 2), both the yield and the molecular weight of the polymer are time dependent due to the loss of the monomer and the cyclic molecules formed during this reaction.

The synthesis of poly(L-lactic acid) and poly(D,L-lactic acid) was also attempted with a catalyst, antimony oxide and a color stabilizer, triphenyl phosphate. The reactions were performed under vacuum for a period of 15 to 30 hours at 200° C. using a trap to recover water and volatile cyclic. The molecular weights (Table IV entry 3 and 4) of the two resulting polymers are considerably lower than the reactions without using the catalyst, while the yields improved to a great extend for the same period of reaction time.

The ring opening reaction was also investigated to synthesize high molecular weight polyester. The ring opening of L-lactide (a cyclic monomer of L-lactic acid) at 140° C. with antimony trifluoride produced a polymer (mol. wt.=6.5 kg/mol, Table IV entry 5) with poor recovery. Ring opening polymerization in a sealed tube, using stannous octanoate as a catalyst, results in a polymer with very high molecular weight of 99 kg/mol (Table IV entry 6) and extremely high yield, approaching 100%.

The approach to synthesize the crosslinked polyester is via direct polycondensation of monomer, L-lactic acid, in the presence of the crosslinker, tartaric acid. The experiments were performed with varied amounts of tartaric acid at 210° C. under nitrogen atmosphere. Except for 5 mol % crosslinker, all other combinations of the reaction mixture result in crosslinked polymers that were only swelled upon reflexing with THF and chloroform. The amount of tartaric acid (crosslinker) incorporated was calculated from solid state NMR spectra.

These results indicate that an increase in the tartaric acid composition in the reaction mixture resulted in an increase of the crosslinker content in the polymer network. The glass transition temperatures were also found to increase with the corresponding increase in the tartaric acid content. An optimization procedure was also carried out by heating the reaction mixture at 175° C. for 4 hours in the presence of nitrogen and further curing at 195° C. for 5 hours. This method produced a much higher percentage of gel fraction as compared to the non-optimized procedure. Large scale reactions via this method were also carried out using 15 and 25 mol % of the crosslinker. The yields and % gel fractions were found to be higher for the polyester containing 25 mol % tartaric acid. Similarly, the glass transition temperature and 5% weight loss were found to be higher for the crosslinked polyester containing, 25 mol % of tartaric acid as shown in Table V.

The present invention relates to the use of optical waveguides to excite total internal reflectance for measuring dissolved-ammonia. It was determined that the key design issue in increasing the performance of total internal reflectance-based sensors is the evanescent field overlap with the light propagating in the waveguide. For example, depositing a 12 nm thick absorbing layer on an optical waveguide formed from eight microns thick silicon dioxide with phosphorous impurities on a silicon dioxide buffer layer on silicon substrate provides a power attenuation in one millimeter that is approximately one-half that observed by measuring the attenuation of light passing directly through the 12 nm thick layer.

In contrast, decrease of the waveguide thickness to one micron and use of a polyimide waveguide can provide an increase in power attenuation in one millimeter by 45 times that achievable by transmission of the light through the absorbing film. Key to achieving these improvements in sensor response is the reduction of the optical power carried by the substrate. Calculations on the use of a D-shaped fiber for absorption monitoring provided intermediate results. A polyimide waveguide was used to serve as a support for bromothymol blue in poly(ethylene maleate). Preliminary results indicated substantial reduction in the transmission of the waveguide after exposure to ammonia vapor. The waveguide-based sensor responded reversibly to ammonia vapor in that the optical transmission through the waveguide increased to the original value after the ammonia was removed.

Initial consideration of the system components has indicated that frequency division multiplexing was more suitable than wavelength-division multiplexing. Wavelength-division multiplexing is not applicable when using multiple sensors having the same excitation and emission characteristics as it is not possible to discriminate signals from individual sensors located throughout the facility. Therefore, a modified frequency-division multiplexer was developed.

Optical sensors could be developed for dissolved-oxygen, dissolved-ammonia and nitrate. A dissolved-oxygen sensor system and a reversible sensor for dissolved-ammonia based on molecular self assembly were demonstrated. Two dissolved-oxygen sensor packages were developed including a multiplexed sensor system for facility wide monitoring and a single-point, stand-alone oxygen sensor.

Fairly stable sensors for dissolved-oxygen can be developed using ruthenium complexes attached to the end of a multimode optical fiber. The output of the sensors was further stabilized using a Fourier transform signal processing technique. This technique allowed the detection of the dissolved-oxygen level even in the presence of stray light. The ammonia was able to distinguish ammonium hydroxide in water at $10^{-7}$M concentration from the same analyte in water at $10^{8}$M concentration. This represents a lower limit of detection for dissolved-ammonia on the order of 10 parts per billion. The detection of $10^{-7}$M ammonium hydroxide in water using a multilayered thin film optical chemical sensor represents an advance in the state-of-the-art in chemical sensor development.

Calculations on the use of the multilayered self-assembled thin film as a coating for a singlemode waveguide indicate that further increased sensitivity can be obtained. A nitrate-sensitive thin film was also demonstrated. This film showed sensitivity to $10^{-5}$M nitrate and response time of approximately one minute.

Conclusions drawn from this program can be divided into four areas: (a) the selection of fluorescent and absorbing indicator materials, (b) polymeric matrices for optical fiber sensors, (c) sensor geometry and electrical and optical integration, and (d) demonstration of the sensors in aquacultural process conditions.

Optical fiber sensors based on ruthenium (11) tris (4,7-diphenyl-1,10-phenanthroline) (Ru(Ph$_2$phen)$_3$Cl$_2$) are able to detect dissolved-oxygen and sensors based on the use of bromocresol purple (BCP) immobilized in poly (allylamine) (PAA) polystyrene sulfuric acid (PSSA) self-assembled thin films are able to detect dissolved-ammonia. In particular, it was found that Ru(Ph$_2$phen)$_3$Cl$_2$) was extremely sensitive to dissolved-oxygen in the range from 2.0 to 6.0 ppm of interest in preventing fish illness or kill. When the sensor based on Ru(Ph$_2$phen)$_3$Cl$_2$ was operated continuously for 24 hours, the dye exhibited some degree of photobleaching. The sensor could be operated in a non-continuous mode for an extended period of time if the oxygen level were measured once in a 10–20 minute period. Other conclusions concerning the selection of fluorescent and absorbing indicator materials are listed below:

Oxygen sensors based on Ru(Ph$_2$phen)$_3$Cl$_2$) can be excited using a light-emitting diode and operated repeatably over a period in excess of two weeks.

Fluorescence decay can be used to measure dissolved-oxygen concentration with accuracy equal to or exceeding that obtained with fluorescence intensity measurements.

A wide variety of fluorescent materials was sensitive to ammonia when immobilized in Nafion coatings. These materials responded irreversibly to the presence of trace quantities of ammonia, but could be used as an alarm or cumulative monitor of exposure to ammonia.

The polymer matrix chosen in the use of absorbing and fluorescent indicators to measure the concentration of dissolved-oxygen, dissolved-ammonia and nitrate is important. Silicone rubber was found to be an excellent matrix material for use with ruthenium metal complexes in the detection of dissolved-oxygen. Sensors fabricated from ruthenium complexes immobilized in sol-gel-deposited silica matrices did not perform as well as a result of the reduction of diffusion of oxygen into the film.

Films having decreased diffusion rates exhibited partial quenching of the immobilized fluorophore as a result of the oxygen concentration gradient set up in the film with reduced oxygen transport. Self-assembled multilayer thin films fabricated from alternating polyanionic and polycationic polymers could be sensitive to dissolved-ammonia. The use of an ultra thin film of thickness on the order of 12 nm to discriminate ammonium hydroxide in water at $10^{-7}$M concentration from the same analyte in water at $10^{-8}$M concentration indicates the value of this technique. Also, Teflon could be used to protect a self-assembled multilayer containing an absorbing dye from leaching when the multilayer is immersed in water. Other conclusions concerning polymer matrices for optical fiber sensors are listed below:

Multilayers of polystyrene sulfonic acid (PSSA) and polyallamine (PAA) can be deposited on silanized glass.

Indicator materials such as bromocresol purple (BCP) can be incorporated in PAA for development of ultrathin chemically responsive coatings.

Thin coatings of Teflon can be deposited onto self-assembled multilayers comprised of PSSA and PAA. The resulting Teflon-coated film is somewhat resistant to attack by water samples having high ionic strength.

Chemically sensitive thin absorbing films can be used to detect trace quantities of chemical analytes in solution.

Biodegradable polymers with a range of rates of hydrolysis can be designed using poly(lactic acid).

Considerable effort was used to evaluate optimal sensor geometries. The availability of light-emitting diodes (LEDs) with emission wavelengths suitable for excitation of fluorescent metal complexes for dissolved-oxygen detection provided impetus to investigate multimode optical fiber configurations for dissolved-oxygen measurement.

Prototype sensors were designed based on the use of two optical fibers for transverse excitation and collection of fluorescence, and these prototype systems provided considerable sensitivity to dissolved-oxygen concentrations. Low-cost digital signal processing techniques could be used to increase the precision of data obtained from optical chemical sensors. The use of a digital Fourier Transform Technique to filter extraneous noise sources from the chemical sensor provided increases in signal-to-noise ratio of one or two orders of magnitude under optimal test conditions, and larger increases in signal-to-noise ratio under conditions where stray light might interfere with signal detection. Additional conclusions concerning sensor geometry and electronic and optical integration are as follows:

The intensity output of optical fiber sensors depends on the bend radius of the fiber.

A ratiometric technique employed during the Phase 11 program using a dichroic filter to separate signal and reference channels and digital Fourier transform filtering methods, reduces the effect of fiber bending on the sensor signal from 120% of the total signal to 2 to 3% of the total signal.

Interference from stray light emanating from fluorescent lamps can be almost entirely eliminated using fast Fourier transform digital filtering.

A demonstration of the optical fiber sensor system under field conditions showed the effects of fouling and temperature on sensor response. The sensors were operated in aquaculture tanks for two weeks. The silicone-based sensors were found to exhibit little or no biological fouling after a two-week period. It was determined that the sensor was amenable to periodic evaluation of the dissolved-oxygen in the tank with little or no change in response over the two-week period. Additional conclusions are as follows:

There is a need for further study of the photodegradation process in metal complex fluorophores. It was determined that Ru(Ph$_2$phen)$_3$Cl$_2$) would photodegrade significantly after 24 hours of continuous use with a bright (1.0 mW) blue light-emitting diode.

Reduction in duty cycle or in excitation light intensity will extend the operational life of the sensor system.

The present inventions are thin-film sensor materials for optical measurement of dissolved-oxygen, dissolved-ammonia and nitrate concentrations. Bright light-emitting diodes (LEDs) with outputs in the range from 430 nm to 480 nm are available. These LEDs allow excitation by low-cost semiconductor diode lasers and permit the design and fabrication of several compact chemical sensors for dissolved and gaseous oxygen.

Work was performed to evaluate optimal fluorophore materials for use in an optical oxygen sensor. Transition metal complexes, such as ruthenium (II) tris(bipyridyl) (Ru(bpy)$_3^{2+}$) dichloride and ruthenium (II) tris (4,7-diphenyl-1,10-I phenanthroline) (Ru(Ph$_2$phen)$_3$Cl$_2$), can be used to form excellent sensors for dissolved-oxygen concentration. Of these two candidate materials, Ru(Ph$_2$phen)$_3$Cl$_2$ exhibited the largest change in fluorescent intensity throughout the range of dissolved-oxygen concentrations of interest in the evaluation of aquacultural water quality.

The optical response of the fluorescence-based sensors for dissolved-oxygen follow a Stern-Volmer relationship between concentration and fluorescence, as opposed to the linear response between concentration and voltage exhibited by Clark-type electrochemical sensors. However, the sensitivity of the fluorescence-based sensor is typically higher at lower dissolved-oxygen concentrations than that obtained using the Clark electrode. This is attributed to the high oxygen permeability of the silicone rubber matrix used for the sensors. The use of silicone rubber as the matrix for the metal complex fluorophore was also advantageous in reducing the buildup of biological fouling on the sensor.

Absorbing indicator materials that could be used to detect dissolved-ammonia at concentrations of interest in aquacultural facilities were evaluated. This was accomplished through the use of molecular self assembly to fabricate ultrathin organic multilayer films containing bromocresol purple (BCP).

Three methods were considered for molecular self assembly of multilayer structures. The first method involves the deposition of ordered films by alternately adsorbing tetravalent or trivalent metal ions and α, ω bis-phosphonic acids from aqueous solution. The films can be prepared on gold or silica surfaces. This method was extended to the deposition of multilayer films from zirconium and hafnium phosphonates. The second method involves the deposition of an ω-mercaptoalkanecarboxylic acid on a clean gold surface followed by exposure of the surface to Cu(ClO$_4$)$_2$ in ethanol. The third method involves alternate version of the substrate in solutions containing either a amphiphile (long molecules with charges at both ends) or a polymer electrolyte. This procedure produces alternate layers having opposite charges.

A variation of this method, which uses polymer electrolytes in place of amphiphiles, is particularly promising as a means of developing high quality, multiple-layer films containing chemically specific materials. Consequently, this modified method was selected for building multiple thin film layers in this research program. The sensors produced from multilayers of poly(styrene sulfonic acid) (PSSA) and poly-allylamine hydrochloride (PAA), and coated with a thin layer of Teflon exhibited unparalleled sensitivity to changes in dissolved-ammonia concentration.

The sensors responded rapidly and were reversible when brought into the presence of solutions containing varying concentrations of ammonium hydroxide. The rapid sensor response with decreased membrane thickness is consistent with results reported in the literature, which found that the response time depended upon the square of the membrane thickness. A wide range of indicator dyes and immobilization matrices was evaluated, but only sensors based on molecular self-assembled thin films demonstrated the ability to detect dissolved-ammonia concentrations below 40 parts per billion.

The synthesis of poly (L-lactic acid) and poly(D,L lactic acid). Degradable polyester polymers were synthesized via polycondensation of L-lactic acid in the presence of tartaric acid as a crosslinking agent. Crosslinked polyesters prepared in this way were immersed in phosphate buffer and the weight loss monitored to estimate the extent of hydrolytic cleavage or degradation occurring over time. It was found that the weight loss was significantly slowed by increased crosslinker concentrations in the polyester. Films containing 15% tartaric acid exhibited exponential weight loss with time, whereas films with 25% tartaric acid exhibited linear weight loss with time. After 200 hours, the weight loss due to hydrolytic cleavage of the poly(lactic acid) containing 15% tartaric acid was almost double that observed for polyesters containing 25% tartaric acid.

Differing sensor geometries were evaluated to determine the sensor configuration showing the largest signal-to-noise ratio. Results indicated that transverse configuration of excitation and detection optical fibers provided enhanced signal-to-noise ratio over single fiber configurations.

The present invention is a time division multiplexing system for optical sensing of dissolved-oxygen in aquaculture facilities. Work was also performed to develop a digital signal processing approach to the reduction of stray-light interference in optical fiber chemical sensors and to apply time division multiplexing to the detection of fluorescence decay from multiple sensors.

The results demonstrated the use of a simple multiplexing system to collect data on dissolved-oxygen from multiple tanks in an aquaculture facility. The costs associated with the 1×4 multimode multiplexers were minimal, allowing reduced operator labor in gathering data throughout the facility. It is expected that these findings can be applied to the monitoring and control of water and wastewater treatment plants and to other biotechnological processes, such as biological fermentation where dissolved-oxygen concentration is critical. It may be noted that work performed by Dr. Lakowicz at the University of Maryland at Baltimore indicated that ruthenium fluorophores immobilized in silicone rubber matrices could be autoclaved at 120° C. for 40 minutes without significant reduction in sensitivity or accuracy.

The present invention is a multiplexed optical chemical sensor system at an aquaculture facility. The sensors brought to the closed-cycle aquaculture research area of Virginia Polytechnic Institute and State University (VPI & SU) responded to diurnal changes in oxygen levels resulting from an increase in fish respiration during daylight hours and decreased respiration rates at night. The demonstration provided proof that the sensors could be used for the intended application and that the sensors performed reliably with the exception of one sensor which failed after 5 days of use.

The demonstration at VPI & SU indicated a need for improvements in sensor packaging to reduce heat buildup during sensor operation. A key finding of the demonstration at VPI & SU was that little or no fouling was evident on the surface of the probe material used in the sensor after two weeks of operation in the aquaculture facility. It is possible that the hydrophobic nature of the silicone used in the Phase II sensor reduced microbial adsorption, and thereby reduced sensor fouling.

The present inventions are several prototype sensors for measuring dissolved-oxygen concentration in a closed-cycle aquaculture facility and a digital signal processing (DSP)-based instrument for improving the signal-to-noise ratio of the prototype fluorescent sensors. Prototype sensors using transverse optical fibers for fluorescence excitation and detection were improved through the application of DSP to reduce the effects of bending losses in optical fibers. The DSP-based instrument is low in cost and can increase the precision of fluorescence measurements by one or two orders of magnitude through signal averaging and through reduction of the effects of external interferences, such as stray light and changes in the orientation of the optical fiber sensor during analyte measurement. The ratiometric approach used successfully is an extension of simple referencing techniques.

In the present invention, the Fourier transforms of the modulated signal from the LED and from the sensor probe are divided to allow a convenient reference for chemical sensor applications.

The present inventions represent substantial advances in the state-of-the art in optical chemical sensing. In particular, the demonstration that ultrathin self-assembled thin films having immobilized optical absorption indicators can be used to detect 10 parts-per-billion dissolved-ammonia is a major breakthrough in efforts to produce low-cost sensors for analytes at trace concentrations. Low-cost instrumentation using digital signal processing to improve the signal-to-noise ratio of optical fiber chemical sensors, is crucial to the eventual acceptance of optical methods of chemical analysis in industrial settings.

The present inventions can be optimized to provide signal averaging, Fourier transform signal filtering and noise reduction and fluorescence decay analysis with a single system. The digital signal processing instrument developed will have particular application in optimizing the performance of optical absorption-based instrumentation. The poly(lactic acid) coatings developed are expected to prove useful for both electrochemical and optical chemical sensors through reducing the effects of biological fouling on chemical sensor membranes.

These and further and other objects and features of the invention are apparent in the disclosure, which includes the above and ongoing written specification, with the claims and the drawings.

BRIEF DESCRIPTION OF THE DRAWINGS

FIG. 3 is a front elevation of excitation of dye entrapped at the end of an optical fiber.

FIG. 4 is a front elevation of ruggedized setup for fabricating fiber-optic probe with dye-doped thin film attached to end of an optical fiber.

DETAILED DESCRIPTION OF THE DRAWINGS

Figure 1:
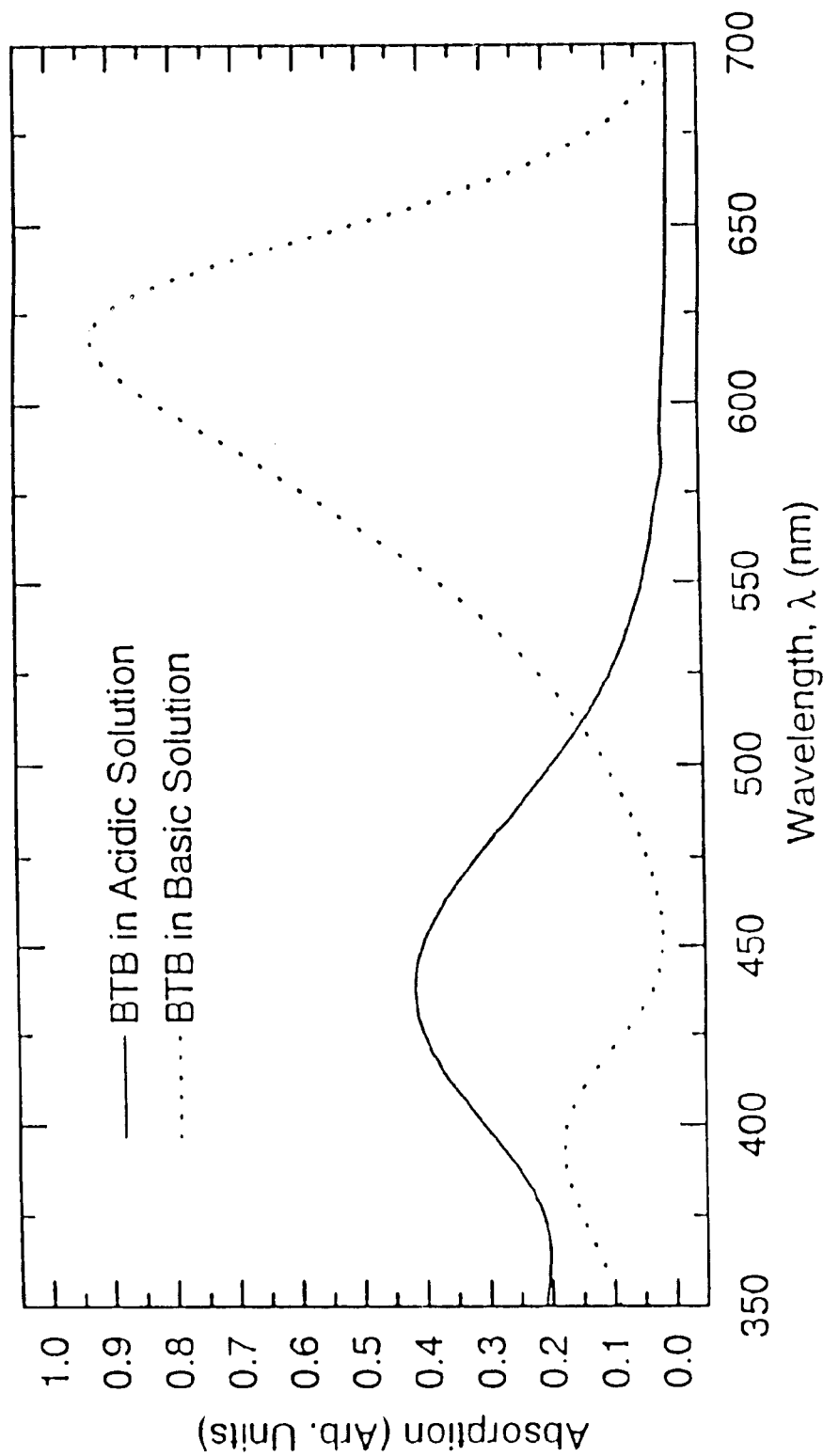
FIG. 1 is a graph showing adsorption of bromothymol blue in acidic and basic solutions.

FIG. 1 shows a graph of the dye in acidic and basic solutions. Upon interaction with ammonium hydroxide, the dye molecule undergoes a change in absorption spectrum as shown in FIG. 1. In acid media, the BTB molecules are orange in color and have their absorption spectrum at around 480 nm. In basic media the dye is dark blue and absorbs strongly near 630 nm wavelength. That change in absorption spectrum is best detected by the use of a red light source, such as a helium-neon laser emitting at a wavelength of 633 nm or a laser diode emitting at 645 nm.

Figure 2:
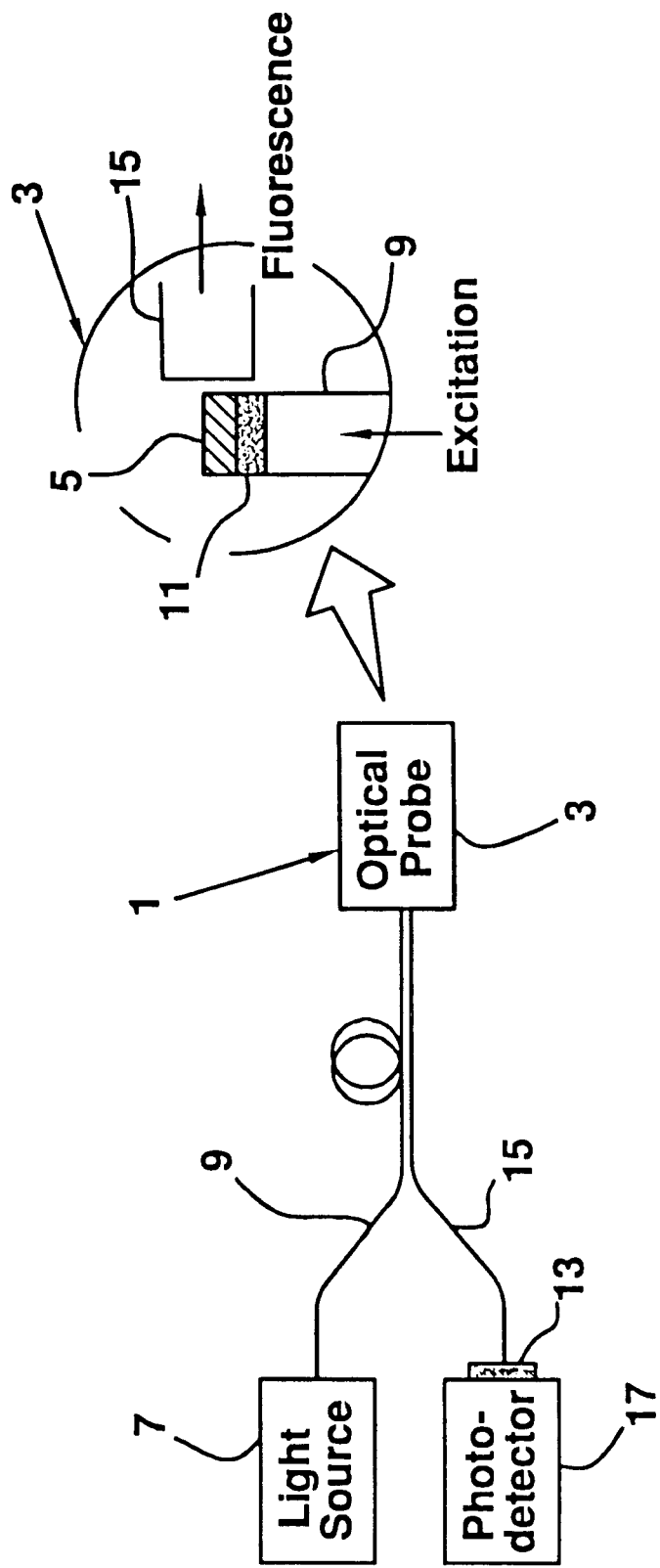
FIG. 2 is a front elevation of transverse excitation and collection of fluorescence signals.

FIG. 2 shows a front elevation of a type H sensor 1. Work was performed to determine the performance of transverse excitation and collection of fluorescence signals from dyes immobilized in polysiloxane and sol-gel films 3. The excitation and detection geometry is shown in FIG. 2. The light sources 7 being used in this configuration include lasers or light-emitting diodes (LEDs) depending on the dye being used. The excitation light was launched into a 1 mm diameter plastic optical fiber 9, and the dye was excited through a short-wavelength-pass filter 11 when an LED was being used.

The detection fiber 15 was attached side-on to the dye-doped film 5, and the fluorescence signal was detected by a high-gain amplifier/detector combination 73, 17 or a low noise avalanche photodetector package (Hamamatsu Model C4551-4) 17. A long-wave-length-pass filter 13 was implemented in front of the photodetector 17 to eliminate influence from the excitation light.

A second approach involved attachment of a dye-doped thin film 5 at the distal end of optical fiber tips 21. FIG. 3 shows a schematic of the experimental setup. The oxygen-sensitive dye, Ru(bpy)$_3^{2+}$ in sol-gel was deposited at the end of a one-meter fiber 21 having core and cladding diameters of 100 and 140 µm, respectively. The other end of the fiber was connected to the source fiber 29 using a mechanical splice 27. An argon laser 7 emitting at 488 nm wavelength was used as the source of excitation, and the laser light was injected to the source fiber 29 through a 900 beamsplitter 23 and focused with a microscope objective 25. The fluorescent light was captured and was directed back to the source fiber 29 through the beamsplitter 23, was focused with a lens 31 and was recorded using an optical multichannel analyzer 33.

Work was also performed to use optical fiber components to reduce bulk optical components, such as the laser 7 and the beamsplitters 23. In the event that the fluorescence spectrum has a large Stoke's shift, a setup shown in FIG. 4 can be used to excite and detect fluorescence with a dye-doped thin film 5 attached to the end of a fiber 29. In this configuration, the emission from the LED 7 was launched into an 1 mm optical fiber 9 through a short-wavelength-pass filter (Corion) 11. The short-wavelength-pass filter 11 is polished down to a thickness of 100 µm in order for maximum coupling of the excitation light into the fiber. The excitation light was launched into one fiber end 9 of a 2×1 fiber coupler (American Laubscher Corporation, Farmingdale, N.Y.) 35. The excitation and fluorescence light was transmitted and collected using the same fiber 29 as shown in FIG. 4. The fluorescence light was detected by a photodetector 17 through a fiber 15 connected to the output port of the 2×1 fiber coupler 35. This configuration has the advantage of simple setup, and simple construction of the Type H fiber-optic probe 21 and sensor 19.

Figure 5:
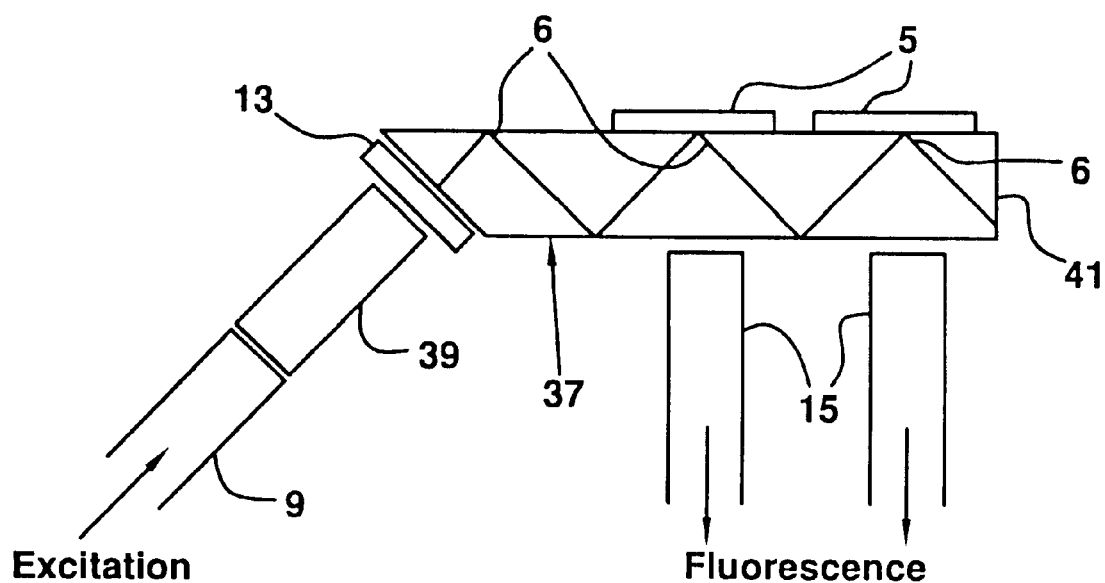
FIG. 5 is a front elevation of evanescent wave excitation of transverse collection of fluorescence signals.

FIG. 5 shows the geometry of a fiber-optic sensor probe using an evanescent wave excitation technique 37. In this geometry, the excitation light is first collimated using a graded-index lens (GRIN) 39, and then launched through a filter 12 into a beveled substrate 41. The presence of a filter 12 enables the use of an achromatic light source 7, such as an LED, to excite fluorescence. A beveled substrate 41 allows for efficient coupling of the excitation light into the substrate 41. The advantages of this setup are very low Rayleigh scattering from the thin film 5 and provision of multiple sensing regions 6 on the same substrate. This optical probe structure 37 was fabricated to detect ammonia.

Figure 6:
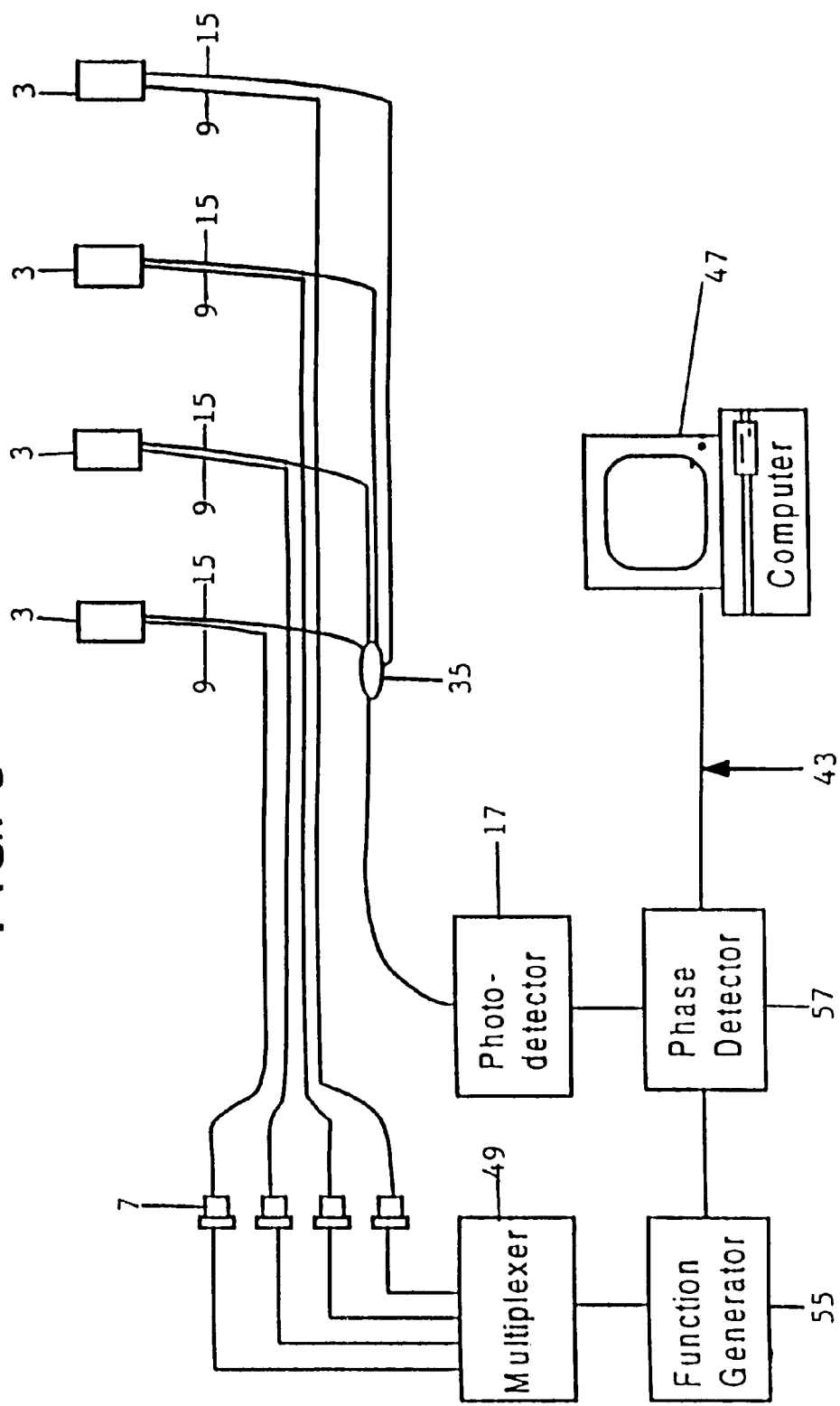
FIG. 6 is a flow chart of system architecture for optical multiplexing of sensor network.

Work was performed to design and fabricate a multiplexed fiber-optic oxygen sensor system 43 suitable for installation in an aquaculture network facility. FIG. 6 shows a schematic of the multiplexed sensor system 43 consisting of multiple sensor probes 3, a light source 7 and fluorescence detection unit 17, lock-in amplifier 45 and a computer 47 for control and data processing. The optical probes 3 were fabricated as described above.

The light sources 7 used for excitation were the bright blue LEDs (Nichia America) emitting at center wavelength of 450 nm and intensity of approximately 1 mW at 20 mA of driving current. Two approaches for multiplexing 49 were possible. The first approach was to use different oscillator circuits 51 for each individual LED so that all the LEDs were turned on simultaneously.

Alternatively, one oscillator 51 can be used for the multiplexing scheme 49 and the LEDs turned on sequentially. The latter approach was selected in order to reduce the number of electronic components. The oscillator circuit 51 provided a 100 kHz square wave which was used to drive the LEDs sequentially by a demultiplexer circuit 53. The demultiplexer circuit 53 provided control to address individual LEDs by a computer. The LED light sources 7 in the multiplexed fiber optic sensor system 43 were modulated at a frequency of 100 kHz. Using this modulation frequency, environmental noise, such as ambient light and electrical noise from power equipment is effectively suppressed.

The excitation light was launched through the optical fiber 9 to excite the fluorophores in the polymer thin film 5. The fluorescent signal was collected and led back to the fluorescence detection unit 17. The fluorescence from different sensor probes 3 was multiplexed into one fiber through the use of a 1×4 fiber coupler (American Laubscher Corporation, Farmingdale, N.Y.) 35, and it was detected using an avalanche photodiode 17. A long-wavelength-pass filter (Corion CS-500) 13 having a 50% pass edge at 520 nm wavelength was used to reject the residue LED light from the optical probes. The output signal from the photodetector was measured using a lock-in amplifier 45.

Work was also performed to develop a data acquisition and analysis software using a computer 47. The computer 47 was used as a data logger and an interface for connection to an HDCCA data network. The computer 47 is used to turn on specific sensors acquire the fluorescence signals and analyze the results, and store the data on the system hardware memory. The software provides a time stamp in the data stream and an autostart feature that automatically resumes data measurement even after a power interruption. After an event of power interruption, a power loss message will be appended to the data file, the system will re-initialize and data logging will resume. This multiplexed system was installed and used in an HDCCA facility to measure the oxygen levels in several locations in the facility as described below.

Figure 7:
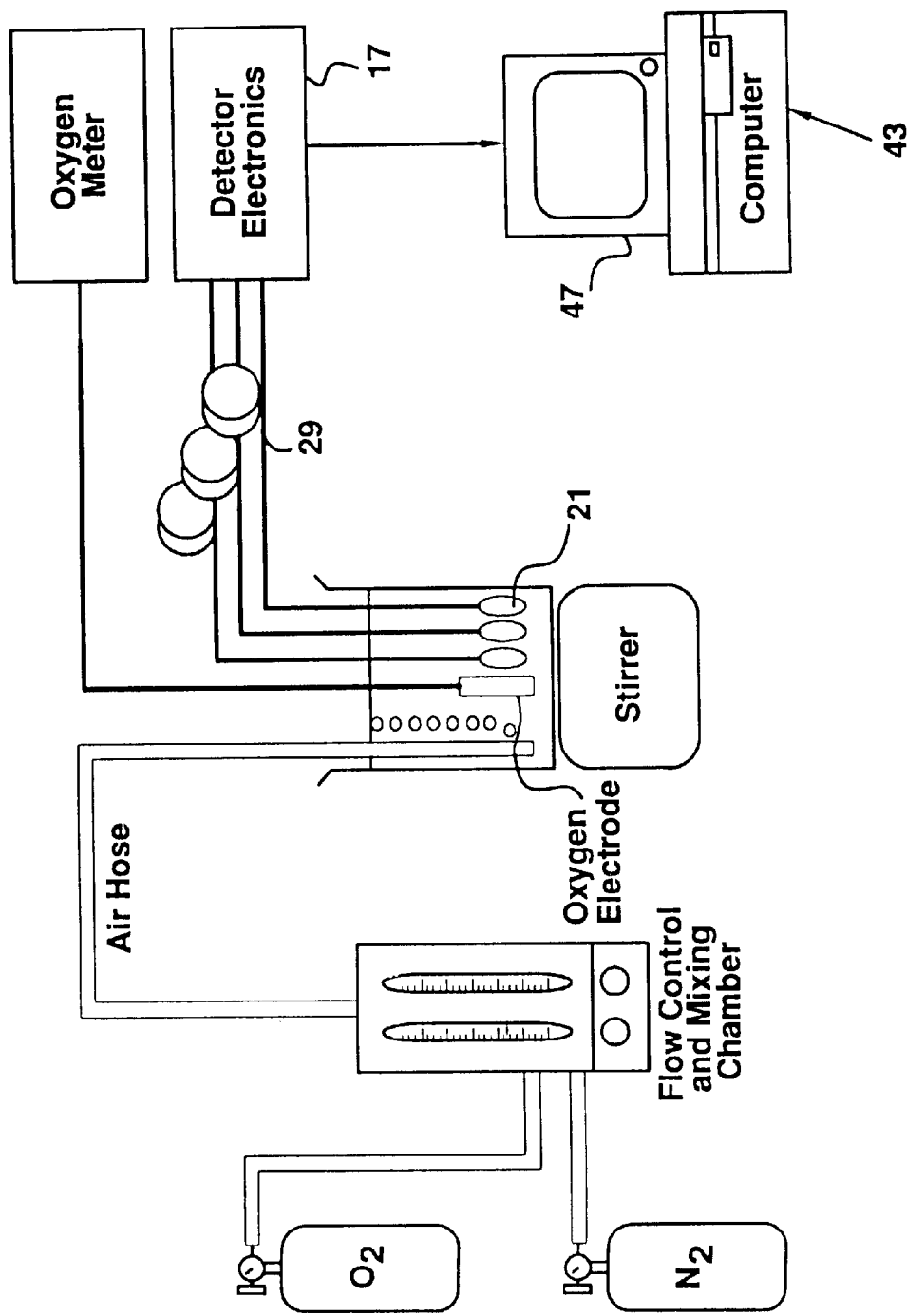
FIG. 7 is a front elevation of system architecture for calibration of multiplexed fiber-optic sensors.

A calibration of the multiplexed fiber-optic sensor 43 was carried out using an experimental setup shown in FIG. 7. A mixture of nitrogen and oxygen gas was metered and was bubbled into a beaker containing water to create different concentrations of dissolved-oxygen. The fiber-optic probes 21 were submerged under water along with an oxygen electrode which was being used as the standard. The water in the container was stirred continuously to facilitate an accurate measurement of dissolved-oxygen by the oxygen electrode. Signals from the probes were sent to detector electronics 17 and then to a computer 47. The sensor response was repeatedly measured to provide a statistical representation of the accuracy of measurement by the sensor system.

Figure 8:
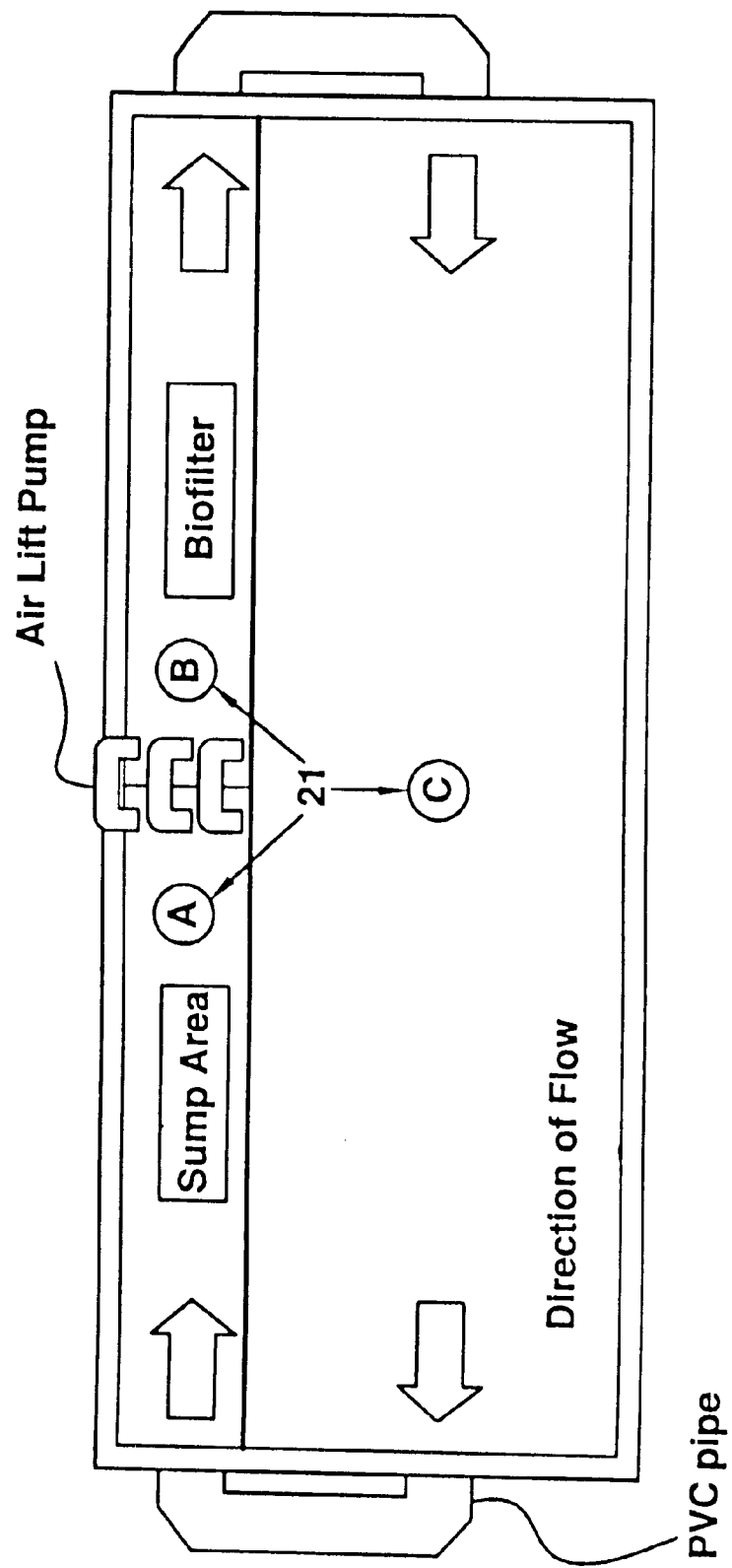
FIG. 8 is a top elevation of closed-cycle aquaculture facility and locations of sensors in the tank.

After the calibration of the sensor system, an experiment was carried out to demonstrate the use of the system in acquiring continuous dissolved-oxygen levels in an HDCCA facility at the Virginia Tech Aquaculture Center. The dimensions of the facility are 7.32 m×2.44 m×1.07 m(depth) and holds approximately 18700 L of water (FIG. 8). The tank was divided into three sections including the area where the fish are raised, a sump area for solid waste removal and a biofilter for nitrification. Several air lift pumps were used to enrich the water with oxygen and circulate water in the tank. The air lift pumps circulated approximately 389 liter of water per minute in the tank.

Tilapia (originated from Africa) was raised in the tank during the experimental period. They are hardy fish and can tolerate larger fluctuations in environmental conditions. There were 1800 fishes in the overall tank volume with specific regions assigned on the basis of fish size. The small fish weigh 4 g each and are approximately 3.8 cm long, whereas the large fish weigh 200 g and are approximately 15 to 17 cm long. The water temperature was kept at approximately 15° C.

The sensor system was installed strategically in three different locations (A, B and C) in the fish-raising tank (FIG. 8). Sensors A, B and C 21 were located at the sump area, the biofilter and main fish raising area, respectively. They are located in three different locations of the same tank instead of three different tanks because it was expected that the bioprocesses inside the tank would affect the dissolved-oxygen levels differently during a daily cycle. For example, the biofilter is expected to have a higher dissolved-oxygen level during daylight hours when algae produce dissolved-oxygen through photosynthesis. However, during the night, this area is expected to have a lower dissolved-oxygen level when algae are consuming oxygen.

The main fish raising area is expected to have a lower dissolved-oxygen level during the daytime when the fish are more active. The experiment was carried out for a period of 14 days. During the experiment, sensors A, B and C 21 were used to acquire dissolved-oxygen concentrations every 20 minutes. At the end of the experiment, the sensors were examined for their functionality as well as biofouling.

Figure 9:
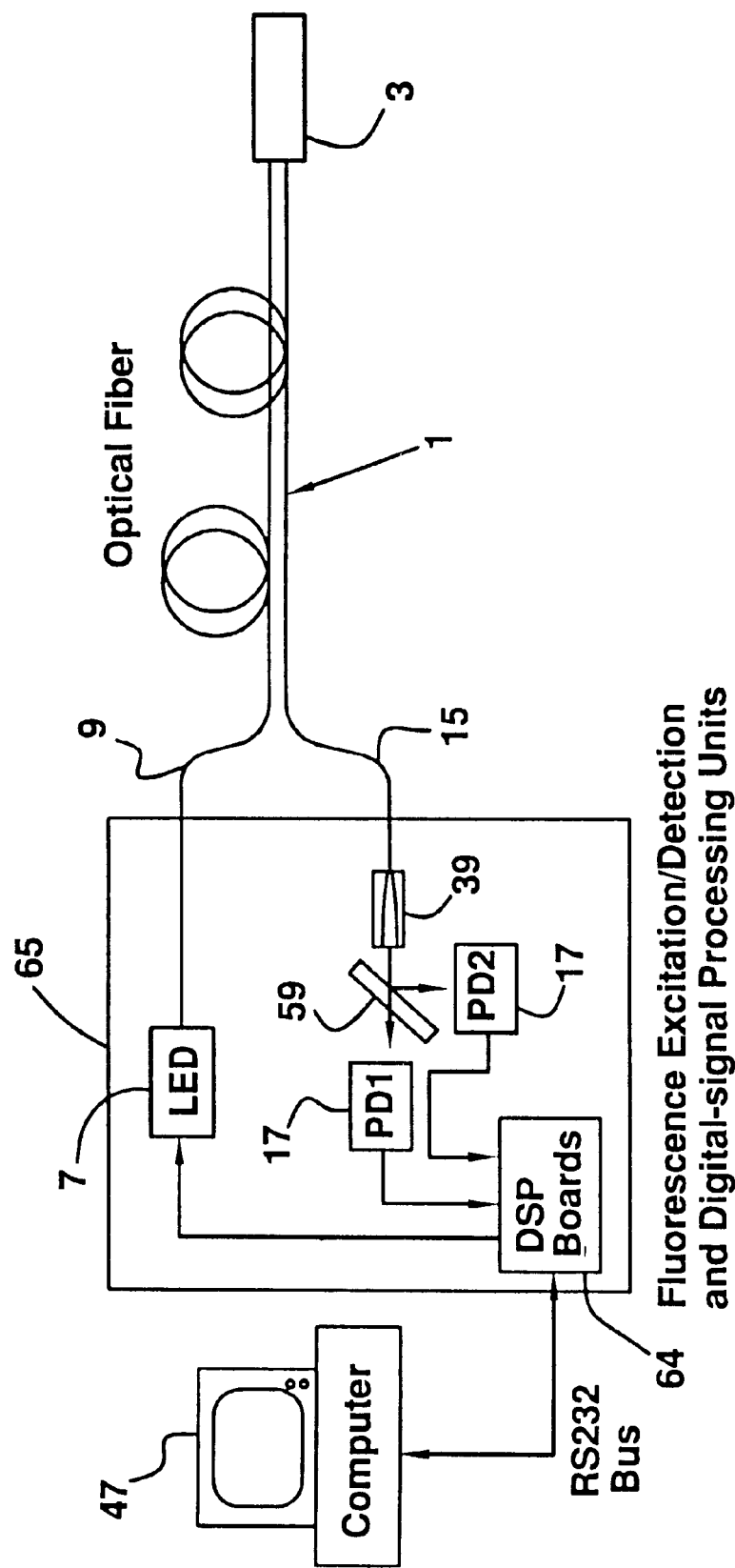
FIG. 9 is a flow chart of fluorescence intensity-based fiber-optic oxygen sensor.

Work was also performed to design an optical fiber sensor package to detect dissolved-oxygen levels. A schematic diagram of the fluorescence-based fiber-optic oxygen sensor 1 is shown in FIG. 9. The sensor system consists of an optical sensor probe 3, excitation light source and detection electronics 65, digital signal-processing electronics 64, a microcontroller and liquid-crystal display 47. The optical sensor probe 3 was fabricated according to the procedure detailed above. A bright blue LED (Nichia America, USA) 7 was used as the excitation light source. The excitation light was launched into a 1 mm-diameter plastic optical fiber 9, and the dye-doped film 5 was excited through a short-wavelength-pass filter (Corion) 11. The collection fiber 15 was attached side-on to the dye-doped film, and the fluorescence signal was transmitted by the fiber 15 to the detector assembly.

A graded refractive index (GRIN) lens 39 having 0.25 pitch was used to collimate the fluorescence signal and a yellow subtractive dichroic filter (Corion) 59 having cutoff wavelength at 550 nm was implemented to separate the residue excitation and fluorescence spectra. The two separated spectra were detected using two high-gain amplifier/detectors (Burr-Brown Model OPT201) 73, 17. Since an LED/photodetector combination was used, the total cost of the components can be less than $300. The size of the system configuration was minimal. Since no laser was used in the package, the light source 7 and detector 17 can fit into a package of dimensions 10×7×5 cm. Additional advantages of this oxygen sensor includes fast response time and no consumption of oxygen during measurement processes.

Figure 10:
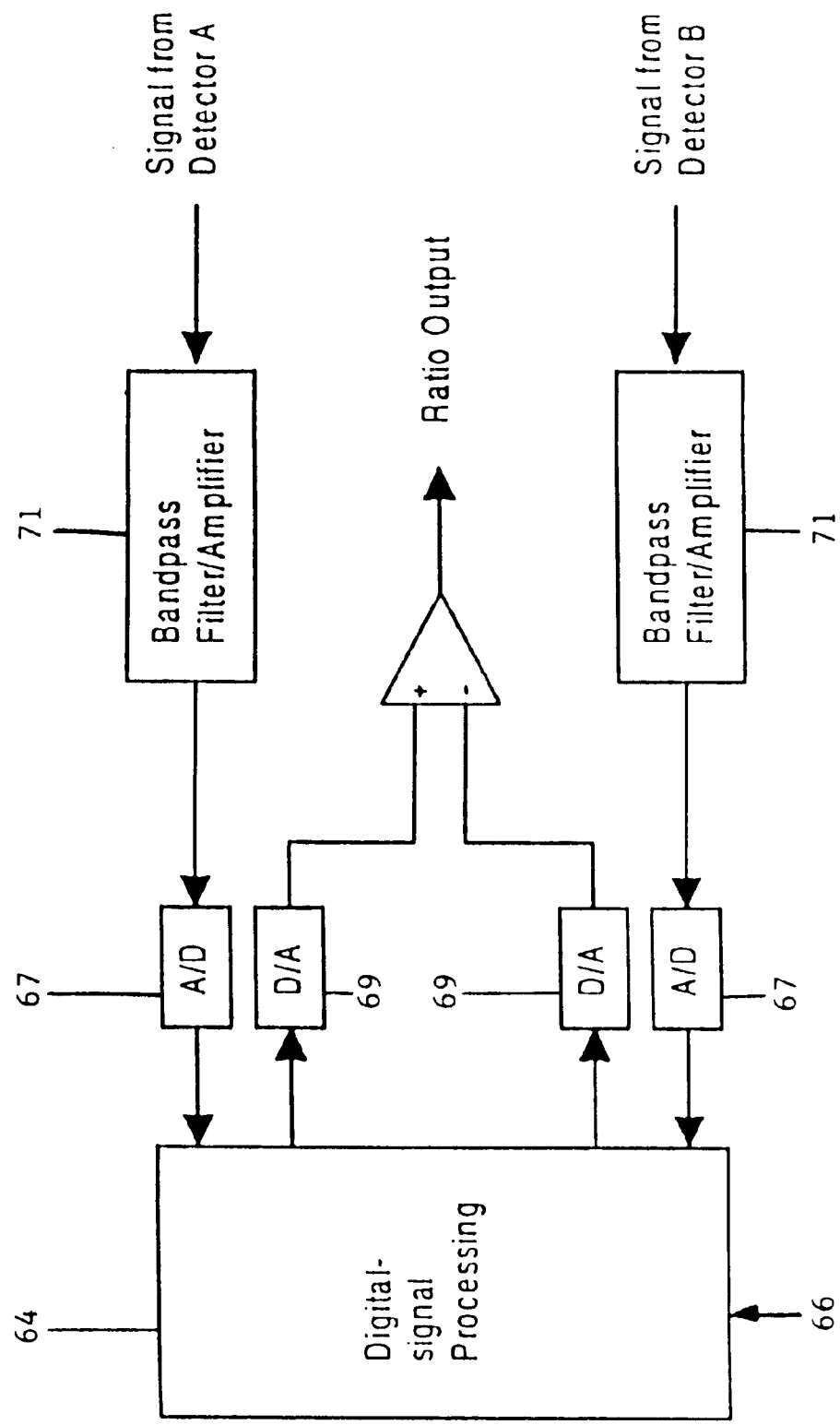
FIG. 10 is a flow chart of digital signal processing hardware.

A digital signal processing technique 66 was implemented for low-intensity fluorescence detection as well as for compensating optical fiber bending loss. The Texas Instruments TMS32OC26 DSP Starter Kit (DSK) 64 was employed as the heart of the sensor electronics. A simplified functional block diagram is shown in FIG. 10. The blue LED 7 was driven at approximately 1.1 kHz. The fluorescence and residue excitation signals were separated and detected as different channels. The signal for each channel was fed into a 4-pole Butterworth active bandpass filter 71 to reject interference noise signals from ambient light, and the analog signal was converted to a digital signal by the DSK onboard 12-bit analog-to-digital conversion interface circuit 67.

A 256 point complex FFT was used to convert the time-domain data to frequency domain data using a DSP chip. The frequency window at 1.1 kHz was selected and the remainder of the frequency data was set to zero. The resultant frequency spectrum was inverse fast Fourier transformed back to the time domain.

The ratio of the fluorescence and excitation channels can be carried out by utilizing the logarithmic outputs of the DSP chips. Channels A and B denote the logarithm of the outputs from the fluorescence signal and the excitation signal, respectively. The difference of the two channels:

$$\text{Channel A} - \text{Channel B} = \text{Log(Fluorescence)} - \text{Log(Excitation)} = \text{Log(Fluorescence/Excitation)} \quad (4)$$

thus, represents the logarithm of the ratio of fluorescence to the excitation signal. The difference of the two analog signals was implemented electronically using a unity gain difference amplifier circuit.

An experiment was carried out to demonstrate the ability of the ratiometric method to reduce the effect of bending loss in the optical fiber. An assumption was made that the attenuation of the signal due to fiber bending loss is independent of the wavelength of the propagating light.

Consequently, the attenuation resulting from fiber bending is the same for the fluorescence signal as for the signal from the excitation source propagating in the optical fiber. The experiment consisted of bending either the excitation fiber 9 or the collection fiber 15 around circular cylinders of specific diameters while the fluorescence signal was measured.

Figure 11:
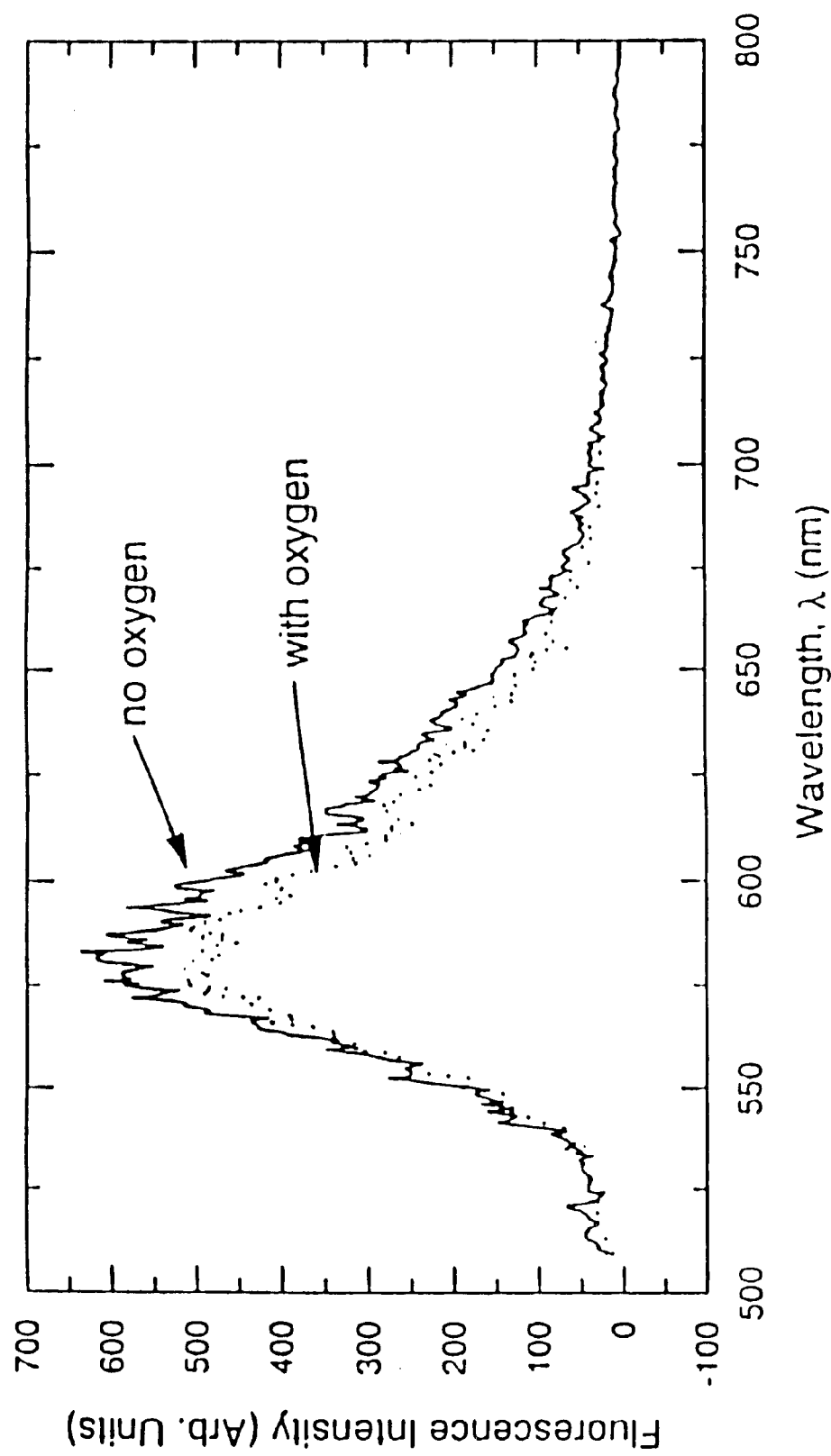
FIG. 11 is a graph of emission spectra of ruthenium tris(bipyridyl) dichloride dye in sol-gel in nitrogen and pure oxygen.

FIG. 11 shows a graph of the emission spectra of the film both in the absence and presence of oxygen. Table II summarizes the data on film thickness in relation to spin rate and the percentage of quenching efficiency in air, $I_{air}$, and pure oxygen, $I_{O2}$, relative to nitrogen, $I_{N2}$. It was found that when the spin-coating rate was increased from 1000 to 3000 rpm, the film thickness decreased from 12 μm to 6.2 μm, while the quenching efficiency in air doubled and the quenching efficiency in pure oxygen increased by 83%. The thinner the film, the greater the effect of quenching. When the film is thick, oxygen gas cannot diffuse deep into the film and interact with the entrapped dye. These dyes will fluoresce and the signal will mainly contribute to the background signal. Therefore, a lower quenching efficiency was observed.

Figure 12:
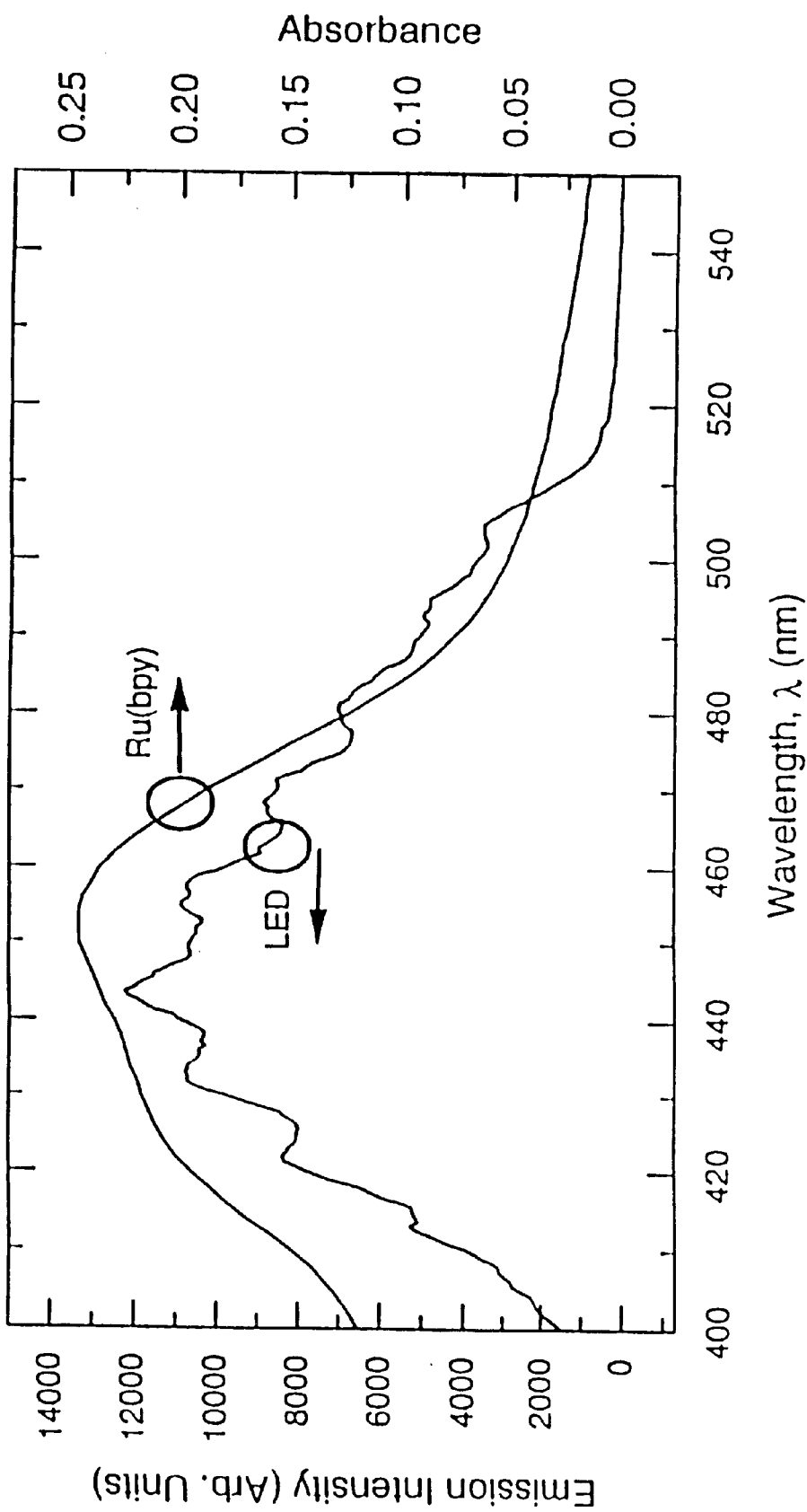
FIG. 12 is a graph of absorption spectrum of ruthenium tris(bipyridyl) dichloride and emission spectrum of blue light-emitting diode through 500 nm short-wavelength-pass filter.

FIG. 12 shows a graph of the absorption spectrum of $Ru(bpy)_3^{2+}$ (similar to $Ru(Ph_2phen)_3^{2+}$) in sol-gel glass matrices and the emission spectrum of a high-intensity blue LED (Nichia, Japan). This figure shows a large overlap in spectra indicating I—that the blue LED can be used for exciting the ruthenium complexes.

Experiments on the response of $Ru(Ph_2phen)_3Cl_2$-doped silicone rubber films to molecular oxygen were performed using an argon-ion laser as the excitation source. The fluorescence intensity of the ruthenium complex was measured using a photomultiplier tube (PMT). One fiber was used to direct the incident light to the film, while the other fiber delivered fluorescent light to the PMT. A long-pass filter (540 nm) was placed in front of the photodetector to block excitation light.

Figure 13:
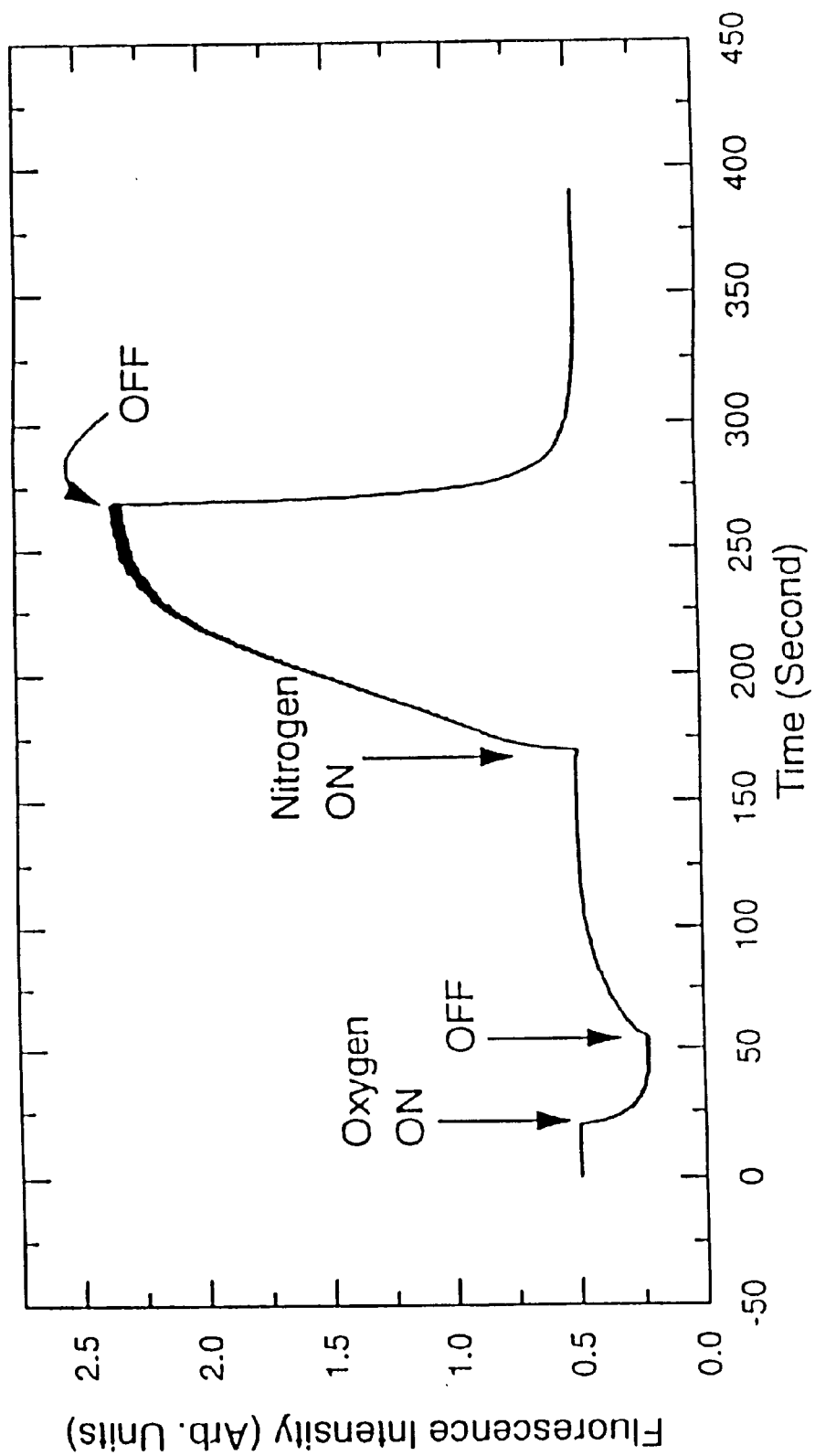
FIG. 13 is a graph of change of fluorescence for ruthenium complex in silicone exposed to oxygen and nitrogen.

FIG. 13 shows a graph of the changes in fluorescence when the film was exposed to various levels of oxygen. Quenching was most sensitive when the $O_2$ partial pressure was less than 10 percent. A total quenching efficiency of 90 percent was also observed in this figure.

Figure 14:
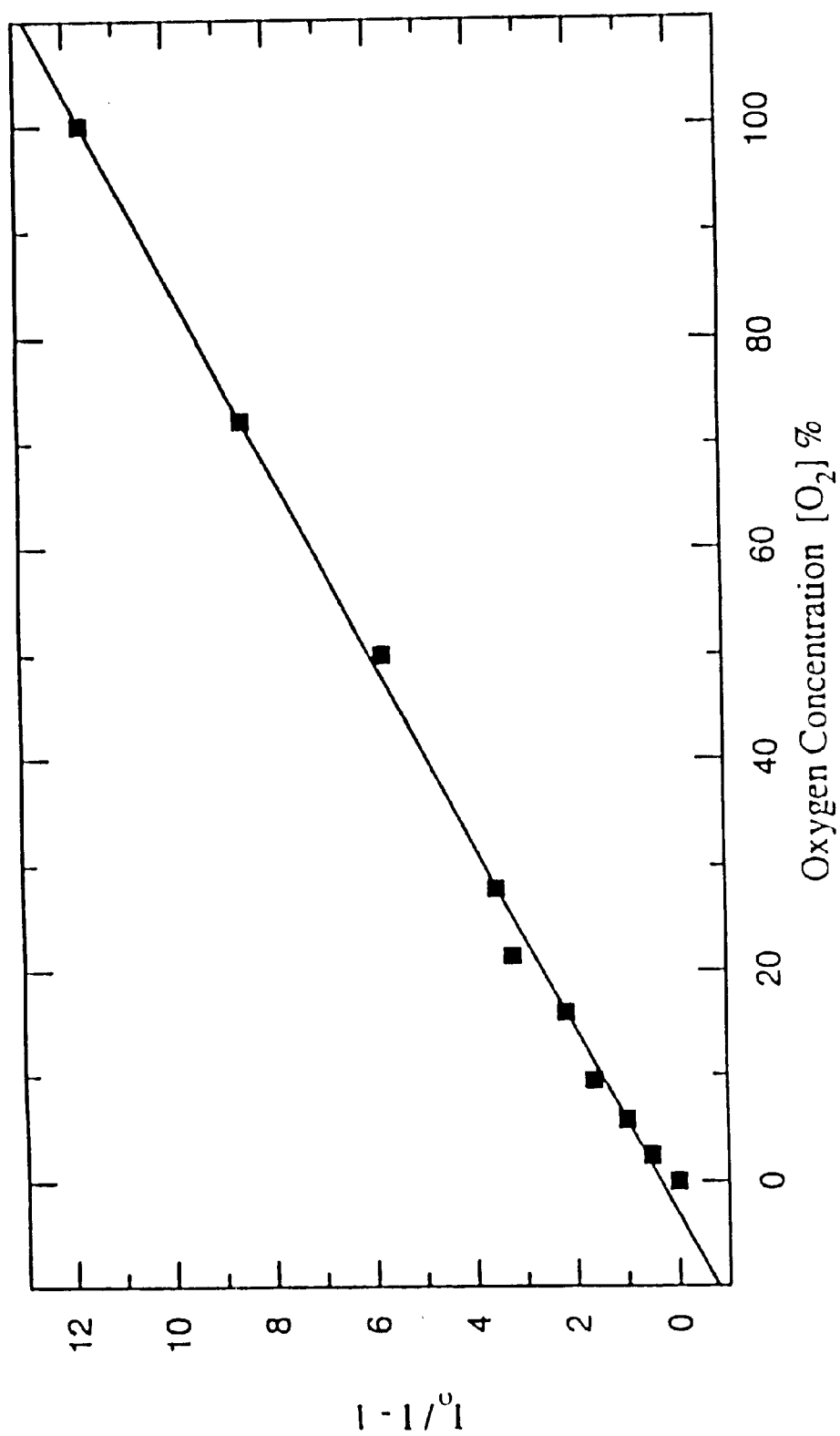
FIG. 14 is a Stern-Volmer graph of fluorescence intensity versus oxygen concentration.

Plots of $I_O/I$ or $I_O/I \times 1$ versus Q should be linear with identical slopes of K if $O_2$ is the only quencher. FIG. 14 is a plot of $I_O/I-1$ versus percentage of oxygen. It is linear over the entire oxygen concentration range, which means that the film thickness and the dye distribution are homogeneous. This oxygen sensor has been mounted in a device to be discussed later.

Figure 15:
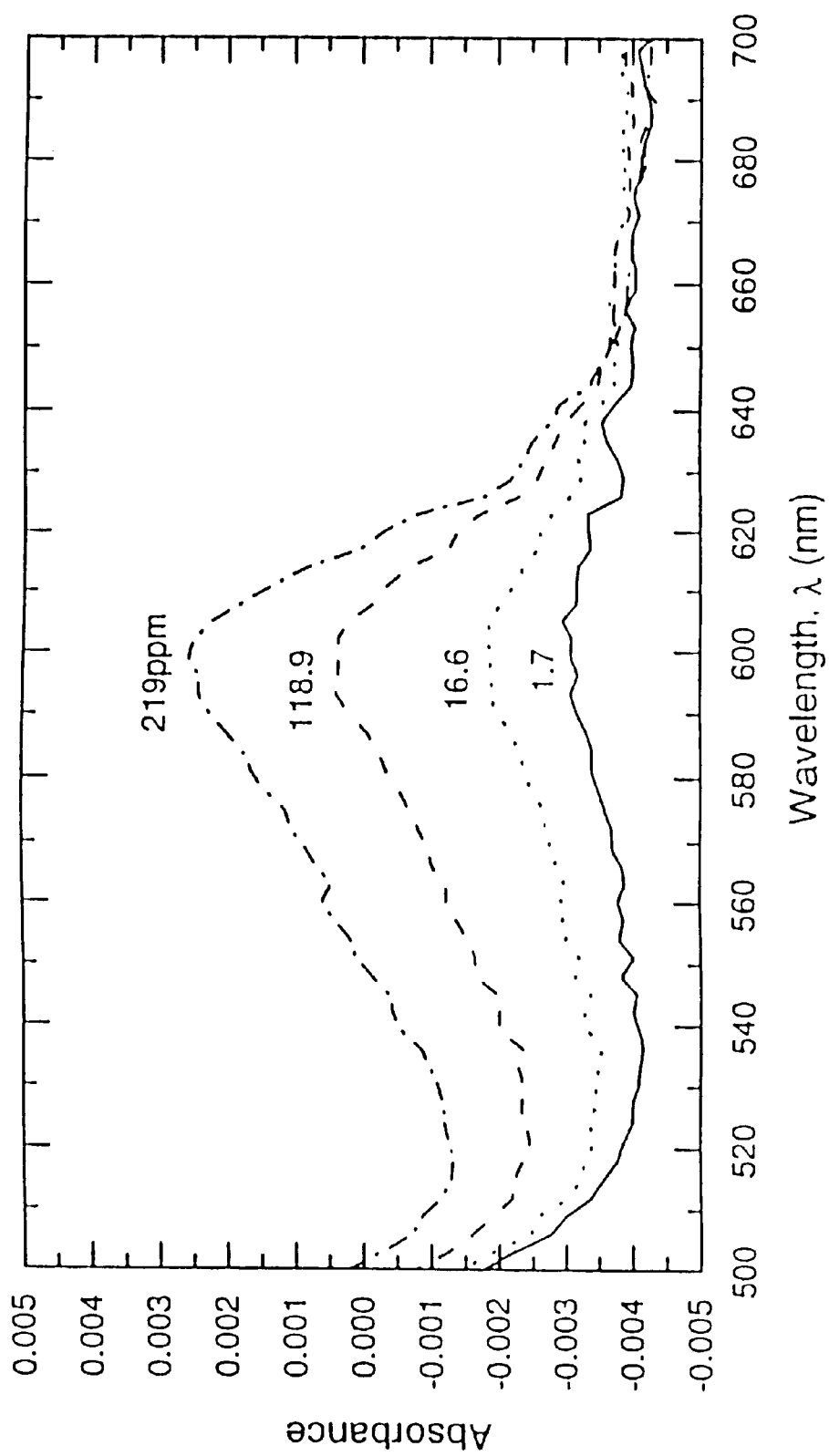
FIG. 15 is a graph of absorption spectra of bcp in cellulose acetate to various amounts of ammonia.
Figure 16:
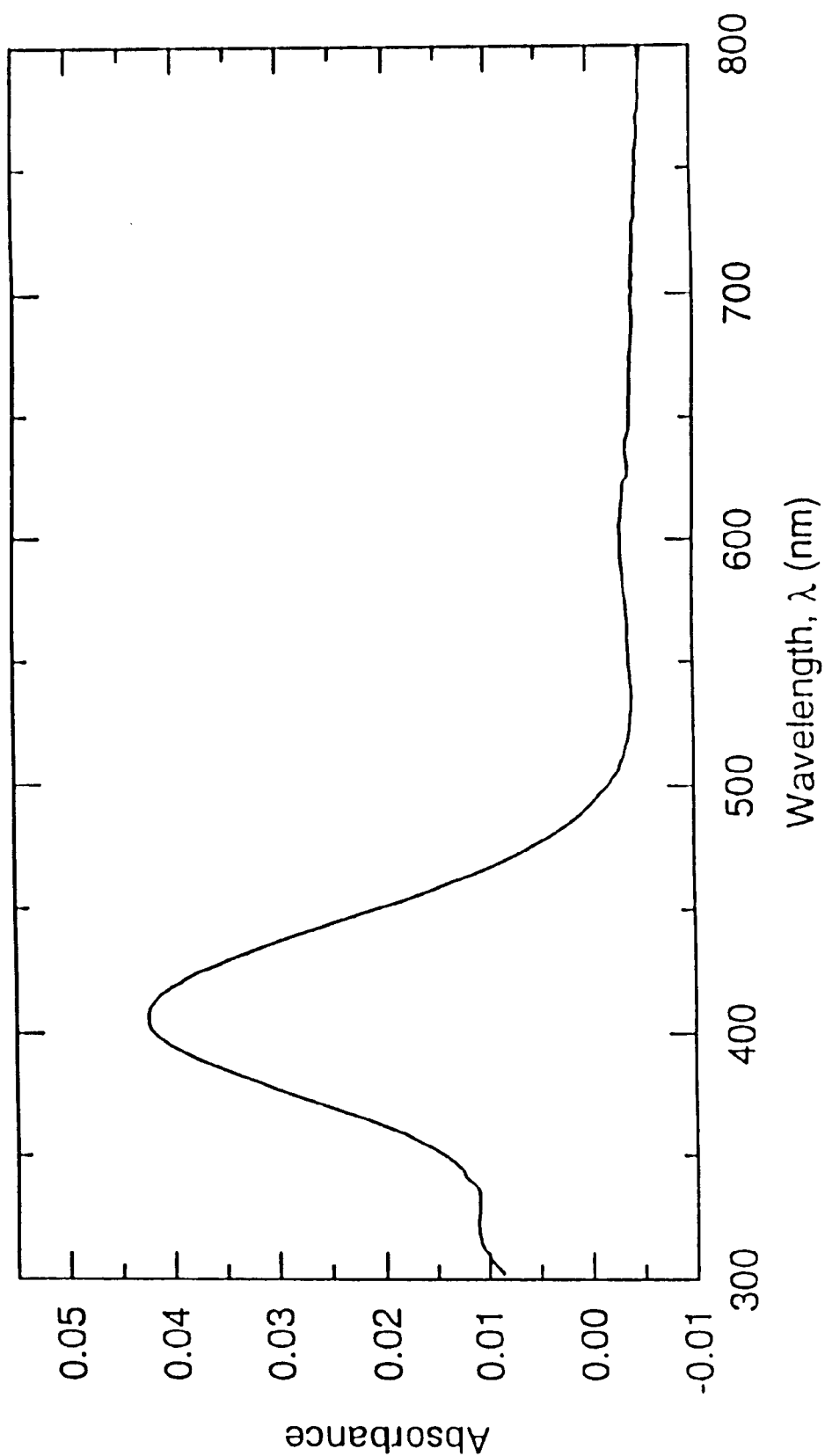
FIG. 16 is a graph of absorption spectrum of bcp in cellulose acetate in the absence of ammonia.

The change in absorption spectra with the change of ammonia concentration can be monitored continuously. FIG. 15 shows the graph of the absorption spectra of this system responding to various amounts of ammonia. BCP dye absorbs very strongly near 420 nm wavelength in the absence of ammonia as shown in FIG. 16. After the film is exposed to ammonia, the maximum absorption peak is shifted toward a longer wavelength near 600 nm as shown in FIG. 15. It is clear that the absorbance increases with an increase in ammonia concentration.

BCP/cellulose acetate: Once the film-coated glass substrate is dried and placed in the flow cell, it is ready to be tested for its response to ammonia gas. For the absorption-based method, the flow cell is mounted in a Genesys 5 UV-Vis spectrophotometer. The ammonia gas generated in a permeation tube in an oven at a particular temperature is delivered to the flow cell though continuous flow of nitrogen.

Figure 17:
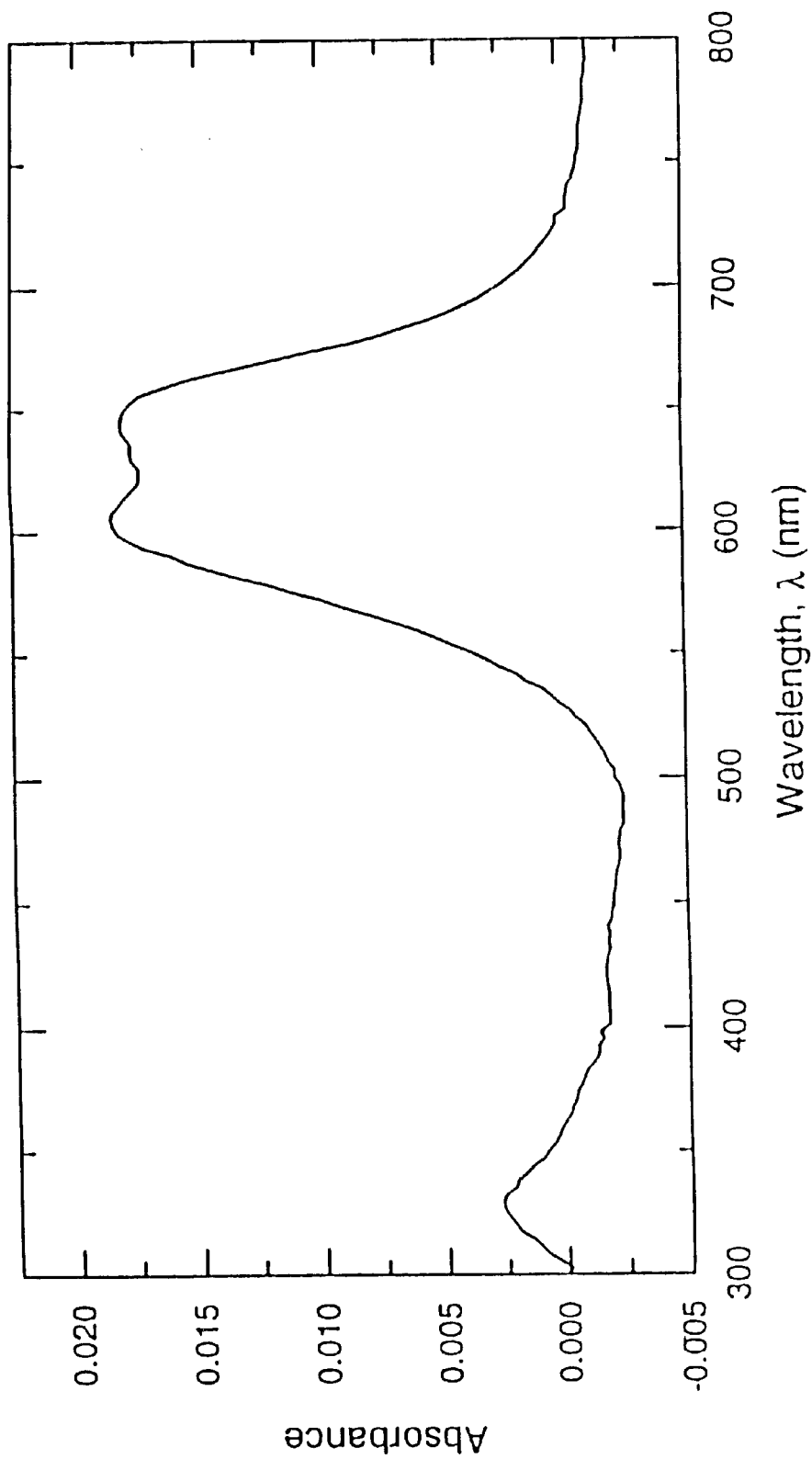
FIG. 17 is a graph of absorption spectrum of nile blue-doped pem in the absence of ammonia.
Figure 18:
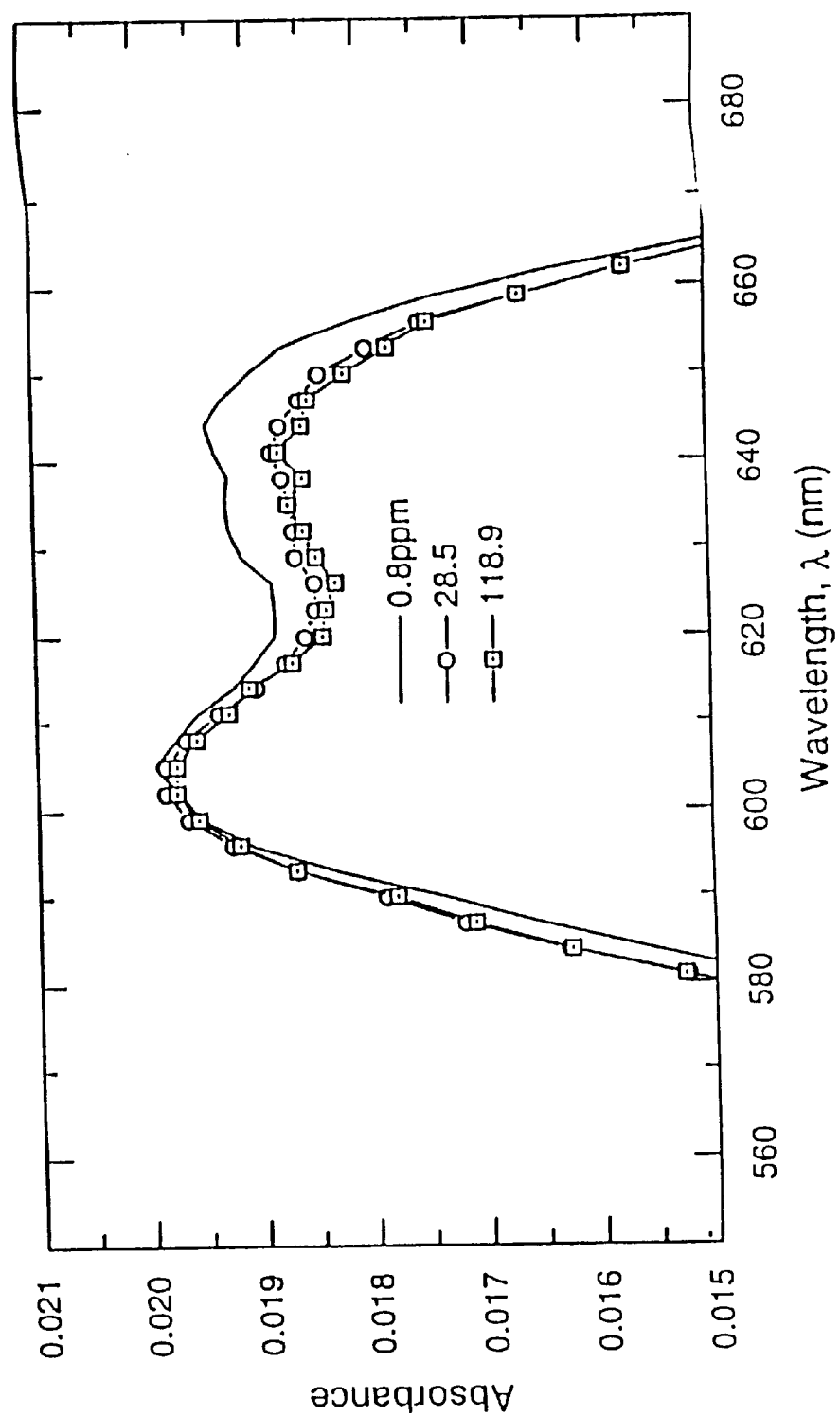
FIG. 18 is a graph of absorption spectra of nile blue-doped pem in the presence of various concentrations of ammonia.

Nile blue/PEM system: Nile blue is a fluorescent solvatochromic dye that can be excited by a He—Ne laser at 633 nm wavelength or a diode laser at 638 nm. FIG. 17 is the graph of the absorption spectrum of nile blue-doped PEM thin film in the absence of ammonia. FIG. 18 is a graph of a detailed spectral region showing the characteristic response to ammonia gas. The absorbance at 645 nm decreases significantly when the ammonia concentration is increased from 0.8 ppm to 28.5 ppm. Any further increase in ammonia concentration up to 118.9 ppm does not produce further change in the absorbance at 645 nm. Therefore, this type of film is applicable to detect very low quantities of ammonia.

Figure 19:
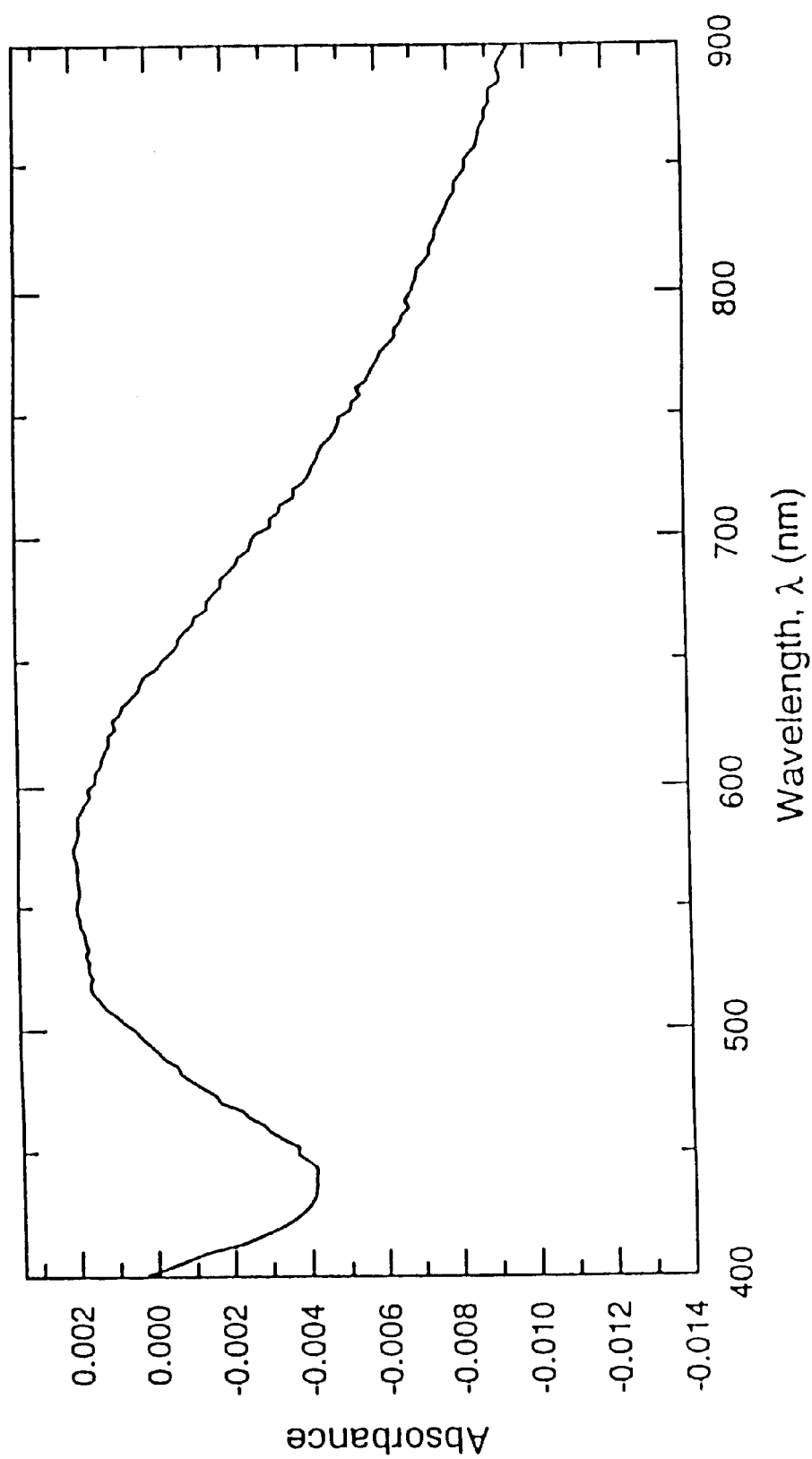
FIG. 19 is a graph of absorption spectrum of $diic_1(5)$ in nafion before exposure to ammonia (film was dried in air).
Figure 20:
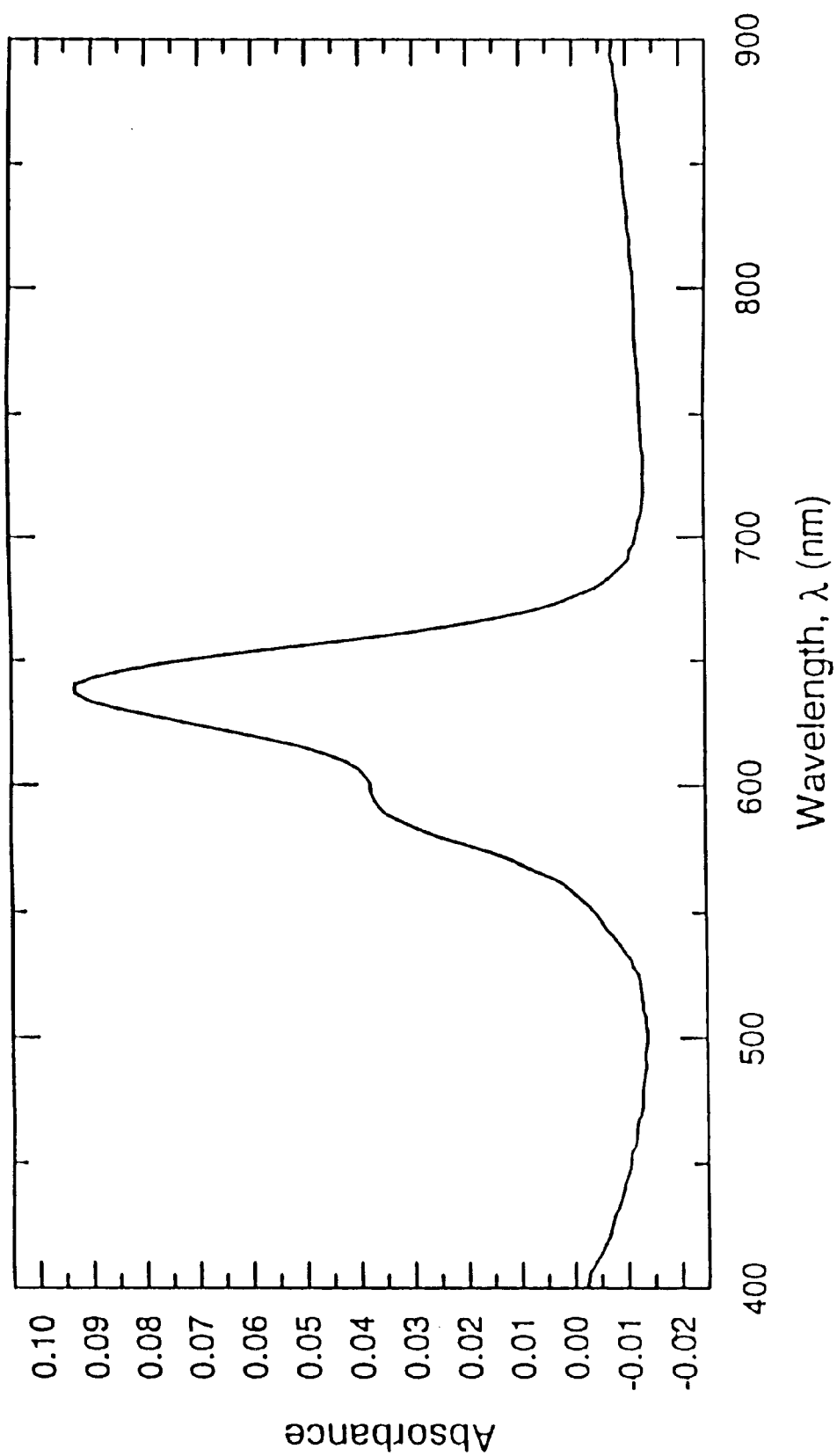
FIG. 20 is a graph of absorption spectrum of $diic_1(5)$ in nafion after exposure to ammonia (film was dried in air).

$DiIC_1(5)$/Nafion system: The absorption spectra of this dye-polymer system, before and after exposure to ammonia, are shown in FIGS. 19 and 20. Right after the film is dried in air at room temperature, it shows a broad absorption peak near 560 nm (FIG. 19). After the film is exposed to ammonia gas, the absorption peak narrows and its maximum value shifts toward longer wavelength near 635 nm (FIG. 20). A He—Ne laser at 633 nm can be used to excite this film and the change in the emission spectrum after interacting with ammonia can be monitored.

Figure 21:
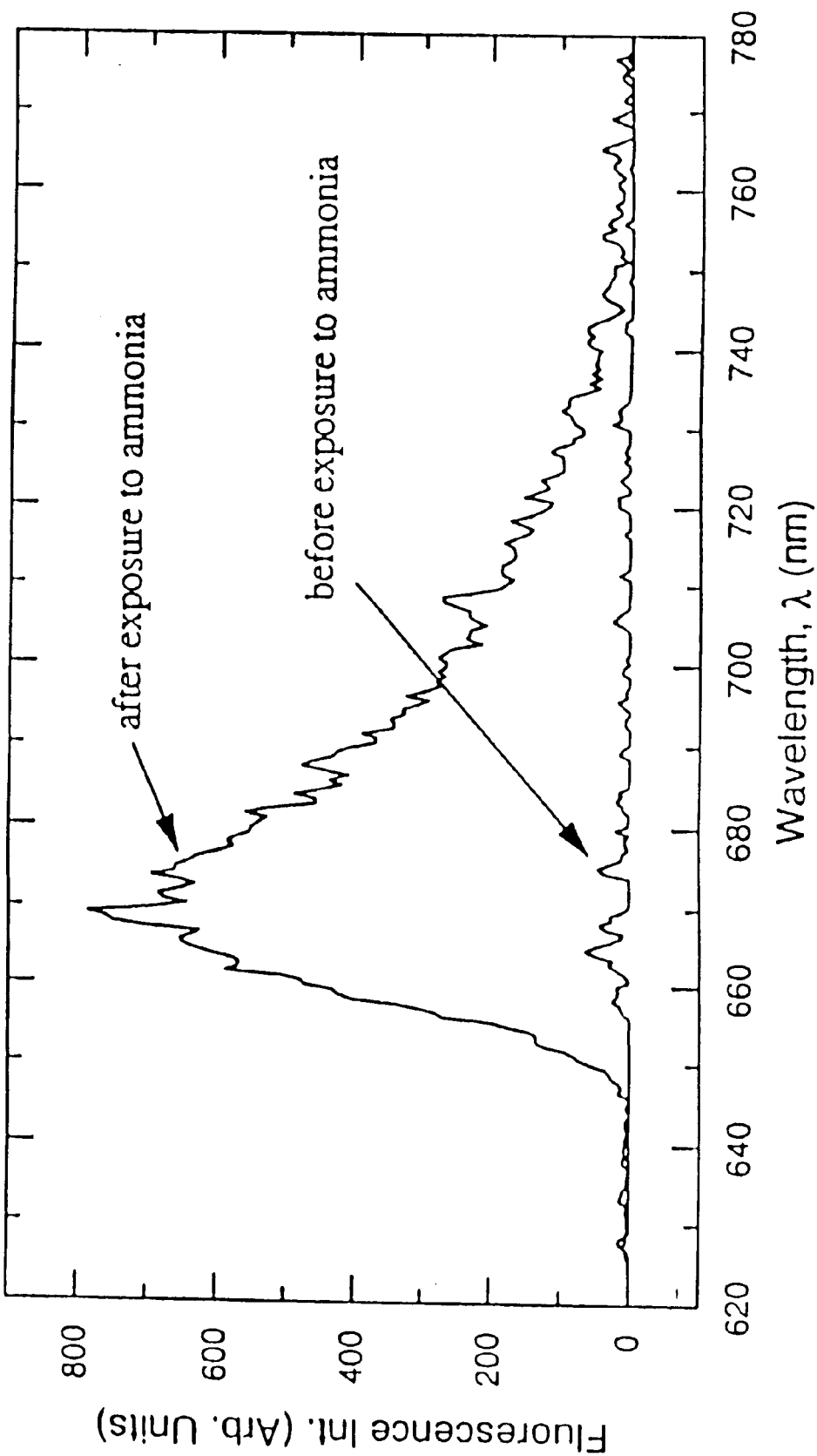
FIG. 21 is a graph of emission spectra of $diic_1(5)$ dye in nafion before and after exposure to $nh_3$ vapor (film was dried in air).

FIG. 21 demonstrated that the air-dried film does not emit any fluorescence when excited by the laser, since the film does not absorb at this particular wavelength. However, after the film is exposed to ammonia, the fluorescence increases dramatically, because the film starts to absorb at 633 nm(FIG. 20). An inexpensive diode laser having a 648 nrn line has also been used to excite thin films for ammonia detection. The air-dried film was also subject to heat treatment in an oven at 120° C. to remove solvents and for curing.

Figure 22:
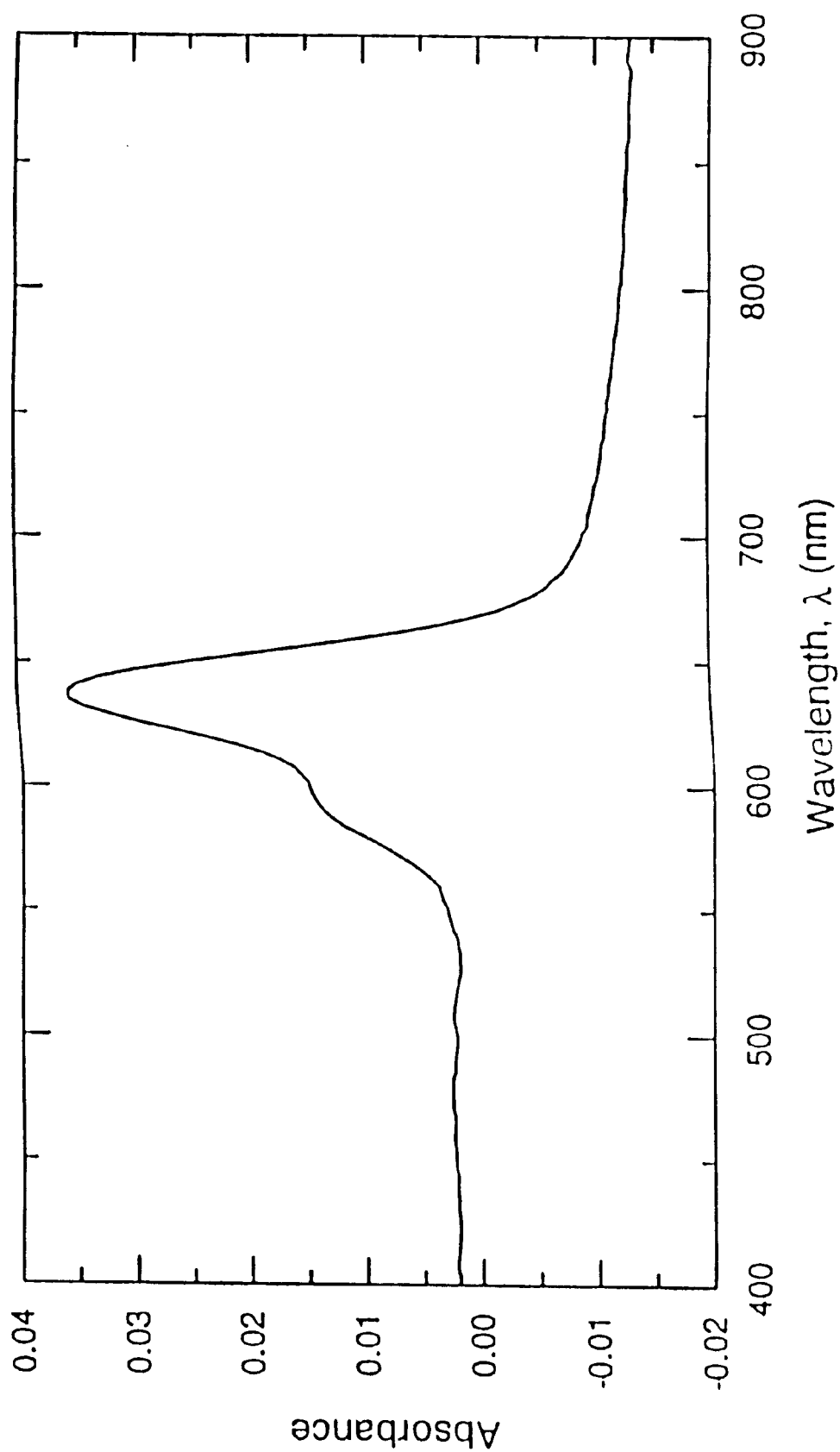
FIG. 22 is a graph of absorption spectrum of $diic_1(5)$ in nafion after being dried in air oven at 120° C.

FIG. 22 is the absorption spectrum of the film after it was dried in the oven. The film has an absorption peak at 635 nm and shows a considerable amount of fluorescence (FIG. 23).

Figure 23:
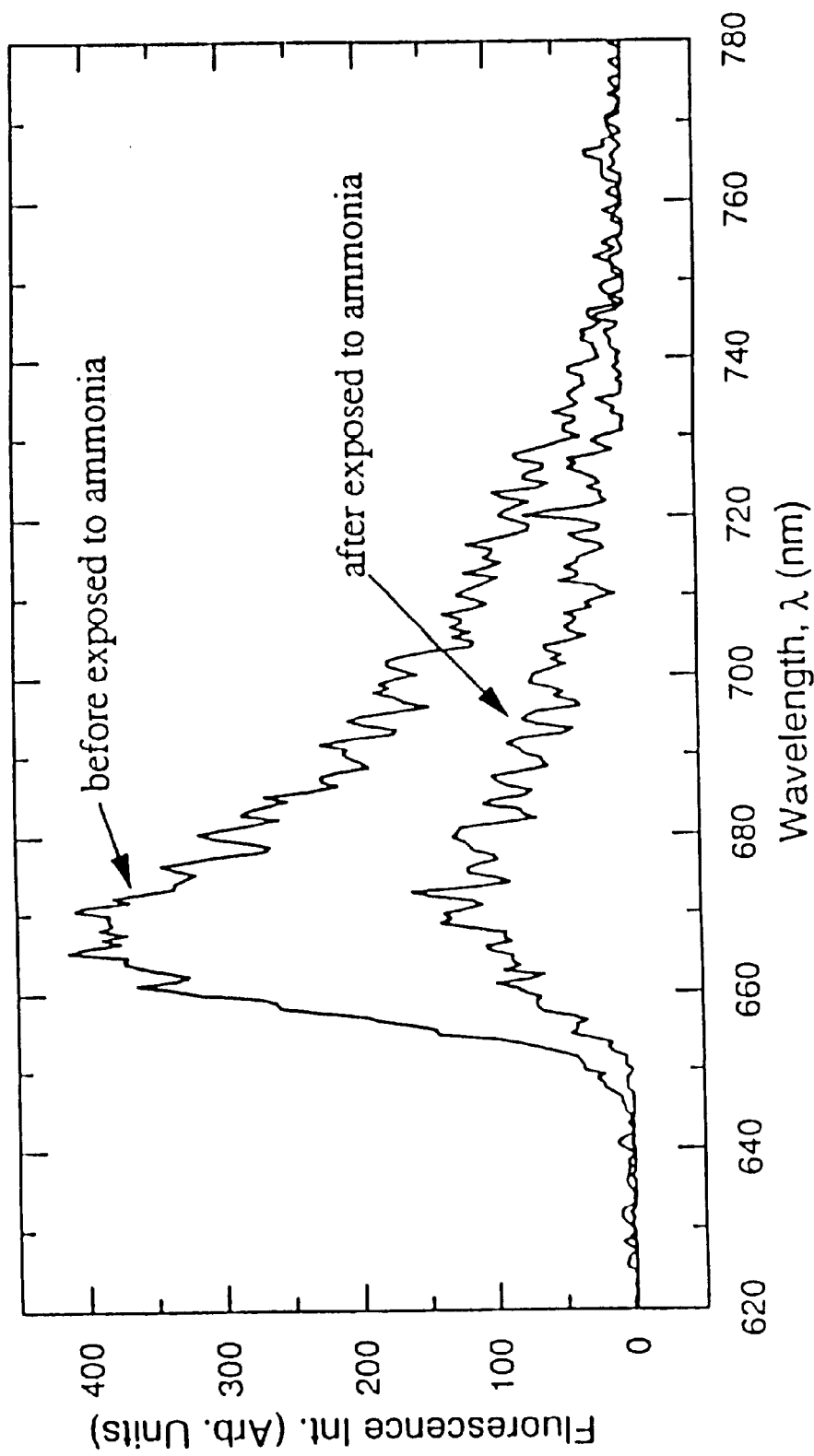
FIG. 23 is a graph of emission spectra of $diic_1(5)$ dye in nafion before and after exposure to $nh_3$ vapor (film was dried in over at 120° C.).

FIG. 23 also demonstrated that the film has a reverse effect upon interacting with ammonia. The fluorescence decreases with ammonia. The OX170/Nafion system behaves the same way as the $DiIC_1(5)$/Nafion system. Both systems are very sensitive to low concentrations of ammonia (1.2 ppm) with irreversible response.

Figure 24:
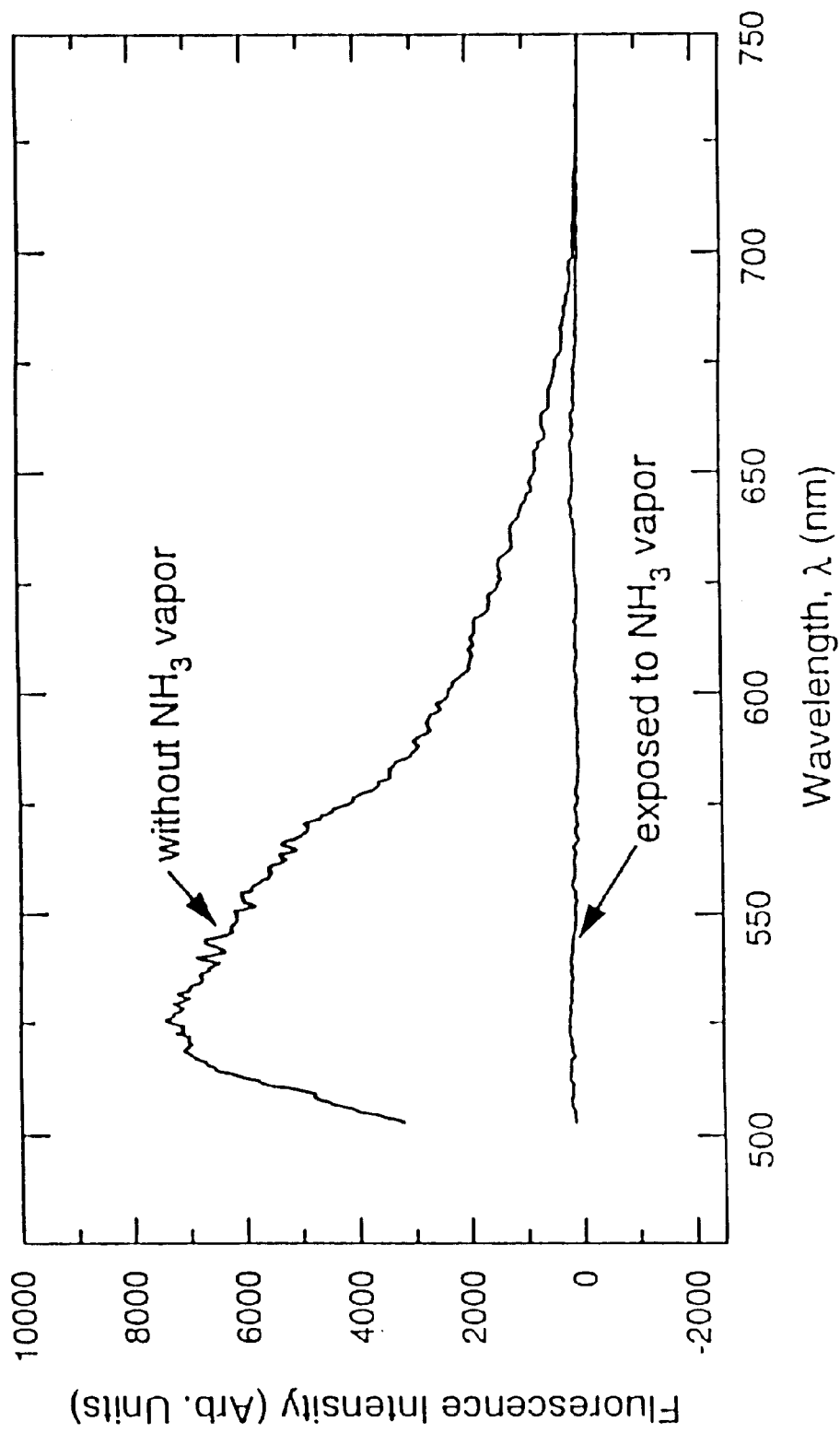
FIG. 24 is a graph of emission spectra of oxazine 170 in nafion film before and after exposure to ammonia vapor.

OX170/Nafion System: Work was performed to use near-infrared excitable fluorophores for ammonia sensing. Among the many combinations of near-infrared dyes and polymer combinations, oxazine 170 perchlorate or oxazine 720 perchlorate was found to be most sensitive to ammonia when it was incorporated in Nafion films. The concentrations of Nafion and oxazine 170 in the matrix were 0.5wt % and $1 \times 10^{-4}$M, respectively. After the film was coated on a glass substrate, it was dried at room temperature for several hours. When the film was excited by an argon-ion laser, emission in the yellow spectral region was observed (FIG. 24).

Figure 25:
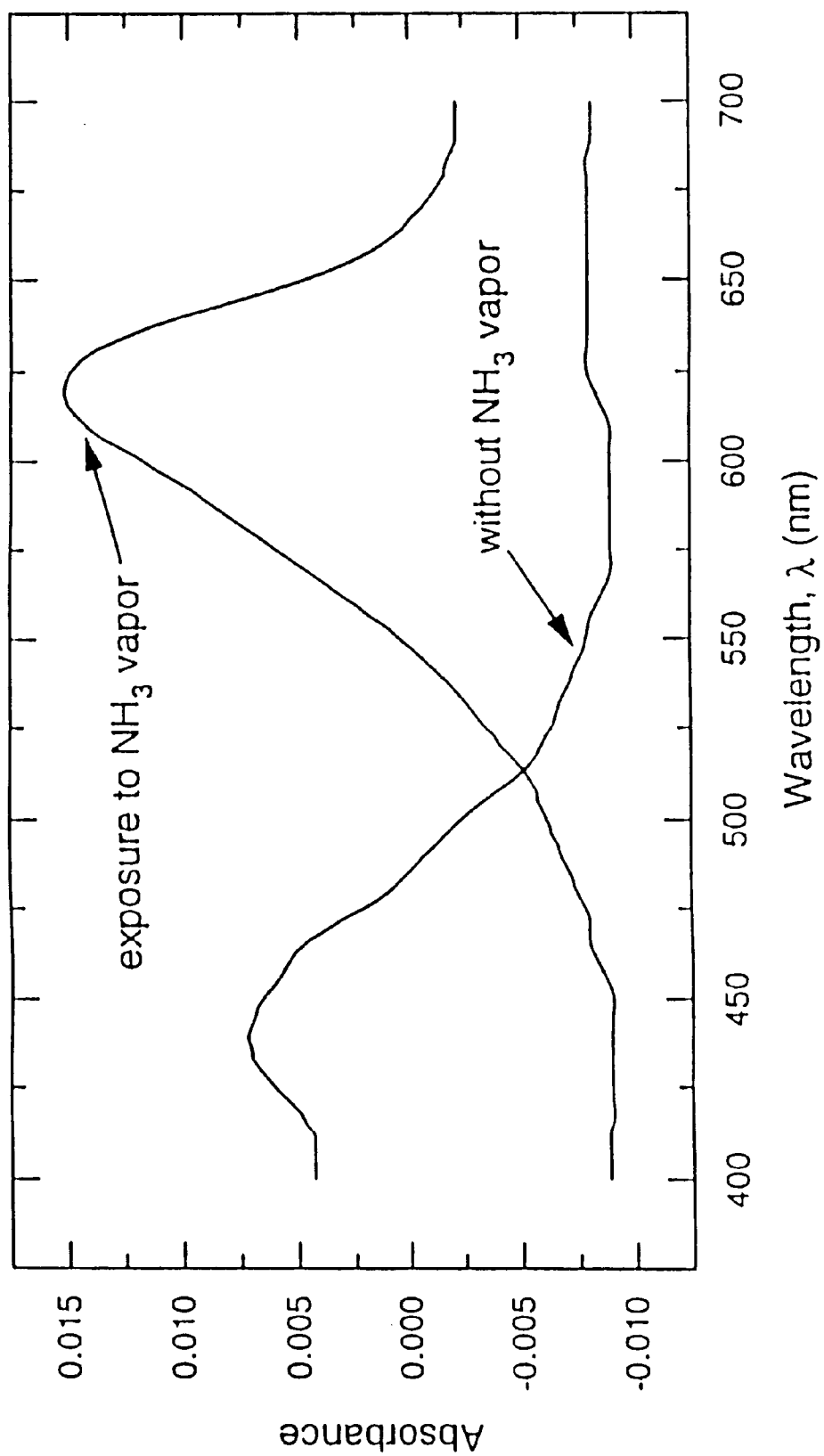
FIG. 25 is a graph of absorption spectra of oxazine 170 in nafion film before and after exposure to ammonia vapor.

When the film was exposed to ammonia vapor, the fluorescence of oxazine 170 was immediately and totally quenched. FIG. 25 shows the absorption spectra of the film both in the absence and presence of ammonia gas. Before the film was exposed to $NH_3$, there was a major absorption peak centered at 435 nm wavelength that can be excited by the 458 nm line of an argon-ion laser. After the film took up the ammonia vapor, this peak disappeared completely, thereby indicating insensitivity to the blue laser light. Instead, a new absorption peak appeared near 620 nm. Although the film responds to $NH_3$, it is irreversible upon removal of the $NH_3$ gas, thereby indicating that ammonia that had been adsorbed to the film could not escape. Heating the film in the oven at 120° C. could regenerate the film with original properties.

Scientists have succeeded in modifying the surface properties of materials by adsorbing onto their surfaces a monolayer or a multilayer of organic molecules forming an ultrathin film. These ultrathin films have applications in many areas, such as integrated optics, chemical sensors and coatings for reducing friction between moving surfaces. A new technique for the construction of multilayer assemblies involves the adsorption of alternating anionic and cationic bipolar amphiphile or polyelectrolyte layers consecutively onto a silanized surface. The driving force for multilayer buildup is the electrostatic attraction between opposite charges so that there is no covalent bond formed.

Figure 26:
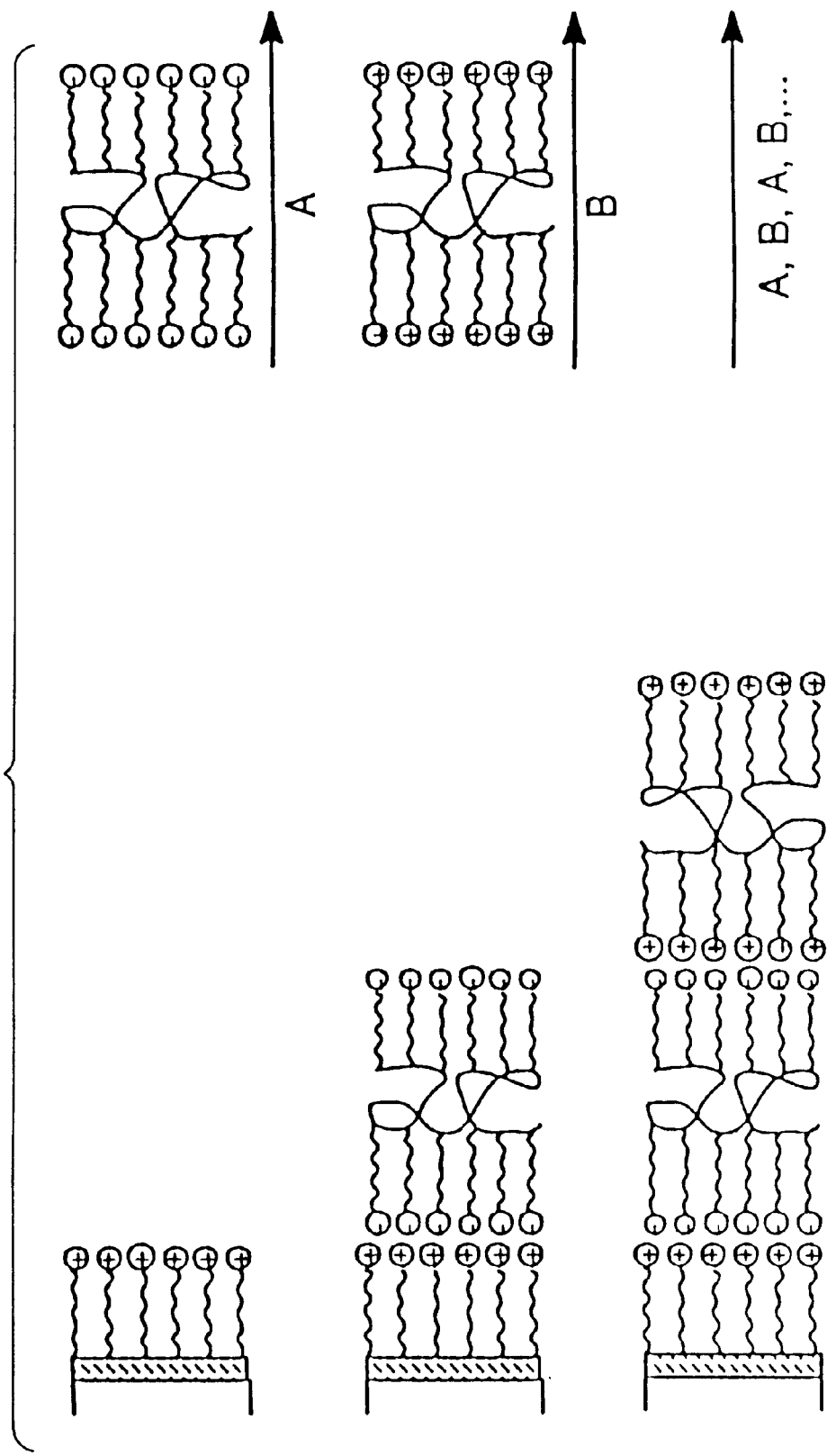
FIG. 26 is a flow chart for the buildup of multilayer assemblies by consecutive adsorption of anionic and cationic polyelectrolytes.

The procedure for depositing multilayers of self-assembled (SA) bilayers is shown in FIG. 26, and is outlined as follows. A solid substrate with a positively charged surface is immersed in a solution containing an anionic polyelectrolyte, such as polystyrene sulfonic acid) (PSSA), and a monolayer of the polyanion is adsorbed (Step A). After rinsing in water, the substrate is immersed in the solution containing a cationic polyelectrolyte, such as polyallylamine hydrochloride (PAA), and a monolayer is adsorbed with the outer surface being positively charged (Step B). By repeating both steps alternately (A, B, A, B, . . . ) multiple SA monolayers of both polymers are obtained. Using this method, 100 layers of SA monolayers were deposited successfully on a silicon surface. Polystyrene sulfonic acid (PSSA) and polyallylamine (PAA) have been used as anionic and cationic polymers to build multilayers in this project.

Figure 27:
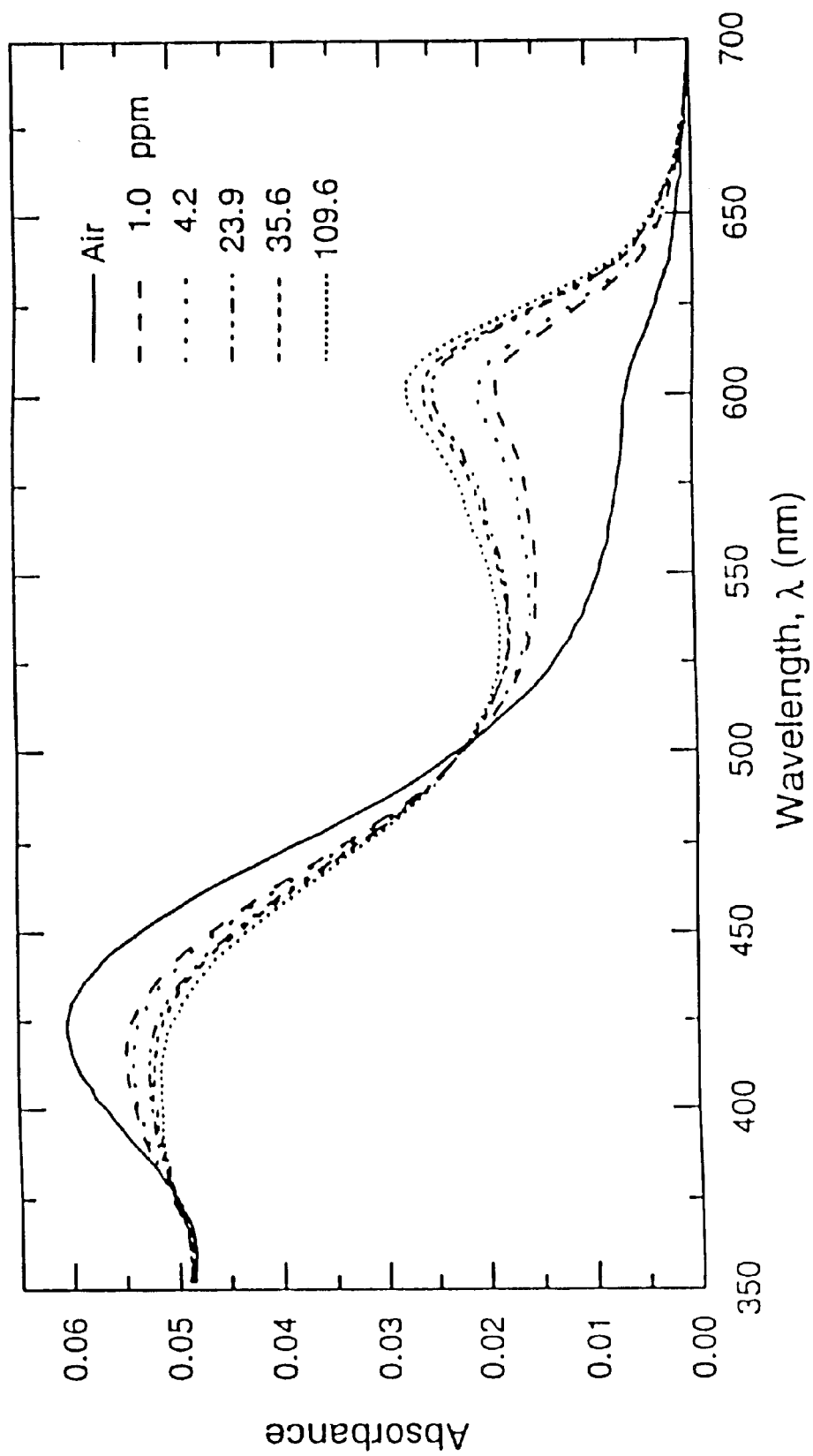
FIG. 27 is a graph of response of four layers of sa films to ammonia.

Work was performed to select ammonia-sensitive absorbing materials for incorporation in the multilayer thin-film. Several dyes have been studied for this purpose and bromocresol purple (BCP) was found to exhibit the largest change in absorption in the presence of ammonia. BCP has been incorporated in cationic polymer solutions and codeposited onto the anionic surface. FIG. 27 shows the absorption spectra of a four-multilayer film responding to ammonia gas. The freshly prepared film absorbs at 440 nm, corresponding to the acidic absorption peak of BCP. After ammonia is passed to the flow cell, the peak at 440 nm decreases while the peak at 600nm increases with ammonia concentration. The peak at 600 nm corresponds to the basic absorption peak of BCP. The film was very sensitive to ammonia below 1 ppm and continued to respond to ammonia up to 23.9 ppm. Above 23.9 ppm, the film seemed to be saturated and no further change was observed.

Since the amount of BCP in four multilayers was limited, it could only interact with limited amounts of ammonia which accounted for the high sensitivity of the film. When the film was exposed to liquid ammonium hydroxide, some of the BCP was washed away from the film. At high concentrations of ammonium hydroxide, the film would be destroyed due to high ionic strength. Both effects would resulting the loss of delectability by the film and in reduced absorbance signal.

Figure 28:
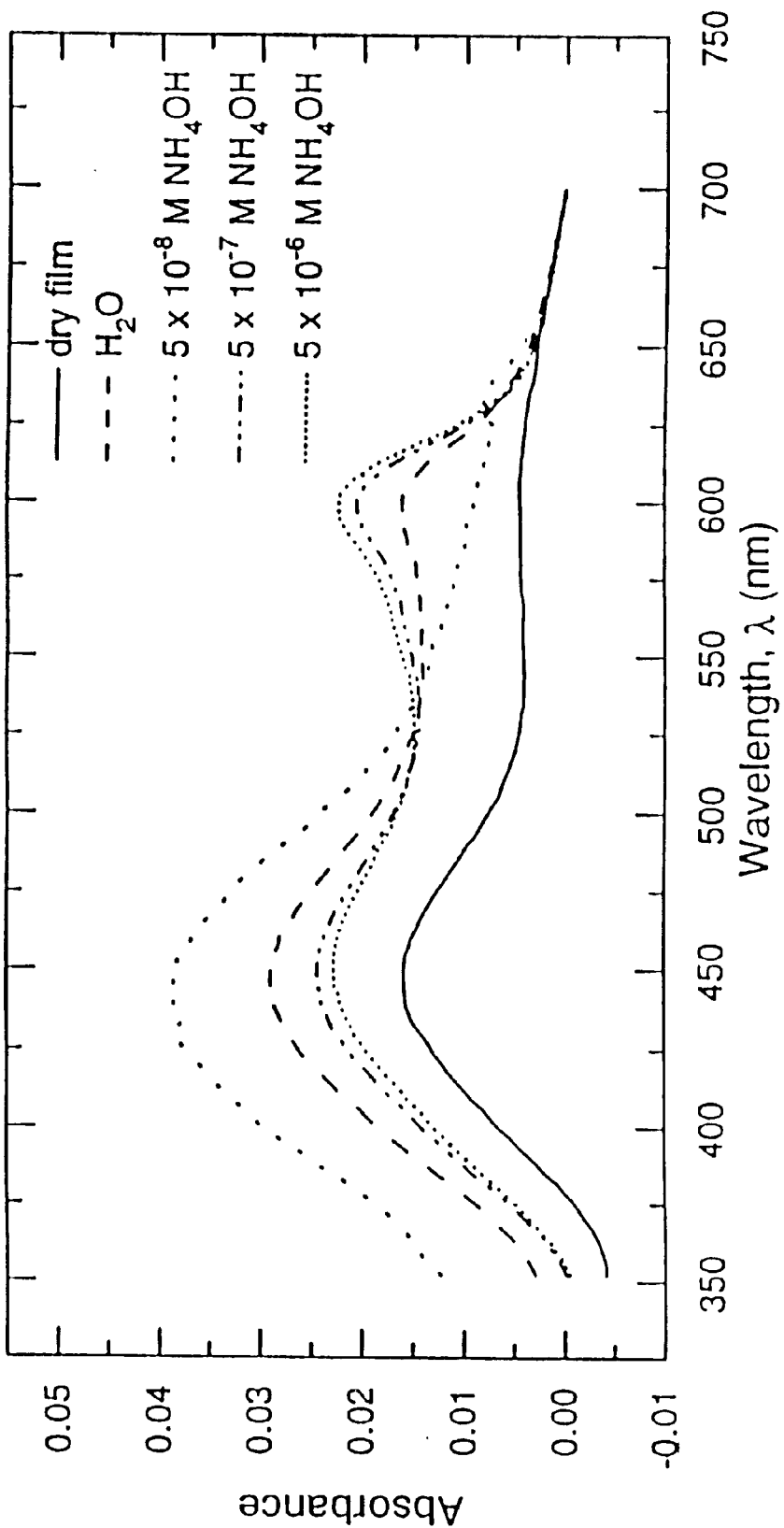
FIG. 28 is a graph of response of teflon-coated sa films (4 layers) to ammonium hydroxide solution.

These problems were solved by dip-coating a very thin layer of Teflon film on the top of the multilayer assembly. FIG. 28 demonstrated the results of this technique. Again the film was very sensitive to very low concentrations of ammonium hydroxide from $10^{-8}$M to $10^{-7}$M. The thickness of Teflon film was critical to the response time of the sensor and the number of multilayers is important to the detection range of the sensor. About 1% Teflon coating solution was required during the coating stage to produce an even Teflon film with reasonable response time of minutes. only 3–5 multilayers were required to make a sensitive film for ammonia detection. Additional multilayers probably would add more background intensity to the absorption spectra and would result in a reduced sensitivity.

It may be noted from FIG. 28 that the total absorbance of the multilayer film was on the order of 0.01 prior to exposure to ammonia and 0.02 after to exposure to $10^{-7}$M ammonium hydroxide. Assuming that the multilayer film is 12 nm thick, the calculated absorption coefficient would be 16,670 $cm^{-1}$, which is consistent with values found in the technical literature.

Figure 29:
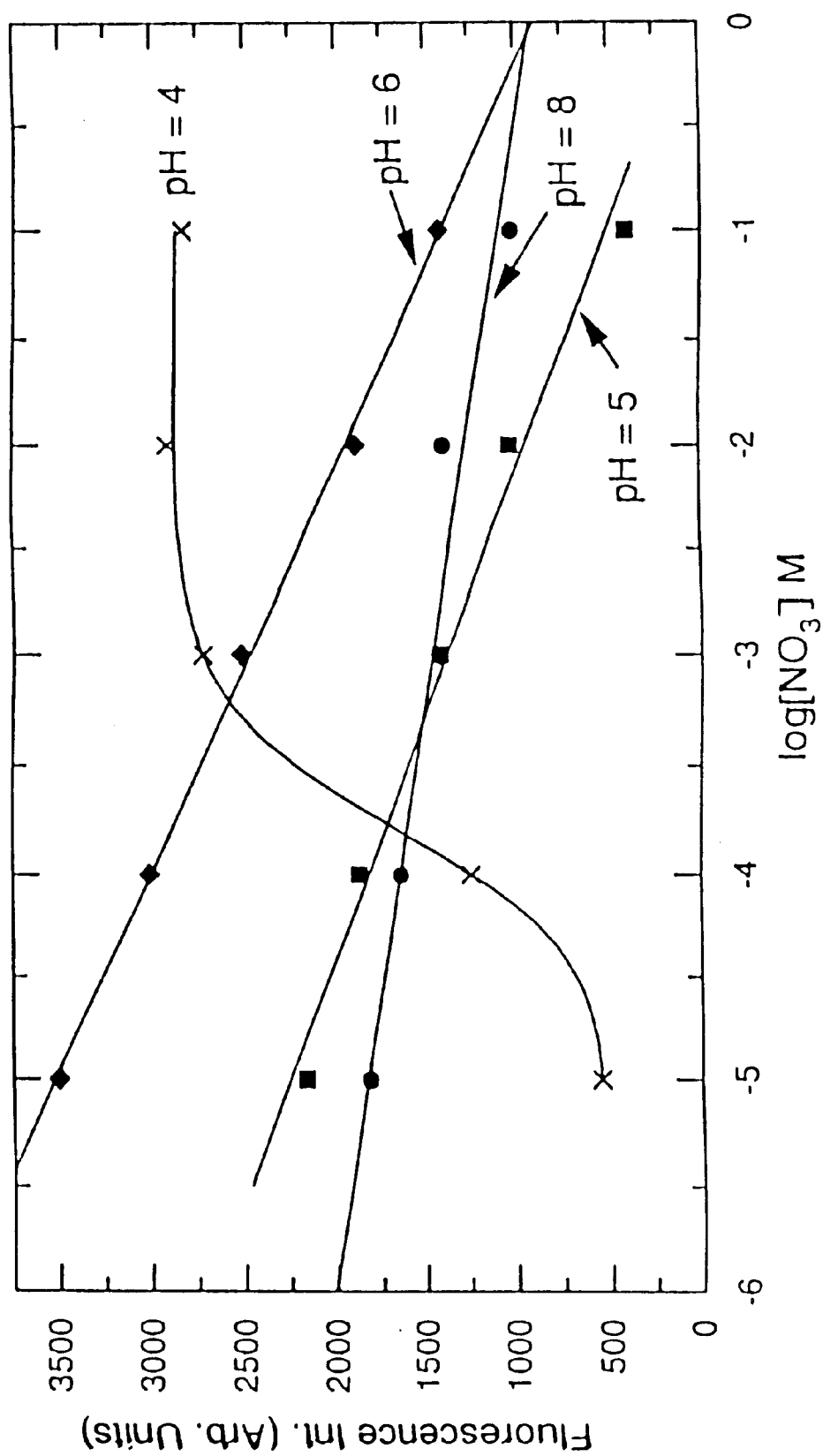
FIG. 29 is a calibration graph of the pvc membrane responding to $no_3^-$ concentration at different ph values.

FIG. 29 is the calibration graph of the film responding to $NO_3^-$ concentrations from $10^{-5}$M to 0.1M at different pH values. This figure illustrates the difficulty of using an indirect sensing method to determine the concentration of nitrate ions. In all these curves, the readings at 535 nm were recorded as the response of the sensing film to nitrate concentration.

At pH of 5, 6 and 8, the response curves are linear in respect to the logarithm of nitrate concentration and the dynamic range is about 4 orders of magnitude. However, at pH of 8, the measurement is less sensitive compared with the curves at pH of 5 and 6. At pH of 4, the response curve is not linear. The fluorescence intensity increases with increasing $NO_3^-$ concentration and is saturated above $NO_3^-$ concentration of $10^{-2}$M. However, the film is more sensitive to low concentrations of $NO_3^-$ for two orders of magnitude from $10^{-5}$M to $10^{-3}$M. The reversed response may be attributed to the complete protonation of the indicators in the PVC membrane at low pH values. Other cations such as Na+ or K+ may be co-extracted with $NO_3^-$ into the membrane to displace the proton. In this way the acidity of the membrane is lowered and the fluorescent intensity increases with $NO_3^-$ concentration. This process may be illustrated by the following reaction scheme:

(5)

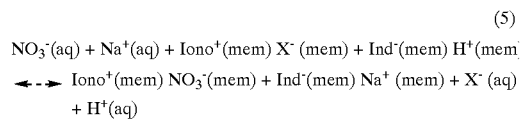

$NO_3^-$(aq) + $Na^+$(aq) + $Iono^+$(mem) $X^-$ (mem) + $Ind^-$(mem) $H^+$(mem)
⇌ $Iono^+$(mem) $NO_3^-$(mem) + $Ind^-$(mem) $Na^+$ (mem) + $X^-$ (aq) + $H^+$(aq)

The response time of the membrane was found to be about one minute and to depend on the concentration of nitrate. The reproducibility of the readings was quite poor, requiring frequent membrane conditioning. To improve sensor performance, new geometries need to be developed.

Crosslinked polyesters containing 15 and 25 mol % tartaric acid were sealed for biodegradability studies. The polymers were hydrolyzed by immersing the samples in 40 ml of 0. 1M phosphate buffer, pH 7.44, at 25° C. The samples were retrieved after various time intervals (2 to 10 days) and were dried in an oven prior to obtaining the weight loss. It is apparent from these two experiments (Table VI and Table VII) that the higher the crosslinking, the lower the hydrolysis. Thus, the greater the amount of the tartaric acid, the slower the rate of weight loss.

Figure 30:
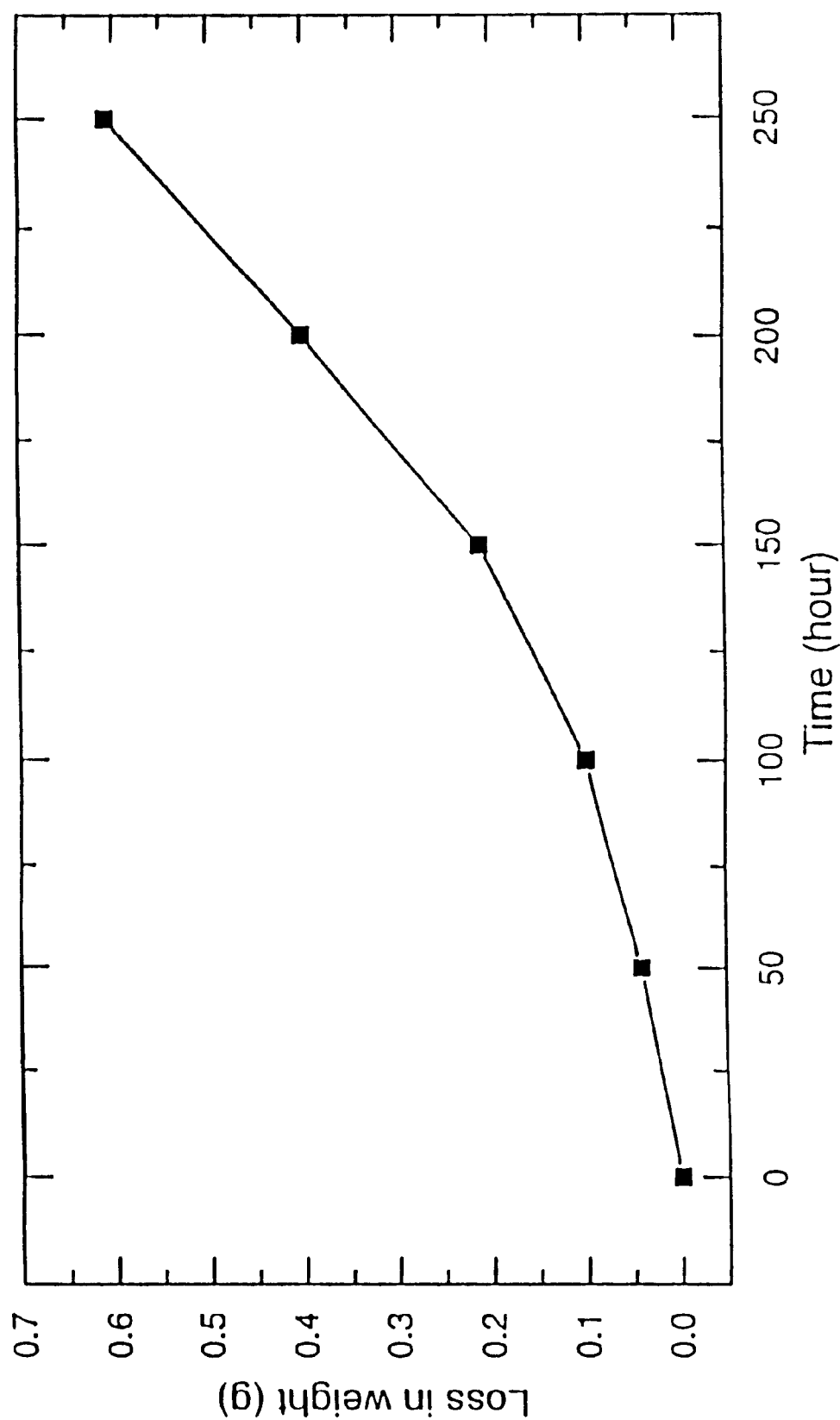
FIG. 30 is a graph of biodegradability studies of polylactic acid containing 25mol % of tartaric acid at ph 7.5.
Figure 31:
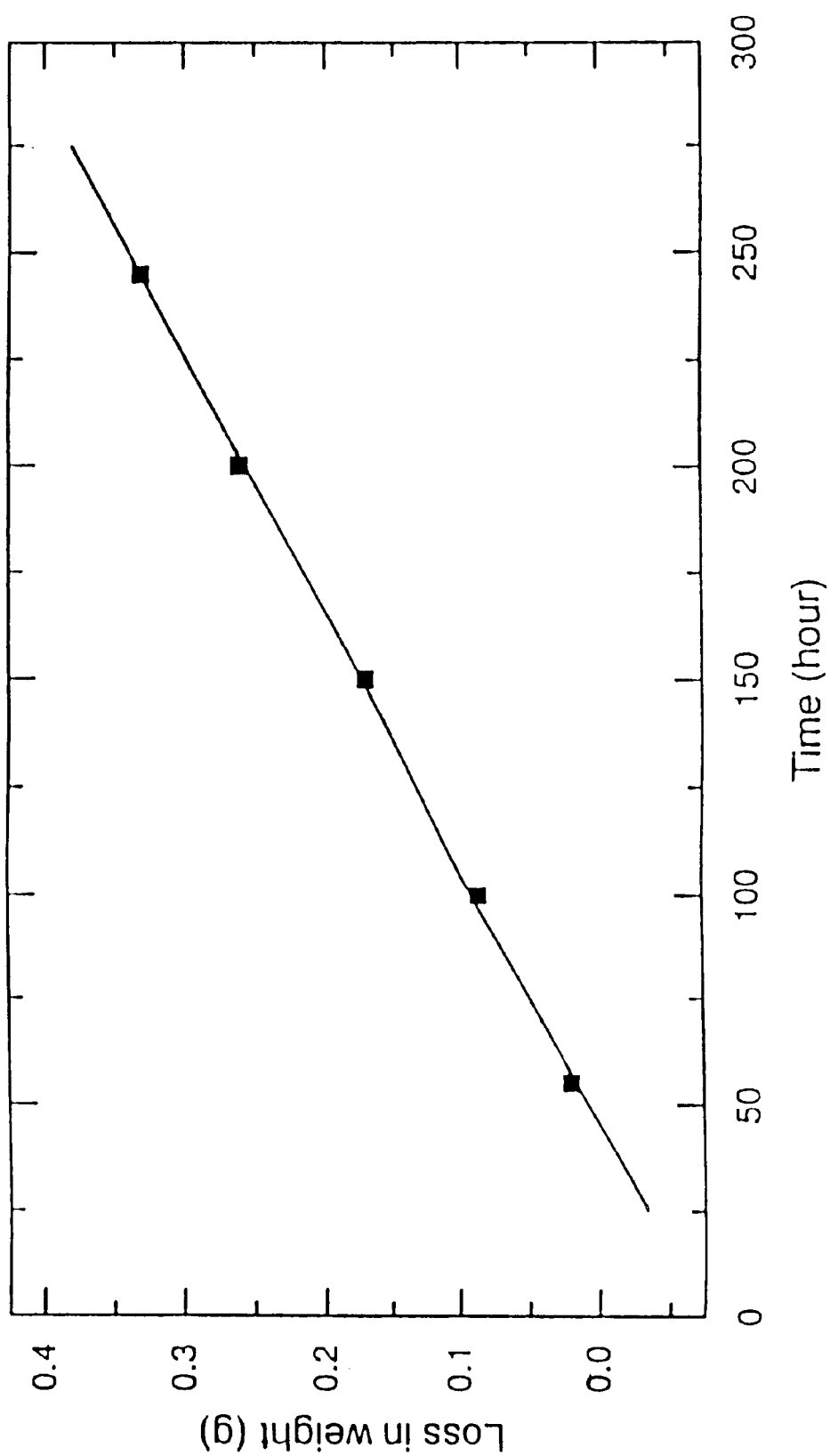
FIG. 31 is a graph of biodegradability studies of polylactic acid containing 15mol % of tartaric acid at ph 7.4.

For crosslinked polymer containing 15 mol % crosslinker, the loss in weight increases exponentially with time during the first four days as illustrated in FIG. 30. The hydrolysis after 4 days was found to increase linearly with time. The rate constant after the first four days estimated from the slope was found to be $4.1 \times 10^{-3}$ gm $hour^{-1}$. The loss in weight due to hydrolytic cleavage of the crosslinked polymer containing 25 mol % of tartaric acid increased linearly with time as demonstrated in FIG. 31. The rate constant estimated from the slope was found to be $1.7 \times 10^{-3}$ gm hour-1. These results indicate that the rate of hydrolysis for crosslinked polymers both containing 15 and 25 mol % tartaric acid were identical. The biodegradation of polyesters is known to proceed via random chain cleavage of the ester moiety so that fragments produced are small enough to be soluble under aqueous conditions, resulting in the loss of weight.

Work was performed to compare three commonly used fluorescence sensor configurations. In the first configuration, an oxygen-sensitive dye is deposited at the end of an excitation optical fiber, and a second optical fiber, transverse to the excitation fiber is used to collect the fluorescence. A second configuration uses the excitation fiber both to excite ii fluorescence and to transmit the fluorescent signal to the photodetector. In the third configuration, a thick optical waveguide is used to excite a fluorophore-containing film deposited on one surface of the waveguide. The fluorescence is collected by optical fibers transverse to the waveguide attached to the surface opposite to the fluorophore. To demonstrate the performance of the first configuration, a dissolved-oxygen sensor was constructed using a combination of a bright blue LED as the light source and a photodetector/amplifier as a detector for the fluorescence signal. $Ru(Ph_2phen)_3^{2+}$ was incorporated into a polysiloxane thin film of dimension 2×2 mm using the method discussed above.

Figure 32:
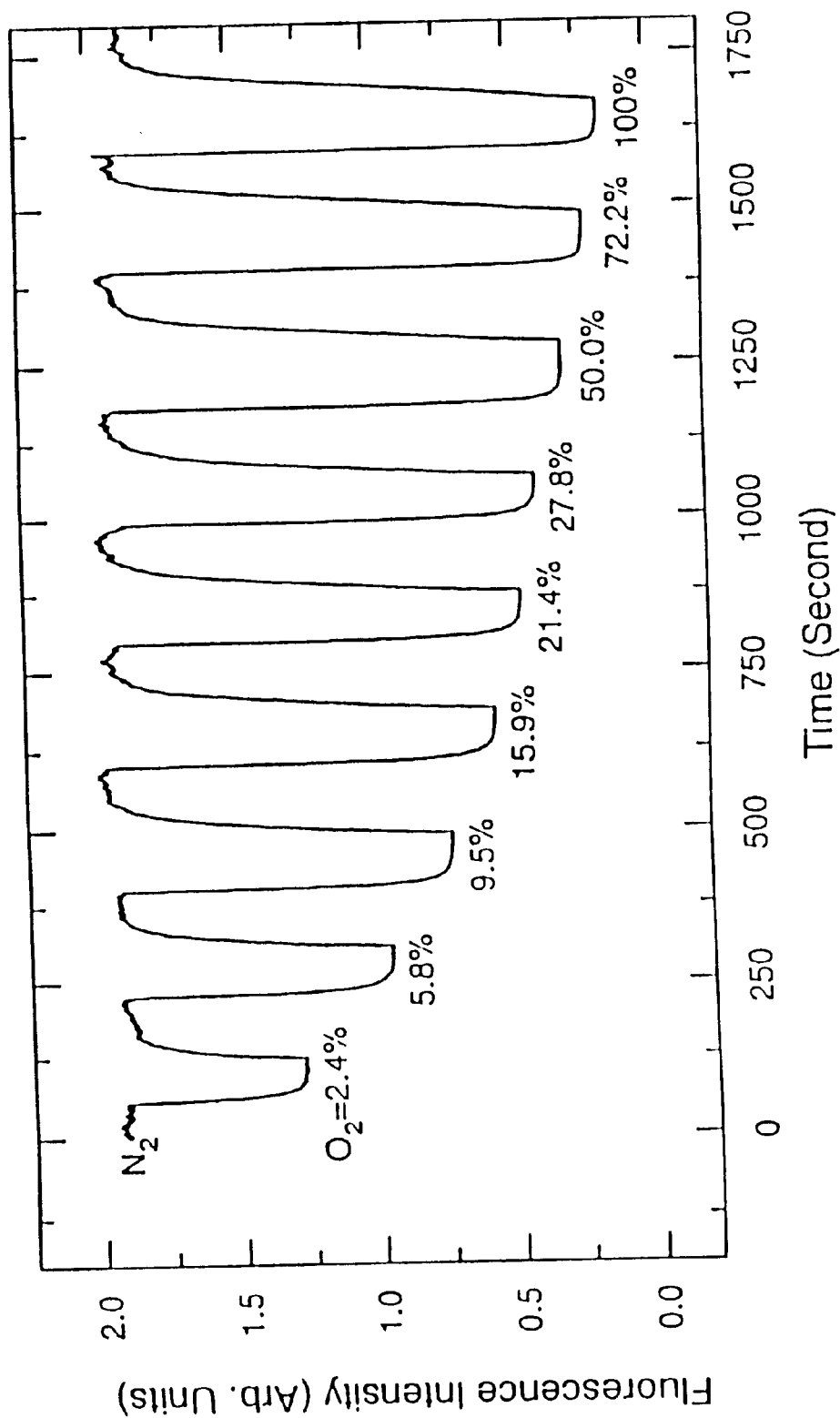
FIG. 32 is a graph of change of fluorescence for oxygen sensors exposed to various levels of oxygen.
Figure 33:
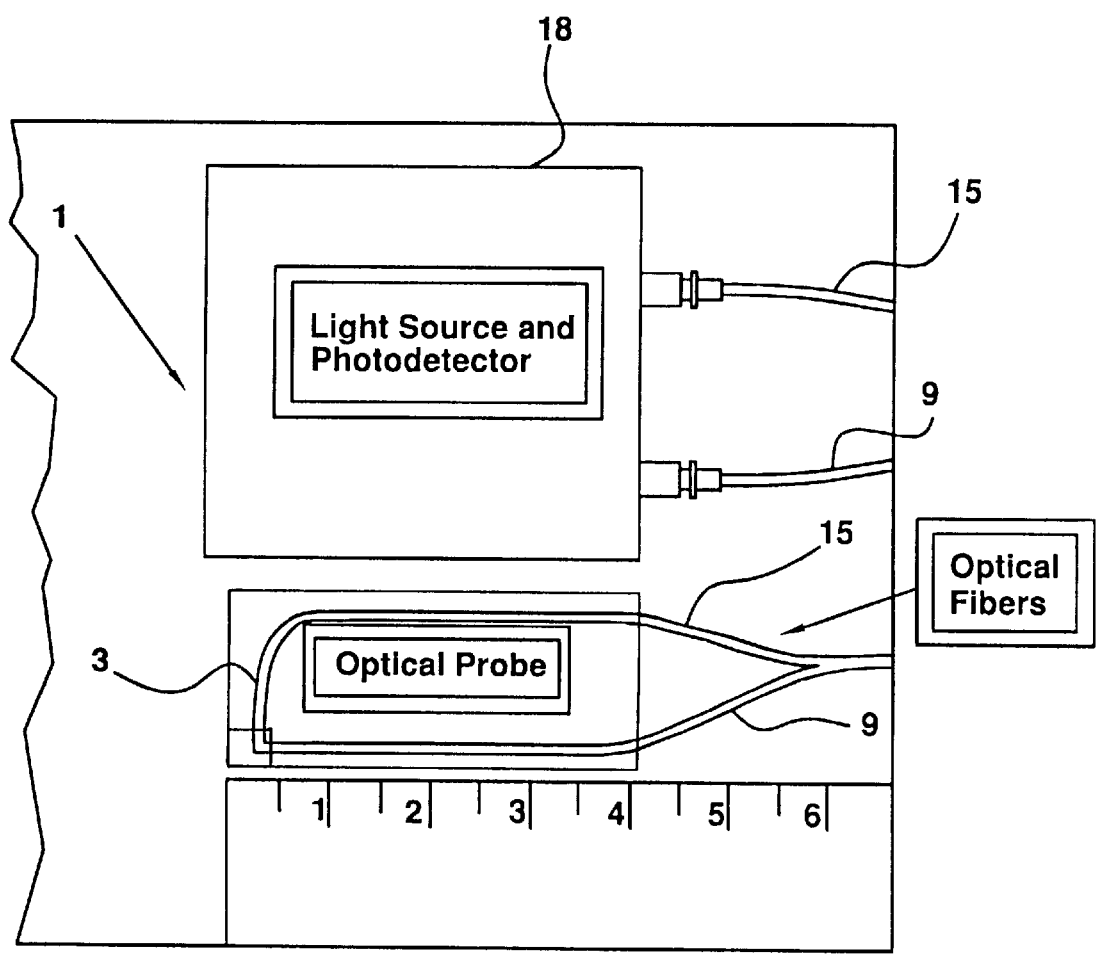
FIG. 33 shows an oxygen probe and sensor configuration.

FIG. 32 shows the response of the oxygen sensor to different levels of oxygen. This modular configuration corresponded to a significant improvement in terms of reduction in cost and size. Since an LED/photodetector combination was used, the total cost of the components was less than $100. The size of the system configuration was also significantly reduced. Since no laser was used in the package, the light source 7 and detector with battery 17 can fit into a package 18 of dimension 10×7×5 cm as shown in FIG. 33. Additional advantages of this oxygen sensor includes fast response time and reduced oxygen consumption relative to conventional Clark-type oxygen sensors. Further improvement in sensor performance has been achieved through the use of a modulated signal and digital signal processing to remove the interference of ambient room light and to reduce the influence of fiber bending losses to be discussed later.

Figure 34:
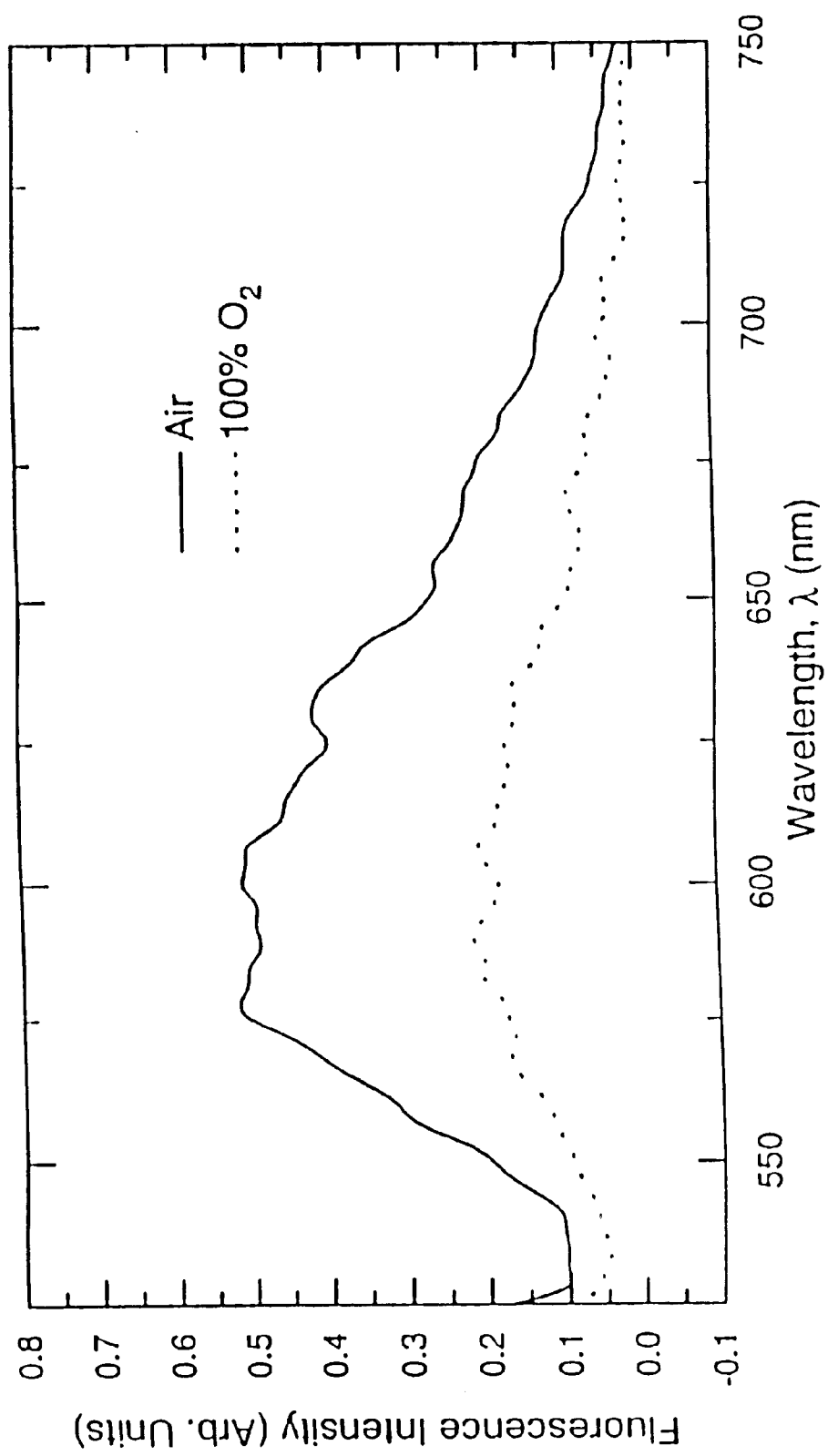
FIG. 34 is a graph of response of oxygen dye entrapment at the end of an optical fiber.

The performance of the second configuration using a single fiber to excite and transmit fluorescence to determine oxygen concentration is shown in FIG. 34. It was observed that while approximately 50% of fluorescent light was captured by the same fiber, some excitation light inevitably will reflect back to the detector resulting in reduced signal-to-noise ratio. Several advantages of this setup include simplified sensor head, compact size and a single fiber for excitation and collection of fluorescence. The major disadvantage is that unless the Stoke's shift of the fluorescence is large enough to be separated by a long-wavelength-pass filter, this configuration will result in very low signal-to-noise ratio.

Figure 35:
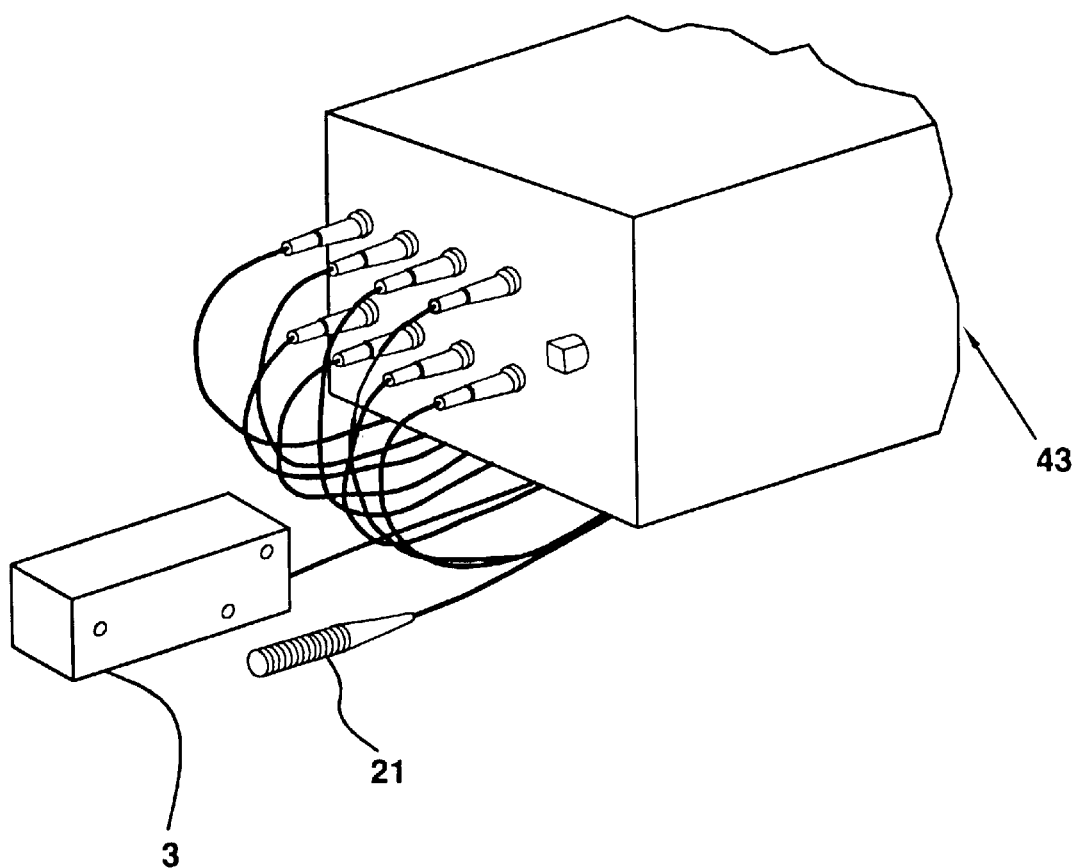
FIG. 35 shows a multiplexed fiber-optic oxygen sensor and two types of optical probes.
Figure 36:
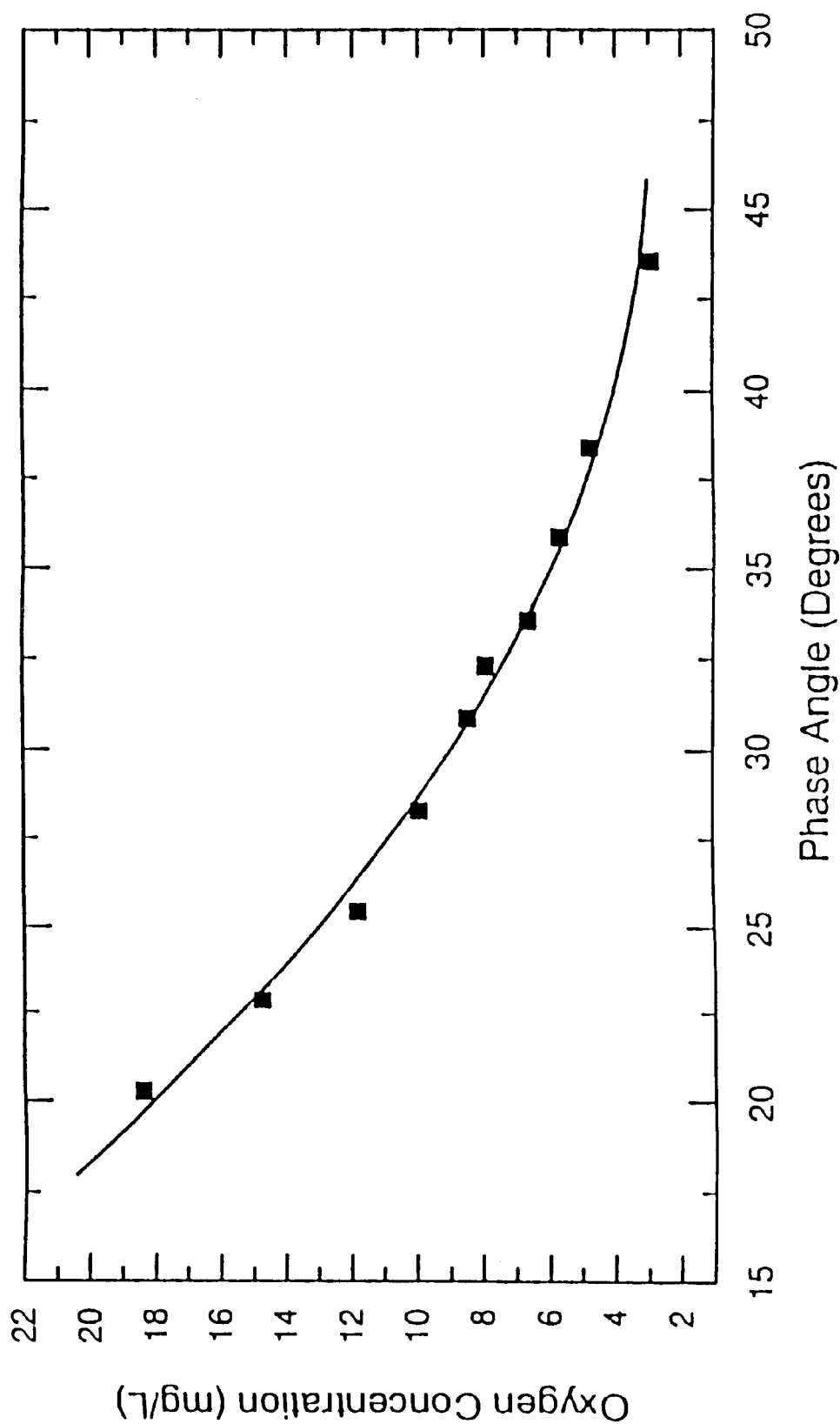
FIG. 36 is a graph of calibration curve used for determining dissolved-oxygen levels with phase angle measured by the instrument.

FIG. 35 shows the multiplexed fiber-optic sensor system 43 and two types of fiber-optic probes 3, 21 developed. The dimension of the instrument is 13 cm×10 cm×20 cm. Type I fiber-optic probe 3 uses one fiber for excitation 9 and a second fiber for collection 15 of fluorescence. Type H fiber-optic probe 21 uses the configuration of dye attachment 5 to the end of fiber tip 29. The dimensions of Type I and H fiber-optic probes are 2 cm×2 cm×7 cm and 0.8 cm diameter×3 cm length respectively. The performance of the two probe types is similar, with Type H probe having a slightly higher fluorescence signal. FIG. 36 shows a calibration curve of a typical sensor for dissolved-oxygen. A second-order polynomial was used to generate the fitting curve from the measured data.

Figure 37:
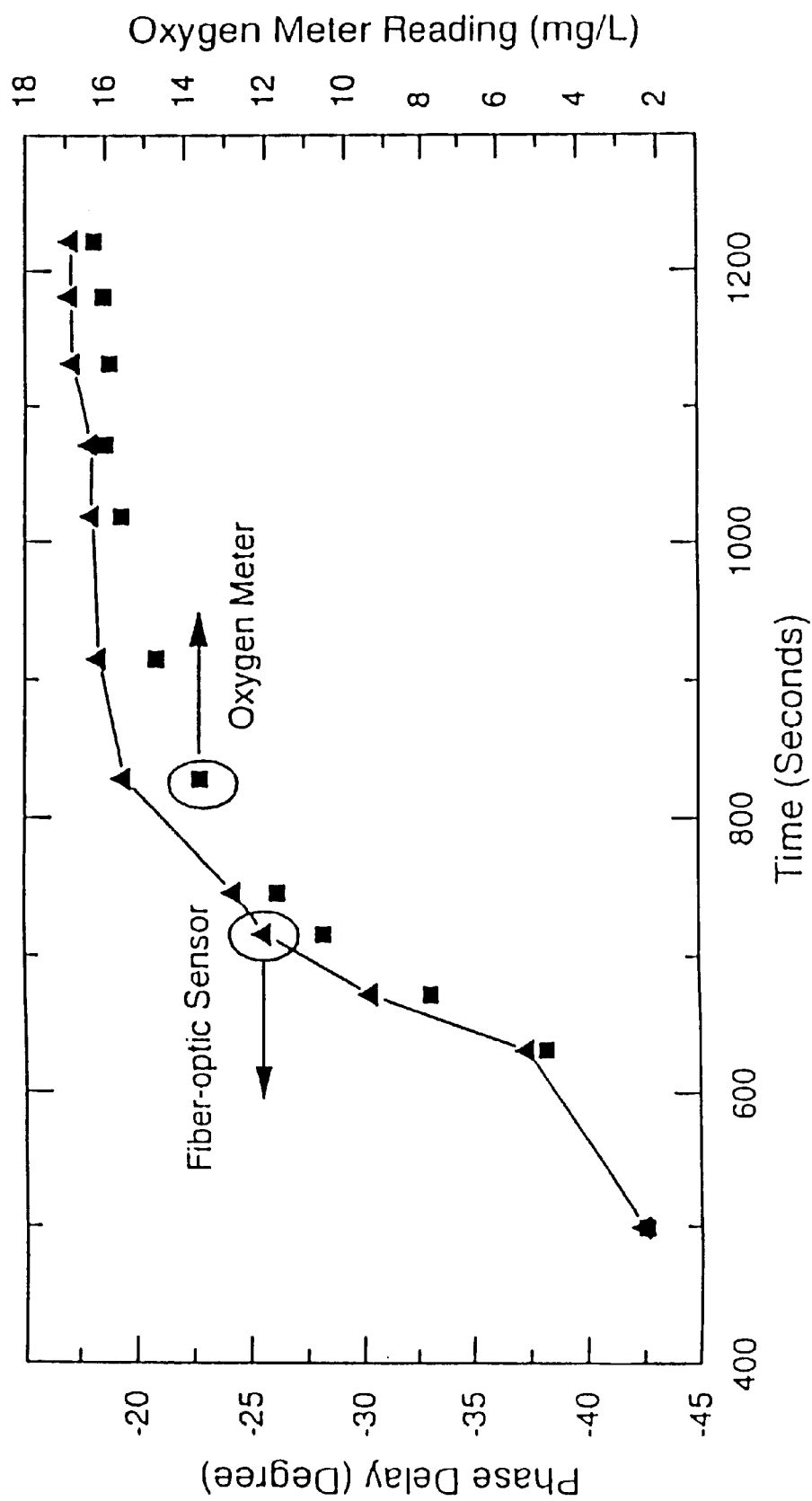
FIG. 37 is a graph for comparison of multiplexed fiber-optic oxygen sensor systems with existing electro-chemical oxygen meter.

FIG. 37 shows a typical measurement response of Type I fiber-optic probe 3 in use with the multiplexed fiberoptic sensor system 43 when pure oxygen was bubbled into a flask of water. The water was previously purged with nitrogen. This figure shows that the performance of the Phase II multiplexed fiber-optic sensor system is identical to existing dissolved-oxygen meters, with additional advantages of monitoring oxygen levels at multiple locations and without consumption of dissolved-oxygen.

Figure 38:
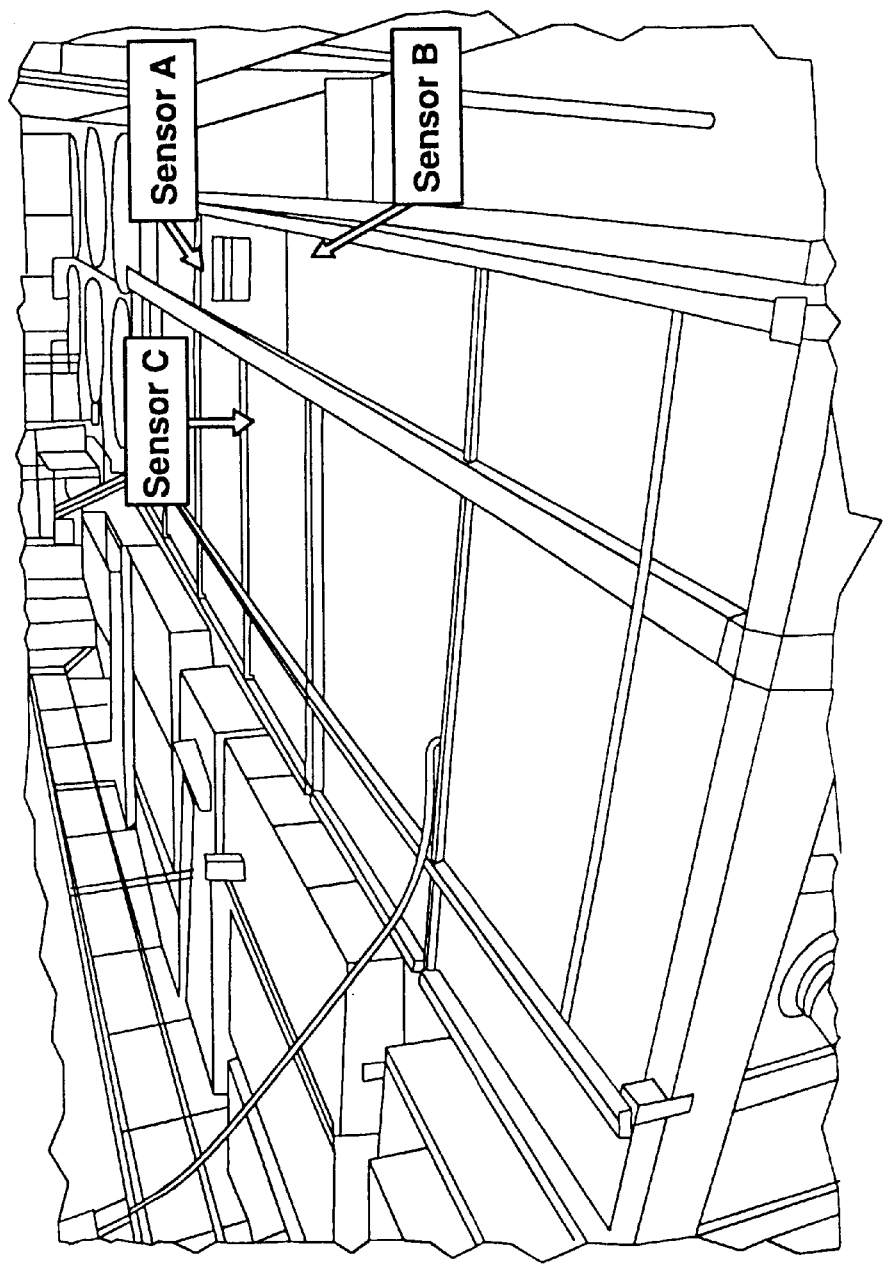
FIG. 38 shows an experimental setup of fiber-optic sensor system at virginia polytechnic institute and state university aquaculture center.
Figure 39:
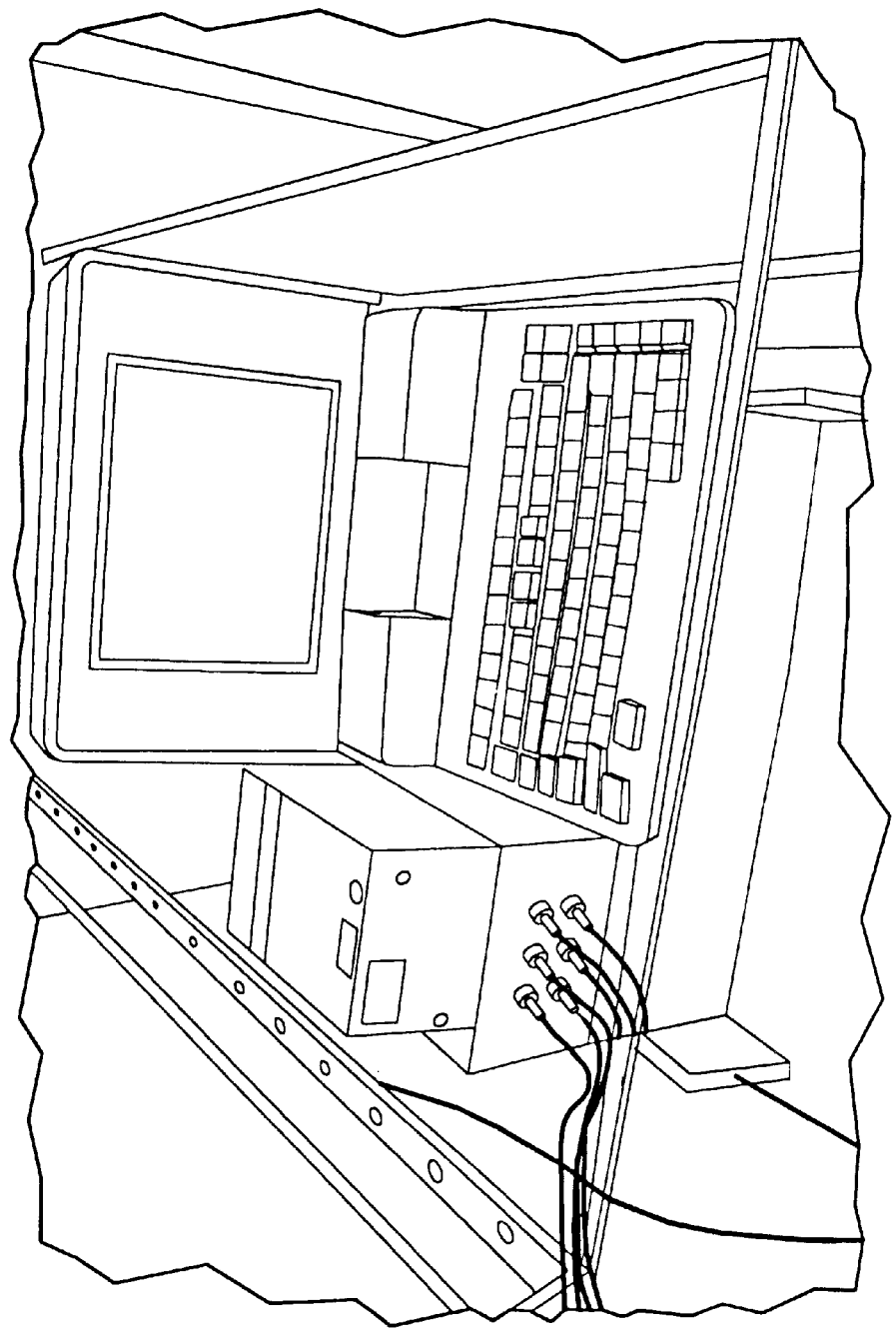
FIG. 39 shows a multiplexed fiber-optic sensor system in operation at virginia polytechnic institute and state university aquaculture center.

FIG. 38 shows a photograph of the multiplexed optical fiber sensors 43 installed in a high-density closed cycle aquaculture facility at the Aquaculture Center at Virginia Polytechnic Institute and State University. The sensor system 43 was operated for over a period of three weeks and no significant problems were encountered. FIG. 39 shows a photograph of the sensor system 43 in operation.

Figure 40:
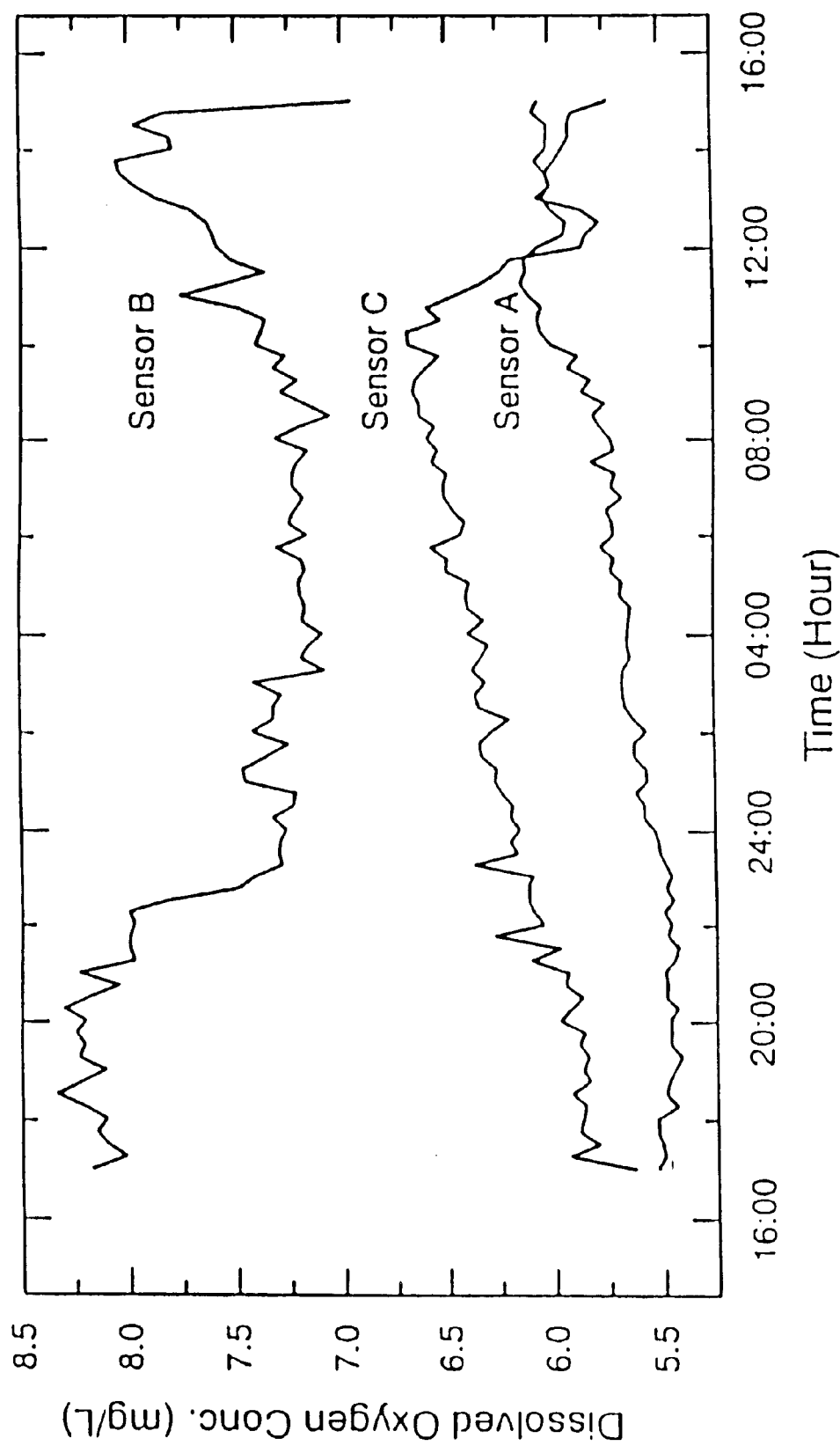
FIG. 40 is a graph of variation of dissolved-oxygen concentrations in the closed-cycle aquaculture tank on a typical day.
Figure 41:
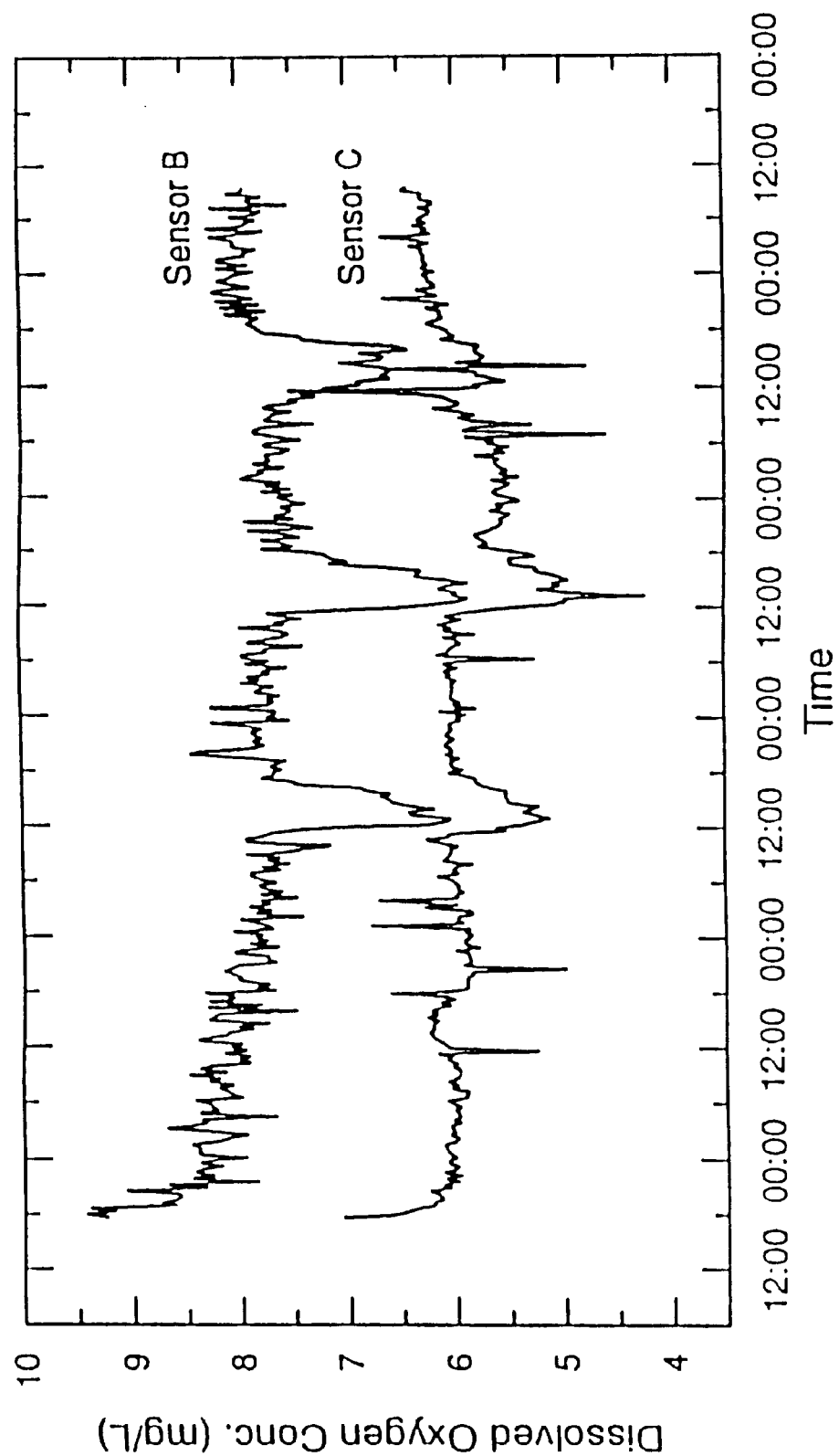
FIG. 41 is a graph of variation of dissolved-oxygen concentration in the closed-cycle aquaculture tank during a five-day period.

FIG. 40 shows the result of measuring dissolved-oxygen concentrations at the closed-cycle aquaculture tank during a typical diurnal cycle. It is observed that during daylight hours, all three sensors measured a drop in dissolved-oxygen levels. This is an expected result, because fish rates of respiration are increased as a result of increased activity during daylight hours before and after feeding. At night, the dissolved-oxygen concentrations slowly increased. FIG. 41 shows the result of continuous measurement of dissolved-oxygen levels in a five-day period. It clearly demonstrates the ability of the sensor system to monitor continuously critical parameters, such as dissolved-oxygen at several locations. This result shows the diurnal cycle of dissolved-oxygen levels following changes in fish respiration. One of the sensors (Sensor A, with a fluorescence film attached to the end of the optical fiber) failed after 5 days of continuous use. The fluorescence signal of the failed sensor dropped to 10% of its original value. The sensor did not show apparent damage to the sensing fiber nor to the film. One speculation on the reason for the sudden failure is that the fluorescent film may have been partially separated from the fiber end. Two other sensors placed in the aquaculture tank continued to operate throughout a two-week test period.

Figure 42:
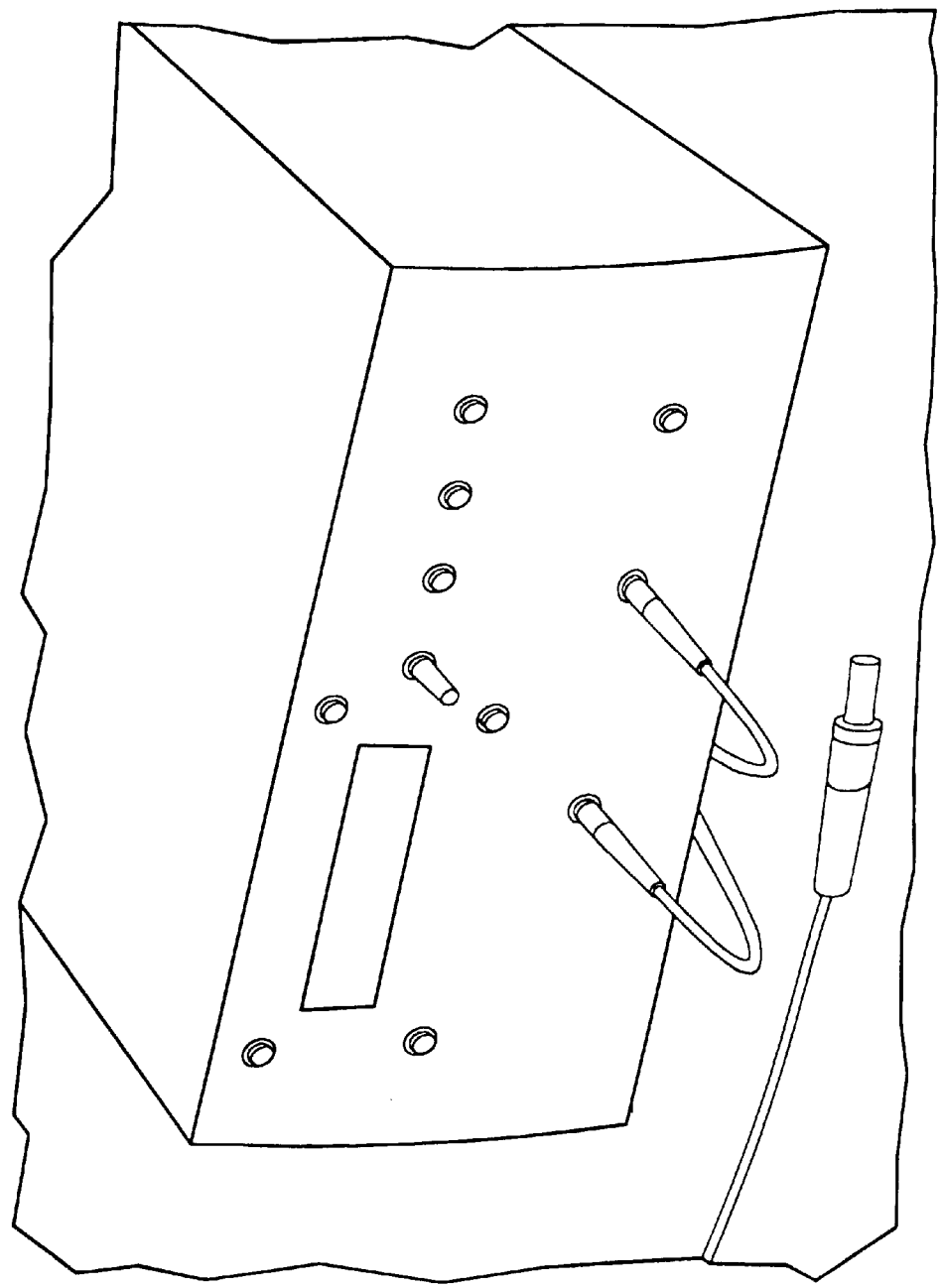
FIG. 42 shows a packaged fiber-optic oxygen sensor system using digital signal processing technology.
Figure 43:
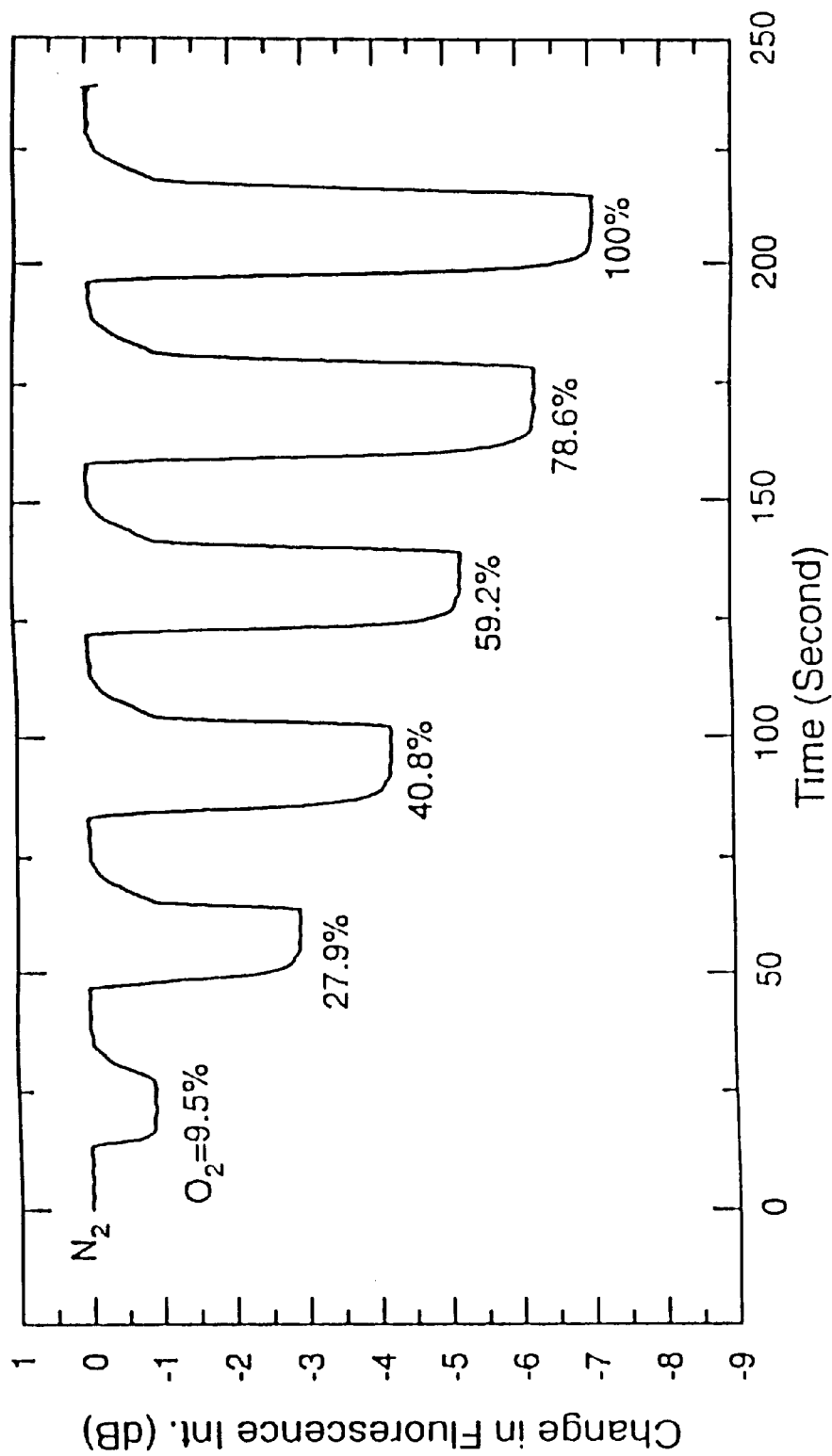
FIG. 43 is a graph of response of fiber-optic sensor to various levels of oxygen.
Figure 44A:
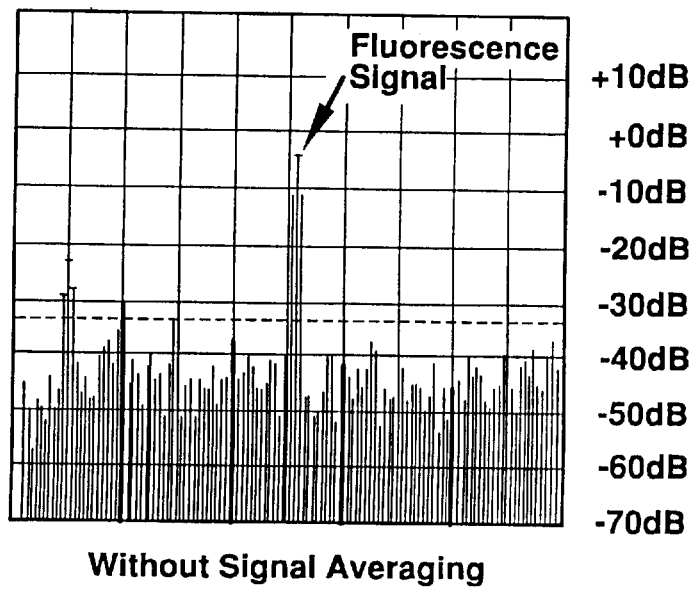
FIG. 44 is a graph of power spectrum of oxygen fluorescence sensor with and without signal averaging.
Figure 44B:
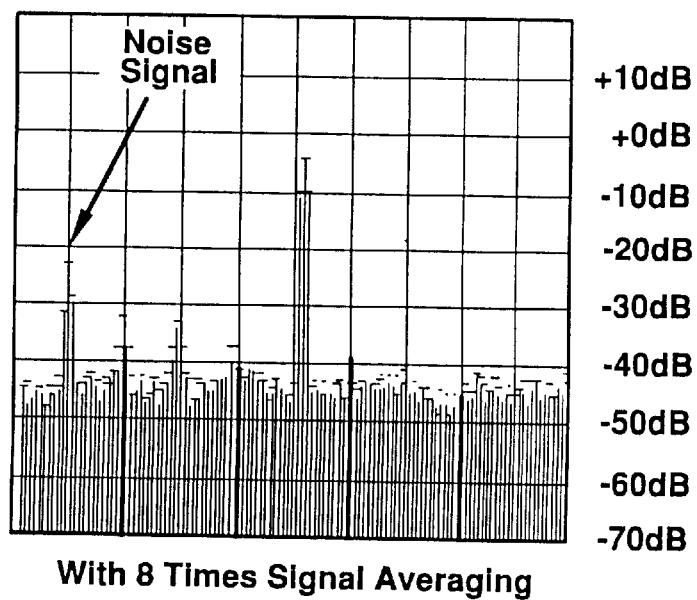

An optimized fiber-optic oxygen sensor system 63 uses the combination of an LED and digital signal processing techniques (FIG. 42). The stability of the system was investigated by measuring the fluorescence output of the sensor in air under laboratory conditions for a period of time. At 20° C. under ambient lighting conditions, the short term (5 minute) fluctuation of the oxygen sensor was 0. 1%, while the sensor fluctuation in one hour was 0.4%. FIG. 43 shows the ON/OFF response of the dye-doped silicone film to different oxygen levels. It shows that the response time of the sensor to pure oxygen or nitrogen is approximately 30 seconds. This figure shows an improved signal-to-noise ratio for low concentrations of oxygen. The signal-to-noise ratio of the sensor was improved through the use of digital signal averaging and fast Fourier transform (FFT) filters. FIG. 44 shows the power spectrum of the fluorescence without averaging and with signal averaging using 8 samples to form a composite signal. The background noise is significantly reduced by digital signal averaging. The noise related to fluorescent lamps in the laboratory setting was efficiently removed by selecting a pass band in the power spectrum before transformation back to the time domain using the inverse FFT. While active analog filtering can be implemented using an instrument such as a lock-in amplifier which has an approximate cost of more than $3,000, the present work demonstrated low-light fluorescence signals can be detected and stabilized using a digital signal processing technique implemented using low-cost electronic hardware.

Figure 45:
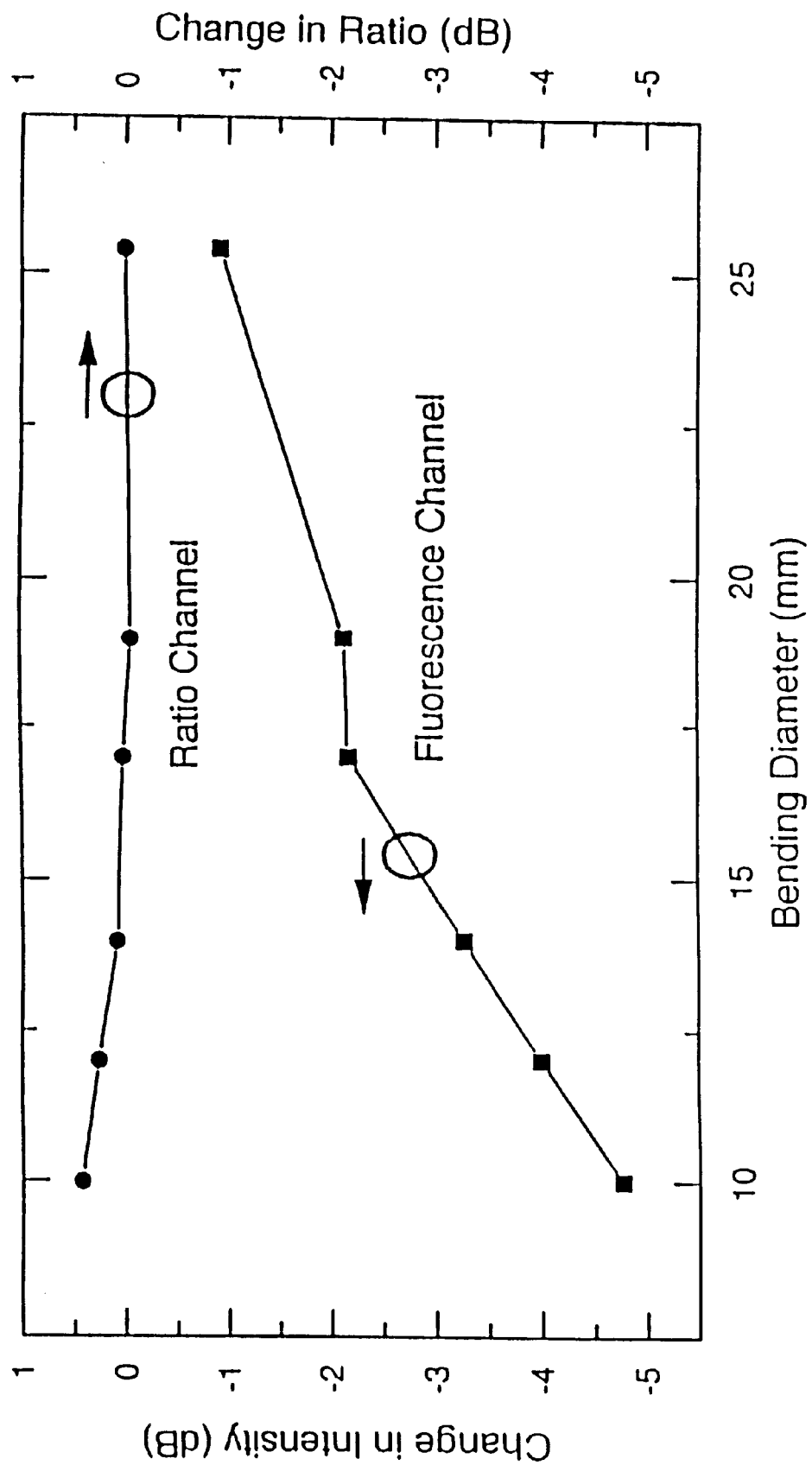
FIG. 45 is a graph of compensation of fiber bending loss when the excitation fiber was bent.

FIG. 45 shows the output of the fluorescence channel when the excitation fiber was bent at various diameters.

Figure 46:
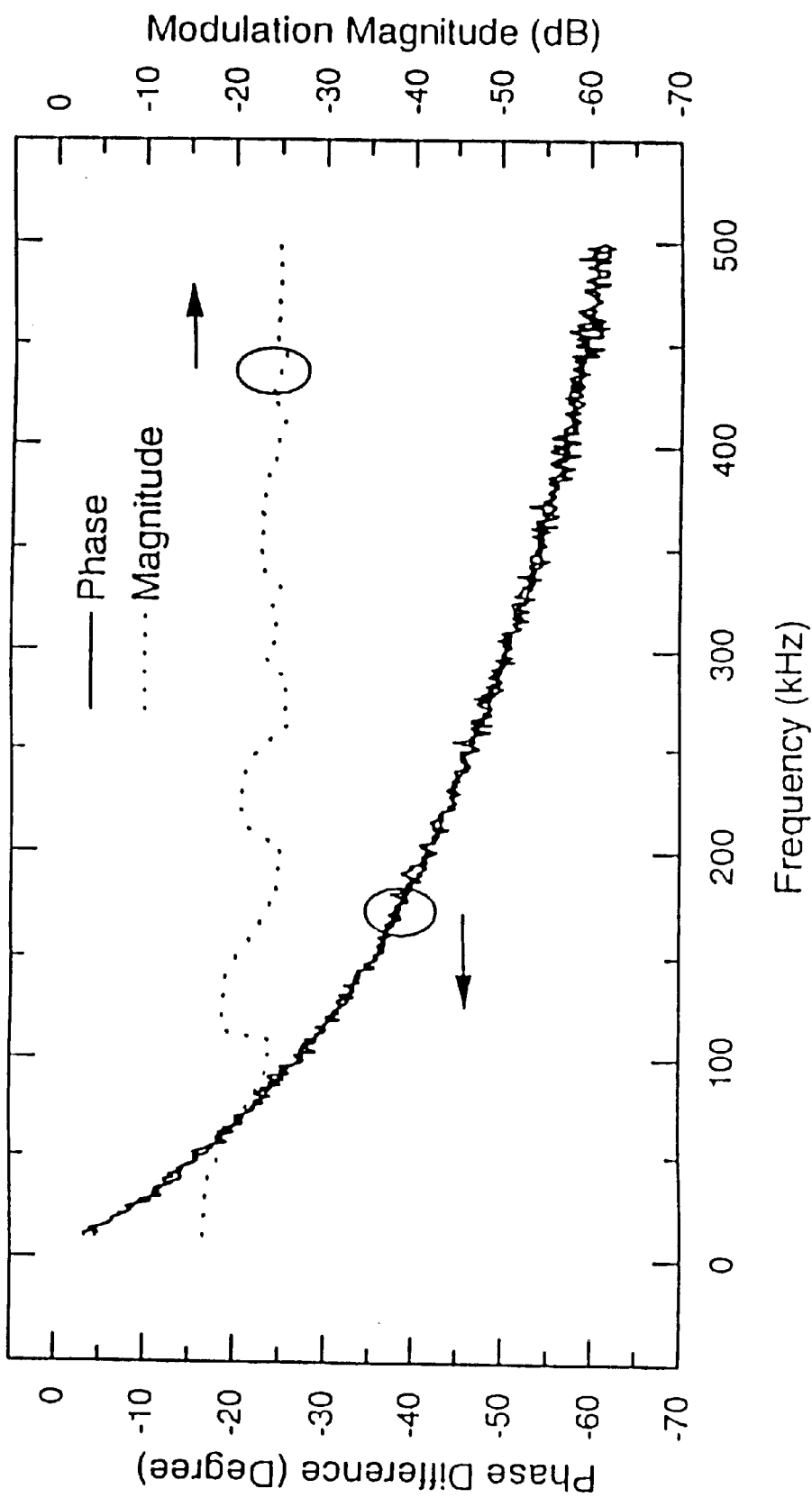
FIG. 46 demonstrates fiber bending loss elimination with phase delay measurement.

These results show that while the fluorescence signal decreased by almost 5 dB when the fiber was bent to 10 mm, the ratio of the fluorescence signal to the excitation signal changed by 0.22 dB. Similar results were obtained when the collection fiber was bent. The decrease in the fluorescence signal was 4.8 dB when the fiber was bent to 10 mm, and the ratio of the fluorescence signal to the excitation signal changed by 0.42 dB. The measurement of the output from the difference amplifier yielded similar results. It was observed that the change in the ratio is greater in the bending of the collection fiber than the excitation fiber. Although the ratiometric method in conjunction with digital signal processing can alleviate the problem of fiber bending in a fluorescence intensity-based sensor, fiber bending loss cannot be completely eliminated. It is speculated that one of the reasons for the inability to remove fiber bending loss completely is that bending loss may be a function of wavelength; therefore, the fluorescence signal and the excitation wavelength will have a slightly different attenuation in fiber bending. FIG. 46 shows a comparison of change in fluorescence signal using a phase delay measurement verses amplitude measurement of fluorescence signal during fiber bending. In this experiment, the optical fiber was bent to a diameter of approximately 2 cm. It was evident that the phase delay signal was not affected by fiber bending even when the signal amplitude was reduced to 25% of its original signal.

Benefits of the present invention include, but are not limited to, the following: Reduced fouling allows the present invention to be used in otherwise unmonitorable locations and reduces down-time. The small size of the present invention provides hand-held instrumentation for process control and increases ease of use. The reduced cost of the present invention through semiconductor integrated circuit design increases the number of applications for which chemical analysis is economical. The compatibility of the present invention with existing RF telecommunications equipment increases chemical processing efficiencies and reduces pollution costs. Multiple wavelength operation of the present invention allows a single probe to be used for multiple chemical analytes and improves probe selectivity. The large number of available probes with the present invention increases the spatial accuracy in chemical analysis and allows use with biological samples.

While the invention has been described with reference to specific embodiments, modifications and variations of the invention may be constructed without departing from the scope of the invention, which is defined in the following claims.

TABLE I

Solubility of Oxygen in Freshwater and Seawater.

| Temperature in ° C. | Solubility in Freshwater in mg/L | Solubility in 35% Salinity Seawater in mg/L |
|---|---|---|
| 0 | 14.6 | 11.3 |
| 5 | 12.8 | 10.0 |
| 10 | 11.3 | 9.0 |
| 15 | 10.2 | 8.1 |
| 20 | 9.2 | 7.4 |
| 25 | 8.4 | 6.7 |
| 30 | 7.6 | 6.1 |
| 35 | 7.1 | 5.7 |
| 40 | 6.6 | 5.3 |

TABLE II

Quenching Efficiency of Ru(bpy)$_3^{2+}$ in Relationship to Sol-gel Film Thickness when Exposed to Air, Oxygen and Nitrogen.

| Spin Rate (rpm) | Film Thickness ($\mu$m) | $I_{air}/I_{N_2}$ (%) | $I_{O_2}/I_{N_2}$ (%) |
|---|---|---|---|
| 3,000 | 6.2 | 17.0 | 24.5 |
| 2,000 | 7.0 | 16.8 | 23.0 |
| 1,500 | 8.8 | 12.2 | 20.0 |
| 1,000 | 12.0 | 8.4 | 13.4 |

TABLE III

Responsibility and Reversibility of Dye-polymer Combinations for NH$_3$ Detection.

| Dye | Fluorescent/absorbent | Matrix | Response to Ammonia | Reversibility |
|---|---|---|---|---|
| Zn(II)-TCPP | Fluorescent | Nafion ® | Yes | Irreversible |
| Zn(II)-TAPP | Fluorescent | Nafion ® | Yes | Irreversible |
| DiIC$_1$(5) | Fluorescent | Nafion ® | Yes | Irreversible |
| OX170 | Fluorescent | Nafion ® | Yes | Irreversible |
| Nile Blue | Fluorescent | PEM | Yes | Reversible |
| BTB | Absorbent | Nafion ® | Yes | Irreversible |
| BTB | Absorbent | PVPOH | Yes | Reversible |
| BTB | Absorbent | PCBA | Yes | Reversible |
| BTB | Absorbent | PEM | Yes | Reversible |
| BTB | Absorbent | PVP | Yes | Reversible |
| BCP | Absorbent | PEM | Yes | Reversible |
| CPR | Absorbent | PEM | Yes | Reversible |
| NY | Absorbent | PEM | Yes | Reversible |

TABLE IV

Molecular Weight Data for the Polymerization of Lactic Acid.

| No. | Starting Material | Method | Temp (° C.) | Time (hours) | % Yield | Mol. Wt. kg/mol |
|---|---|---|---|---|---|---|
| 1 | L-lactic acid | Direct Polycondensation (PC) | 200 | 20 | 48 | 6.3 |
| 2 | L-lactic acid | Direct PC | 200 | 30 | 18 | 28 |
| 3 | D,L-lactic acid | PC with antimony oxide as catalyst | 220 | 30 | 65 | 4.2 |
| 4 | L-lactic acid | PC with catalyst | 220 | 15 | 43 | 2.9 |
| 5 | L-lactide | Ring opening polymerization (ROP) with antimony trifluoride as catalyst | 140 | 48 | 20 | 6.5 |
| 6 | D,L-lactide | ROP with stannous octonoate as catalyst in sealed tube | 145 | 30 | 100 | 99 |

TABLE V

Large Scale Reaction of Crosslinked Polyesters.

| Mol % of Crosslinker | (%) Yield | (%) Gel Fraction | $T_g$ (° C.) | TGA 5% Wt Loss |
|---|---|---|---|---|
| 15 | 67 | 84 | 90.9 | 248 |
| 25 | 71 | 93 | 93.2 | 256 |

TABLE VI

Data on the Biodegradability Studies of 15 mol % Crosslinker.

| Mol % of Crosslinker[a] | Initial Wt (grams) | Wt[b] #1 | Wt[c] #2 | Time (hours) | Average loss in wt. (grams) |
|---|---|---|---|---|---|
| 15 | 1.1343 | 1.1004 | 1.1007 | 51 | 0.0338 |
| 15 | 2.0507 | 1.9633 | 1.9602 | 102 | 0.0890 |
| 15 | 2.0784 | 1.8712 | 1.8703 | 149 | 0.208 |
| 15 | 2.0461 | 1.6562 | 1.6556 | 196 | 0.390 |
| 15 | 2.0200 | 1.4142 | 1.4139 | 245 | 0.606 |

TABLE VII

Data on the Biodegradability Studies of 25 mol % Crosslinker.

| Mol % of Crosslinker[a] | Initial Wt (grams) | Wt[b] #1 | Wt[c] #2 | Time (hours) | Average loss in wt. (grams) |
|---|---|---|---|---|---|
| 25 | 2.0199 | 2.0112 | 1.9976 | 54 | 0.0155 |
| 25 | 2.0476 | 1.9686 | 1.9674 | 102 | 0.0796 |
| 25 | 2.0317 | 1.8675 | 1.8671 | 149 | 0.164 |
| 25 | 2.0454 | 1.7878 | 1.7872 | 196 | 0.258 |
| 25 | 2.0394 | 1.7176 | 1.7170 | 245 | 0.322 |

We claim:

1. An optical chemical probe comprising at least one dye for detecting the presence of chemical analytes, and polymeric film media for binding the at least one dye, wherein the polymeric film media is comprised of consecutive layers of anionic and cationic polyelectrolytes.

2. The probe of claim 1, wherein there are at least 3 and no more than 5 layers of each of the anionic and cationic polyelectrolytes.

3. The probe of claim 1, wherein the at least one dye is a dye having metachromasy property.

4. The probe of claim 3, wherein the dye is a triphenylmethane dye.

5. The probe of claim 1, wherein the at least one dye is diprotonated in acid media selected from a group consisting of bromocresol purple, bromophenol blue, thymol blue or bromothymol blue.

6. The probe of claim 1, wherein the at least one dye bonds to the layers of anionic and cationic polyelectrolytes through hydrogen bonding, charge interaction or other non-covalent methods.

7. The probe of claim 1, further comprising a thin Teflon protective film for coating the sensor.

8. A chemical sensor apparatus comprising at least one dye for detecting the presence of chemical analytes, polymeric film media for binding the at least one dye, a light source for generating optical signals corresponding to changes in the optical absorption spectrum and fluorescence of the dye, and a detector positioned near the polymeric film media for sensing the optical signals, wherein the polymeric film media is comprised of consecutive layers of anionic and cationic polyelectrolytes.

9. The apparatus of claim 8, wherein there are at least 3 and no more than 5 layers of anionic and cationic polyelectrolytes.

10. The apparatus of claim 8, wherein the at least one dye is a dye having metachromasy property.

11. The apparatus of claim 10, wherein the at least one dye is a triphenylmethane dye.

12. The apparatus of claim 8, wherein the at least one dye is diprotonated in acid media selected from a group consisting of bromocresol purple, bromophenol blue, thymol blue or bromothymol blue.

13. The apparatus of claim 8, wherein the at least one dye bonds to the polymeric film media through hydrogen bonding, charge interaction or other non-covalent methods.

14. The apparatus of claim 8, wherein changes in the optical absorption are detected using a standard UV-visible spectrophotometer.

15. The apparatus of claim 8, further comprising a thin Teflon protective film for coating the sensor.

16. The apparatus of claim 8, further comprising a red light source.

17. The apparatus of claim 8, wherein the light source is a modulated light source directed toward the polymeric film media for producing a modulated light signal and for generating optical signals corresponding to changes in the optical absorption spectrum.

18. The apparatus of claim 8, further comprising an electronic light modulator connected to the light source for modulating the light source and a signal processor connected to the light modulator and to the detector for sequentially modulating the light source, for collecting an electronic signal from the detector for providing improved signal-to-noise ratio, for conditioning electronic signals, and for identifying and measuring concentration of an analyte.

19. The apparatus of claim 8, wherein changes in fluorescence are measured using a photodetector equipped with a long-wavelength-pass filter or a bandpass filter.

20. A chemical sensor apparatus comprising an optical waveguide, at least one dye for detecting the presence of chemical analytes; polymeric film media positioned on the waveguide for binding the at least one dye, a light source for generating optical signals corresponding to changes in the optical absorption spectrum of the dye, and a detector positioned near the waveguide for sensing the optical signals, wherein the waveguide has at least two regions of differing polymeric media with different dyes bound to the polymeric media and wherein the polymeric film media is comprised of consecutive layers of anionic and cationic polyelectrolytes.

21. The apparatus of claim 20, wherein the detector further comprises multiple photodetectors equal in number to a number of the regions, and wherein each photodetector receives and evaluates an optical signal from only one region.

22. A method for identifying concentration of a chemical analyte comprising incorporating at least one dye in consecutive layers of anionic and cationic polyelectrolytes; placing the layers and dyes into the media to be analyzed; and detecting changes in the optical absorption of the layers and dyes.

23. The method of claim 22, further comprising using digital Fourier transform techniques to filter extraneous noise sources from the chemical sensor.

24. A method for identifying concentration of a chemical analyte in either gaseous or liquid phase comprising incorporating at least one dye in consecutive layers of anionic and cationic polyelectrolytes; placing the layers and dyes into the media to be analyzed; using a light source to create optical signals corresponding to changes in the optical absorption spectrum; trapping the optical signals; detecting the optical signals; collecting the optical signals; and converting the optical signals to electronic signals.

* * * * *